(12) United States Patent
Lozac'hmeur et al.

(10) Patent No.: US 11,043,304 B2
(45) Date of Patent: Jun. 22, 2021

(54) SYSTEMS AND METHODS FOR USING SEQUENCING DATA FOR PATHOGEN DETECTION

(71) Applicant: Tempus Labs, Inc., Chicago, IL (US)

(72) Inventors: Ariane Lozac'hmeur, Chicago, IL (US); Denise Lau, Santa Monica, CA (US); Aly A. Khan, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 16/802,126

(22) Filed: Feb. 26, 2020

(65) Prior Publication Data

US 2020/0273576 A1 Aug. 27, 2020

Related U.S. Application Data

(60) Provisional application No. 62/810,849, filed on Feb. 26, 2019.

(51) Int. Cl.

| | |
|---|---|
| *G01N 33/48* | (2006.01) |
| *G01N 33/50* | (2006.01) |
| *G16H 50/20* | (2018.01) |
| *G16H 10/40* | (2018.01) |
| *G16H 50/70* | (2018.01) |
| *A61K 31/513* | (2006.01) |
| *A61K 31/337* | (2006.01) |
| *C07K 16/22* | (2006.01) |
| *A61K 33/243* | (2019.01) |
| *A61K 45/06* | (2006.01) |

(52) U.S. Cl.
CPC ............ *G16H 50/20* (2018.01); *A61K 31/337* (2013.01); *A61K 31/513* (2013.01); *A61K 33/243* (2019.01); *C07K 16/22* (2013.01); *G16H 10/40* (2018.01); *G16H 50/70* (2018.01); *A61K 45/06* (2013.01)

(58) Field of Classification Search
CPC ........ G16H 50/20; G16H 10/40; G16H 50/70; A61K 31/513; A61K 31/337; A61K 33/243; A61K 45/06; A61K 31/555; A61K 31/282; C07K 16/22; G01N 33/57484

See application file for complete search history.

(56) References Cited

U.S. PATENT DOCUMENTS

| | | | |
|---|---|---|---|
| 2008/0003565 A1* | 1/2008 | Baptista | ................... C12Q 1/70 435/5 |
| 2011/0301059 A1 | 12/2011 | Pyeon et al. | |
| 2018/0357361 A1 | 12/2018 | Frenkel et al. | |
| 2019/0256924 A1 | 8/2019 | Vogelstein et al. | |

FOREIGN PATENT DOCUMENTS

| | | |
|---|---|---|
| WO | WO 2012/128658 A1 | 9/2012 |
| WO | WO 2018/048960 A1 | 3/2018 |
| WO | WO 2019/032525 A1 | 2/2019 |

OTHER PUBLICATIONS

Golub et al. Molecular classification of cancer: class discovery and class prediction by gene expression monitoring. Science, vol. 286, pp. 531-537. (Year: 1999).*

"Comprehensive genomic characterization of head and neck squamous cell carcinomas," The Cancer Genome Atlas Network, 576 | Nature | vol. 517 | Jan. 29, 2015, pp. 1-7.

"Comprehensive molecular characterization of gastric adenocarcinoma," The Cancer Genome Atlas Network, 202 | Nature | vol. 513 | Sep. 11, 2014, pp. 1-8.

"Integrated genomic and molecular characterization of cervical cancer," The Cancer Genome Atlas Network, 378 | Nature | vol. 543 | Mar. 16, 2017, pp. 1-23.

Bass, Adam J., et al. "Comprehensive molecular characterization of gastric Adenocarcinoma," Nature, Sep. 11, 2014, pp. 1-20.

Dahmus, Jessica D. et al. "The gut microbiome and colorectal cancer: a review of bacterial Pathogenesis," Journal of Gastrointestinal Oncology, 2018; 9 (4), pp. 769-777.

De Flora, Silvio, et al. "The prevention of infection-associated cancers," Carcinogenesis, vol. 32, No. 6 (2011) pp. 787-795.

Gameiro, Steven F., et al. "Treatment-naïve HPV+ head and neck cancers display a T-cell-inflamed phenotype distinct from their HPV-counterparts that has implications for immunotherapy," ISSN: (Print) 2162-402X (Online) Journal homepage: https://www.tandfonline.com/loi/koni20, Oncoimmunology, 2018, vol. 7, No. 10, pp. 1-15.

Gulley, Margaret L. "Genomic assays for Epstein—Barr virus-positive gastric adenocarcinoma," Experimental & Molecular Medicine (2015) 47, pp. 1-12.

Rooney, Michael S., et al. "Molecular and Genetic Properties of Tumors Associated with Local Immune Cytolytic Activity," Cell 160, Jan. 15, 2015, pp. 48-61.

Young, Neil, et al. "The Opisthorchis viverrini genome provides insights into life in the bile duct", Nature Communications, 5:4378, DOI: 10.1038/ncomms56378, published Jul. 9, 2014, 11 pages.

Editorial—EBV and human cancer, Experimental & Molecular Medicine, 2015, 47, e130, pp. 1-3.

Akhtar, Saghir, et al. "Epstein-Barr Virus in Gliomas: Cause, Association, or Artifact?," Frontiers in Oncology, Apr. 20, 2018, vol. 8, Article 123, pp. 1-10.

(Continued)

*Primary Examiner* — Russell S Negin

(74) *Attorney, Agent, or Firm* — Morgan, Lewis & Bockius LLP

(57) ABSTRACT

Systems and methods are provided for training a classifier to discriminate between a first cancer condition associated with an oncogenic pathogenic infection a second cancer condition that is not associated with an oncogenic pathogenic infection. Systems and methods are provided for distinguishing cancers associated with oncogenic pathogenic infections that contribute to the cancer pathology and cancers that are not associated with oncogenic pathogenic infections. Systems and methods are provided for treating cancer based on whether the cancer is associated with an oncogenic pathogenic infection.

13 Claims, 20 Drawing Sheets

(56) References Cited

OTHER PUBLICATIONS

Amador-Molina, Alfredo, et al. "Role of Innate Immunity against Human Papillomavirus (HPV) Infections and Effect of Adjuvants in Promoting Specific Immune Response," Viruses, 2013, 5, pp. 2624-2642.

Birdwell, Christine E., et al. "Genome-Wide DNA Methylation as an Epigenetic Consequence of Epstein-Barr Virus Infection of Immortalized Keratinocytes," Journal of Virology, Oct. 2014, vol. 88, No. 19, pp. 11442-11458.

Chang, Yuan, et al. "Merkel Cell Carcinoma: A Virus-Induced Human Cancer," Annual Review Pathol. Mech. Dis., 2012, 7, pp. 123-144.

Deschuymer, Sarah, et al. "Toxicity Reduction in the Treatment of HPV Positive Oropharyngeal Cancer: Emerging Combined Modality Approaches," Frontiers in Oncology, Oct. 9, 2018, vol. 8, Article 439, pp. 1-9.

Greenough, Thomas C., et al. "A Gene Expression Signature That Correlates with CD8+ T Cell Expansion in Acute EBV Infection," 2015, 195, The Journal of Immunology, pp. 4185-4197.

Iizasa, Hisashi, et al. "Epstein-Barr Virus (EBV)-associated Gastric Carcinoma," Viruses, 2012, 4, pp. 3420-3439.

Kim, Sun Young, et al. "Deregulation of Immune Response Genes in Patients With Epstein-Barr Virus-Associated Gastric Cancer and Outcomes," Gastroenterology, 2015, 148, pp. 137-147.

Martin, Heather, J., et al. "Manipulation of the Toll-Like Receptor 7 Signaling Pathway by Epstein-Barr Virus," Journal of Virology, vol. 81, No. 18, Sep. 2007, pp. 9748-9758.

Nakayama, Chiemi, et al. "Transduced caudal-type homeobox (CDX) 2/CDX1 can induce growth inhibition on CDX-deficient gastric cancer by rapid intestinal differentiation," Cancer Science, 2018, 109, pp. 3853-3864.

Salehipoor, Mehdi, et al. "Role of Viruses in Renal Cell Carcinoma," Saudi Journal of Kidney Diseases and Transplantation, 2012, 23(1), pp. 53-57.

Shinozaki, Aya, et al. "Epstein-Barr Virus—associated Gastric Carcinoma: A Distinct Carcinoma of Gastric Phenotype by Claudin Expression Profiling," Journal of Histochemistry & Cytochemistry, vol. 57(8), 2009, pp. 775-785.

Shinozaki-Ushiku, Aya, et al. "Update on Epstein-Barr virus and gastric cancer," Sandidos-publications.com/10.3892/ijo.2015.2856, 2015, pp. 1-36.

Song, Dan, et al. "Effect of human papillomavirus infection on the immune system and its role in the course of cervical cancer," Oncology Letters 10: 2015, pp. 600-606.

Stamatiou, Dimitris P., et al. "Herpes and polyoma family viruses in thyroid cancer," Oncology Letters, 2016, pp. 1635-1644.

Strong, Michael J., et al. "Differences in Gastric Carcinoma Microenvironment Stratify According to EBV Infection Intensity: Implications for Possible Immune Adjuvant Therapy," PLOS Pathogens, May 2013, vol. 9, Issue 5, pp. 1-18.

Tang, Ka-Wei, et al. "The landscape of viral expression and host gene fusion and adaptation in human cancer," Nature Communications, Published Oct. 1, 2013, pp. 1-9.

Tang, Ka-Wei, et al. "Tumour virology in the era of high-throughput genomics," Philosophical Transactions B, 2017, pp. 1-7.

Tashiro, Haruko, et al. "Immunotherapy against cancer-related viruses," Cell Research, 2017, 27, pp. 59-73.

Xu, Wenjia, et al. "Viruses, Other Pathogenic Microorganisms and Esophageal Cancer," Gastro Intestinal Tumors, 2015, 2, pp. 2-13.

Liu, Yang, et al. "Comparative Molecular Analysis of Gastrointestinal Adenocarcinomas," Cancer Cell 33, CellPress, Apr. 9, 2018, pp. 721-735.

Yang, Xiao, et al. "The role of TLRs in cervical cancer with HPV infection: a review," Signal Transduction and Targeted Therapy (2017), pp. 1-10.

Tjalma, W.A.A. "HPV negative cervical cancers and primary HPV screening", Opinion paper, Facts Views Vis Obgyn, pp. 107-113, 2018.

\* cited by examiner

204 Obtain a dataset comprising a corresponding plurality of abundance values for each respective subject in a plurality of subjects of a single species. Each respective abundance value in the corresponding plurality of abundance values quantifies a level of expression of a corresponding gene, in a plurality of genes, in a tumor sample of the respective subject. The dataset further comprises an indication of cancer condition of each subject. The indication of cancer condition identifies whether a respective subject has the first or second cancer condition. The plurality of subjects includes a first subset of subjects that are afflicted with the first cancer condition and a second subset of subjects that are afflicted with the second condition.

218 Identify a discriminating gene set using the corresponding plurality of abundance values and respective indication of the cancer condition of respective subjects in the plurality of subjects. The discriminating gene set comprises a subset of the plurality of genes.

242 Use the respective abundance values for the discriminating gene set and the respective indication of cancer condition across the plurality of subjects to train a classifier to discriminate between the first cancer condition and the second cancer condition as a function of respective abundance values for the discriminating gene set.

246 Use the classifier to classify a test subject to the first or second cancer condition (or determine a likelihood that the test subject has the first or second cancer condition) by inputting a test plurality of abundance values into the classifier. Each respective abundance value in the test plurality of abundance values quantifies a level of expression of a corresponding gene, in the plurality of genes, in a tumor sample of the test subject.

248 Provide a therapeutic intervention or imaging of the test subject based on a determination that the test subject has the first cancer condition or the second cancer condition (or likelihood that the test subject has the first or second cancer condition).

Figure 2A

202 A method for training a classifier to discriminate between a first cancer condition and a second cancer condition is provided. The first cancer condition is associated with infection by a first oncogenic pathogen and the second cancer condition is associated with an oncogenic pathogen-free status.

204 Obtain a dataset comprising a corresponding plurality of abundance values for each respective subject in a plurality of subjects of a single species. Each respective abundance value in the corresponding plurality of abundance values quantifies a level of expression of a corresponding gene, in a plurality of genes, in a tumor sample of the respective subject. The dataset further includes an indication of cancer condition of each respective subject. The indication of cancer condition identifies whether the respective subject has the first or second cancer condition. The plurality of subjects includes a first subset of subjects that are afflicted with the first cancer condition and a second subset of subjects that are afflicted with the second condition.

206 The corresponding plurality of abundance values is obtained by RNA-seq.

208 Each subject in the plurality of subjects afflicted with a first type of cancer and wherein the first type of cancer is one of breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer.

210 Each subject in the plurality of subjects afflicted with a first stage of a first type of cancer. The first type of cancer is one of breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer. The first stage of cancer is stage I, stage II, stage III, or stage IV.

212 The plurality of subjects comprises one hundred subjects, the first subset of subjects comprises twenty subjects, and the second subset of subjects comprises twenty subjects.

Figure 2B

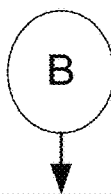

218 Continued . . .

226 Continued . . .

228 Identify the discriminating gene set by splitting the dataset into a plurality of sets (e.g., between five and fifty sets, exactly 10 sets, etc.). Each set in the plurality of sets includes two or more subjects that are afflicted with the first cancer condition and two or more subjects that are afflicted with the second condition. Each respective set in the plurality of sets is independently regressed based on all or a subset of the plurality of abundance values across the subjects of the respective set against the respective indication of cancer condition across the subjects of the respective set using the regression algorithm to thereby assign a corresponding regression coefficient, in the plurality of regression coefficients, to each respective gene in the plurality of genes. Those genes in the plurality of genes that are assigned a regression coefficient by the regression algorithm that satisfies a coefficient threshold for at least a threshold percentage of the plurality of sets is selected for the discriminating gene set.

230 The regression coefficient threshold is zero

232 The regression coefficient threshold is greater than zero.

234 The regression algorithm is logistic regression.

236 The regression algorithm is logistic regression that assumes:

$$P(Y = 1 | x_i) = \frac{\exp(\beta_0 + \beta_1 x_{i1} + \ldots + \beta_k x_{ik})}{1 + \exp(\beta_0 + \beta_1 x_{i1} + \ldots + \beta_k x_{ik})},$$

where $x_i = (x_{i1}, x_{i2}, \ldots, x_{ik})$ are the corresponding plurality of abundance values for the plurality of genes from the tumor sample of the $i^{th}$ corresponding subject, Y is in the set {0, 1} and is a class label that has the value "1" when the corresponding subject $i$ has the first cancer condition and has the value "0" when the corresponding subject $i$ has the second cancer condition, $\beta_0$ is an intercept, and $\beta_j = (j=1,\ldots k)$ is the plurality of regression coefficients, where each respective regression coefficient in the plurality of regression coefficients is for a corresponding gene in the plurality of genes.

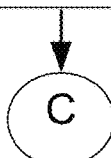

Figure 2D

218 Continued...

226 Continued...

236 Continued...

238 The logistic regression is logistic least absolute shrinkage and selection operator (LASSO) regression in which $\beta_j$ is subject to the constraint:

$\min(\sum_{i=1}^{n}[-y_i(\beta_0 + \beta_1 x_i + ... + \beta_k x_{ik}) + \log(1 + \exp(\beta_0 + \beta_1 x_i + ... + \beta_k x_{ik}))])$, where:

$\sum_{j=1}^{k}|\beta_j| \leq \lambda$, and $\lambda$ is a constant.

240 The regression algorithm is logistic regression with L1 or L2 regularization.

242 Use the respective abundance values for the discriminating gene set and the respective indication of cancer condition across the plurality of subjects to train a classifier to discriminate between the first and second cancer condition as a function of respective abundance values for the discriminating gene set.

244 The classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm.

246 Use the classifier to classify a test subject to the first cancer or to the second condition (or determine a likelihood that the test subject ahs the first or second cancer condition) by inputting a test plurality of abundance values into the classifier. Each respective abundance value in the test plurality of abundance values quantifies a level of expression of a corresponding gene, in the plurality of genes, in a tumor sample of the test subject.

248 Provide a therapeutic intervention or imaging of the test subject based on a determination that the test subject has the first cancer condition or the second cancer condition (or likelihood that the test subject has the first or second cancer condition).

Figure 2E

Datasets composition

HPV Classification

| TCGA (Training) | Head and Neck Cancer | Cervical Cancer | Total |
|---|---|---|---|
| HPV Positive | 32 | 156 | 188 |
| HPV Negative | 231 | 8 | 239 |
| Total | 263 | 164 | 427 |

| Tempus (Testing) | Head and Neck Cancer | Cervical Cancer | Total |
|---|---|---|---|
| HPV Positive | 28 | 28 | 56 |
| HPV Negative | 65 | 12 | 77 |
| Total | 93 | 40 | 133 |

Figure 4A

HPV Selected Features

| Ensembl id | Gene name | Feature type |
|---|---|---|
| ENSG00000170442 | KRT86 | Gene expression |
| ENSG00000121005 | CRISPLD1 | Gene expression |
| ENSG00000134760 | DSG1 | Gene expression |
| ENSG00000149212 | SESN3 | Gene expression |
| ENSG00000173157 | ADAMTS20 | Gene expression |
| ENSG00000170549 | IRX1 | Gene expression |
| ENSG00000077935 | SMC1B | Gene expression |
| ENSG00000147889 | CDKN2A | Gene expression |
| ENSG00000108947 | EFNB3 | Gene expression |
| ENSG00000145824 | CXCL14 | Gene expression |
| ENSG00000105278 | ZFR2 | Gene expression |
| ENSG00000178222 | RNF212 | Gene expression |
| ENSG00000179455 | MKRN3 | Gene expression |
| ENSG00000196074 | SYCP2 | Gene expression |
| ENSG00000168530 | MYL1 | Gene expression |
| ENSG00000095777 | MYO3A | Gene expression |
| ENSG00000182545 | RNASE10 | Gene expression |
| ENSG00000144278 | GALNT13 | Gene expression |
| ENSG00000099625 | CBARP | Gene expression |
| ENSG00000145113 | MUC4 | Gene expression |
| ENSG00000254221 | PCDHGB1 | Gene expression |
| ENSG00000110092 | CCND1 | Gene expression |
| ENSG00000240386 | LCE1F | Gene expression |
| ENSG00000124134 | KCNS1 | Gene expression |
| ENSG00000147889 | CDKN2A | Number of mutations |
| ENSG00000141510 | TP53 | Number of mutations |

Figure 4B

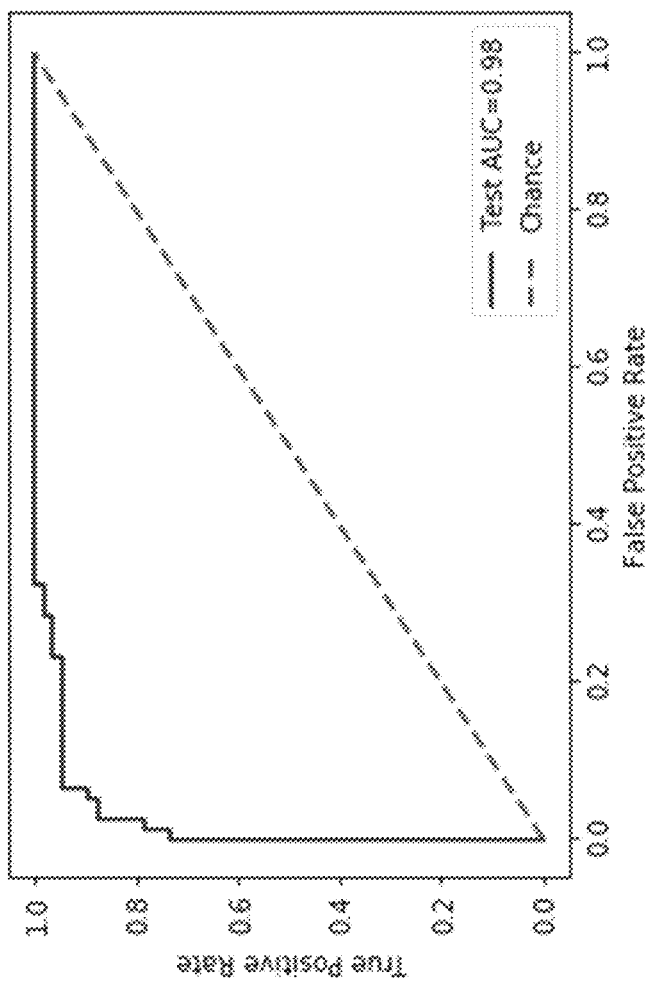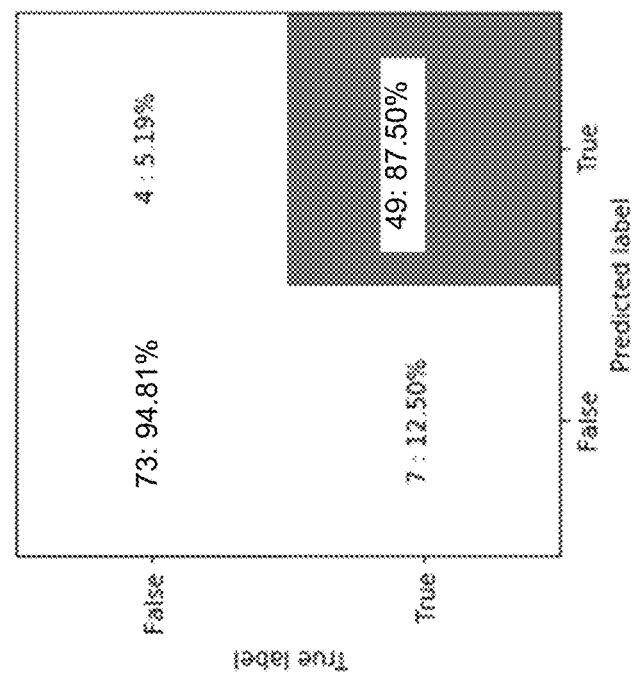
Figure 4D

EBV Classification

Datasets composition

| TCGA (Training) | Gastric Cancer |
|---|---|
| EBV Positive | 21 |
| EBV Negative | 191 |
| Total | 212 |

| Tempus (Testing) | Gastric Cancer |
|---|---|
| EBV Positive | 4 |
| EBV Negative | 51 |
| Total | 55 |

Figure 5A

EBV Selected Features

| Ensembl id | Gene name | Feature type |
|---|---|---|
| ENSG00000111319 | SCNN1A | Gene expression |
| ENSG00000113722 | CDX1 | Gene expression |
| ENSG00000124249 | KCNK15 | Gene expression |
| ENSG00000126583 | PRKCG | Gene expression |
| ENSG00000135480 | KRT7 | Gene expression |
| ENSG00000145506 | NKD2 | Gene expression |
| ENSG00000151025 | GPR158 | Gene expression |
| ENSG00000165215 | CLDN3 | Gene expression |
| ENSG00000176083 | ZNF683 | Gene expression |
| ENSG00000121879 | PIK3CA | Number of mutations |
| ENSG00000141510 | TP53 | Number of mutations |

Figure 5B

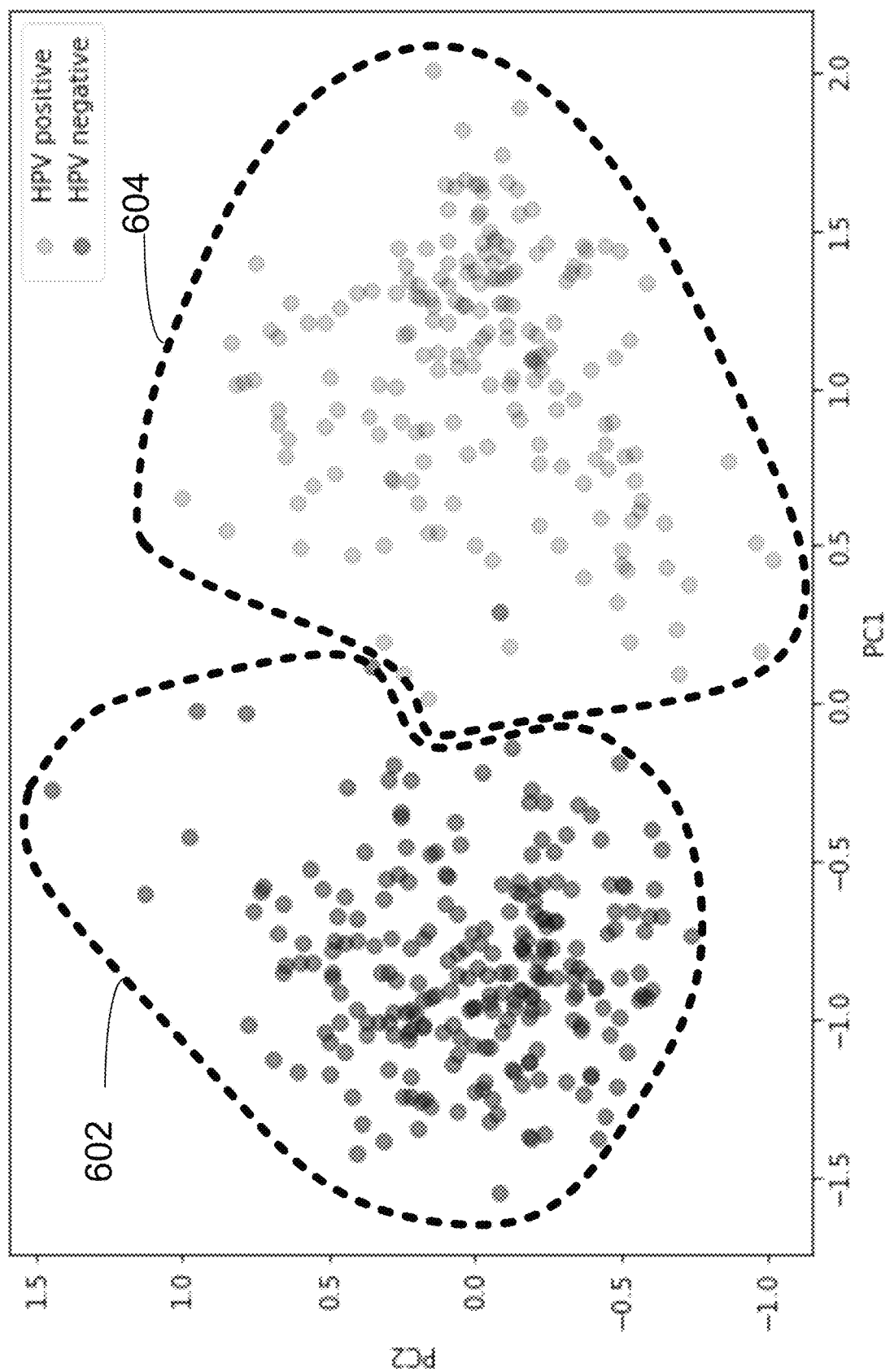

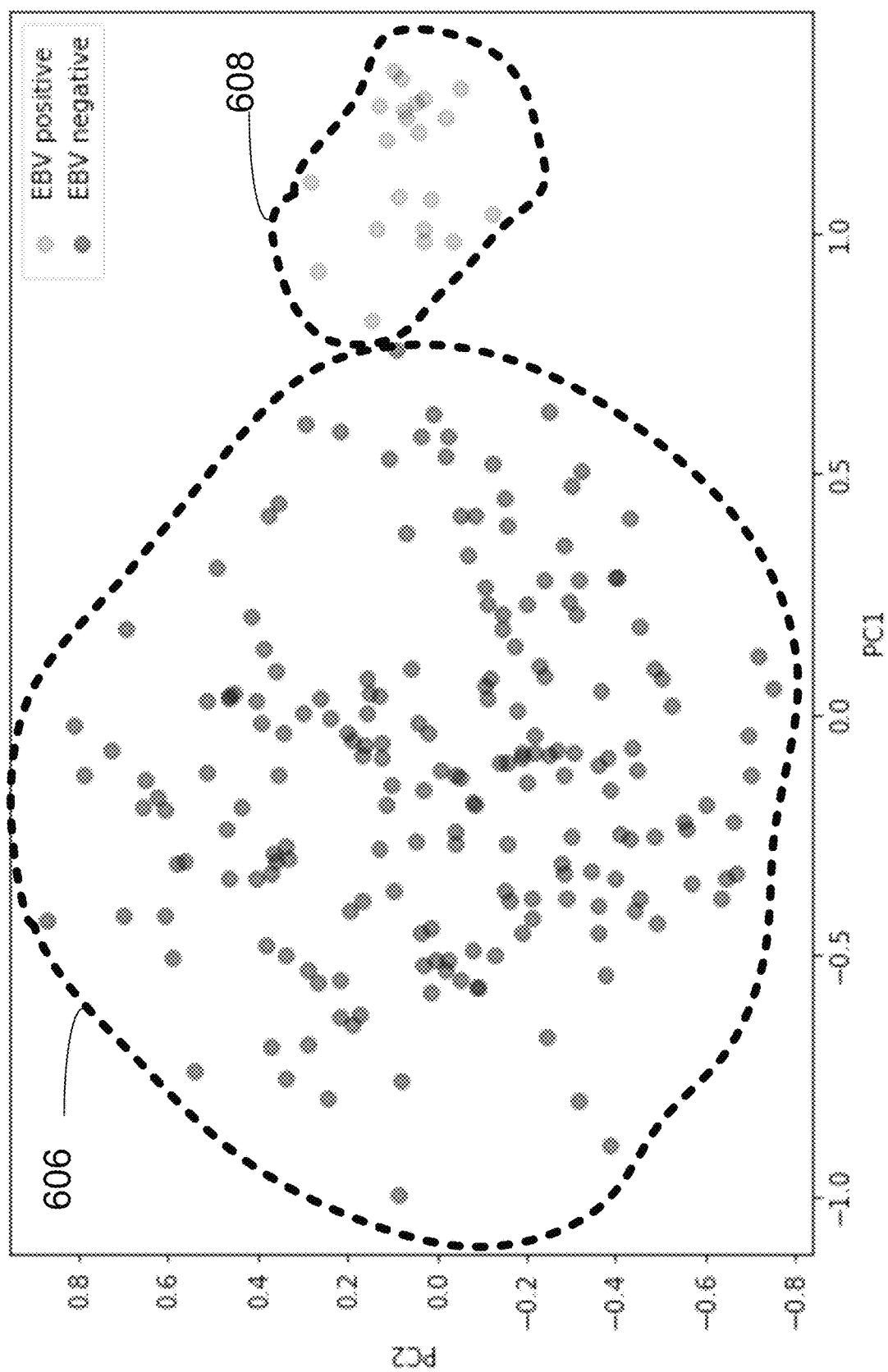

SYSTEMS AND METHODS FOR USING SEQUENCING DATA FOR PATHOGEN DETECTION

CROSS REFERENCE TO RELATED APPLICATIONS

This application claims priority to U.S. Provisional Patent Application No. 62/810,849, filed Feb. 26, 2019, the contents of which are hereby incorporated by reference in their entireties for all purposes.

TECHNICAL FIELD

The present disclosure relates generally to using expression profiles from cancerous tissue to detect oncogenic pathogenic infections in cancer patients.

BACKGROUND

Precision oncology is the practice of tailoring cancer therapy to a particular individual, e.g., accounting for the unique pathology, genomic, epigenetic, and/or transcriptomic profile of an individual tumor. By contrast, conventional cancer treatments are based merely on the type of cancer being treated. For example, conventionally, all breast cancers would be treated with a first therapeutic regimen while all lung cancers would be treated with a second therapeutic regimen. Precision oncology was borne out of many observations that different patients diagnosed with the same type of cancer, e.g., breast cancer, responded very differently to the same treatment regimen. Over time, researchers have identified genomic, epigenetic, and transcriptomic markers that facilitate some level of prediction as to how an individual cancer will respond to a particular treatment modality.

The use of targeted therapies has provided significant improvements in cancer patient outcomes, especially in terms of progression-free survival. Radovich et al., Oncotarget, 7:56491-500 (2016). Recent evidence reported from the IMPACT trial, which involved genetic testing of advanced stage tumors from 3,743 patients and where approximately 19% of patients received matched targeted therapies based on their tumor biology, showed a response rate of 16.2% in patients with matched treatments versus 5.2% in patients with non-matched treatments. Bankhead, "IMPACT Trial: Support for Targeted Cancer Tx Approaches," MedPageToday, Jun. 5, 2018. The IMPACT study also found that three-year overall survival rates for patients given a molecularly matched therapy was more than twice that of non-matched patients (15% vs. 7%). Id.; ASCO Post, "2018 ASCO: IMPACT Trial Matches Treatment to Genetic Changes in the Tumor to Improve Survival Across Multiple Cancer conditions," The ASCO POST, Jun. 6, 2018. Estimates of the proportion of patients for whom genetic testing changes the trajectory of their care vary widely, from approximately 10% to more than 50%. Fernandes et al., Clinics, 72:588-94 (2017).

Therapy targeted to specific genomic alterations is already the standard of care in several tumor types, e.g., as suggested in the National Comprehensive Cancer Network (NCCN) guidelines for melanoma, colorectal cancer, and non-small cell lung cancer. The few, well known mutations in the NCCN guidelines can be identified in cancer patients using individual assays or small next generation sequencing (NGS) panels. However, for the largest number of cancer patients to benefit from personalized oncology, more comprehensive pathologic, genomic, epigenetic, and/or transcriptomic analysis is necessary to facilitate the use of off-label drug indications, combination therapy, or tissue agnostic immunotherapy. Schwaederle et al., JAMA Oncol., 2:1452-59 (2016); Schwaederle et al., J Clin Oncol., 32:3817-25 (2015); and Wheler et al., Cancer Res., 76:3690-701 (2016).

The presence of oncogenic pathogen infections, account for 10 to 12% of all cancers. For example, gastric cancer is the third most common cause of cancer death worldwide, with more than 700,000 deaths estimated attributed to gastric cancer in 2012. Ferlay, et al., "Cancer Incidence and Mortality Worldwide," IARC CancerBase 11 [Internet], Lyon, France: International Agency for Research on Cancer (2013). In addition to genetic factors, gastric carcinogenesis is thought to be associated with multiple environmental factors, including Epstein-Barr virus (EBV) infection. Burke et al., Mod Pathol., 3:377-380 (1990). In fact, recent cancer genome atlas research has provided a molecular classification defining EBV-positive gastric cancer as a specific subtype. Cancer Genome Atlas Research Network, Nature, 513(7517):202-09 (2014).

As such, the presence of such oncogenic pathogens affects the prognosis of the associated cancer. Accordingly, when a subject has a type of cancer that is known to frequently arise in conjunction with an oncogenic pathogen, knowledge of the pathogen status of the subject is important to have because may change the treatment options of the subject. For example, numerous clinical trials investigating the benefit of radiation or chemotherapy dose reduction for HPV positive head and neck cancers have shown promising results. Additionally, pathogen-associated tumors are more likely to present higher levels of inflammation and immune infiltration, which make them good candidates for immunotherapy.

A drawback with conventional oncogenic pathogen diagnosis is that, in order to determine whether a subject is inflicted with a particular pathogen, a completely independent assay is performed separate and apart from the assays that were used to diagnose a subject with cancer in the first instance, or used to evaluate a stage of the cancer. For example, in the case of EBV, separate laboratory methods such as in situ hybridization (ISH) or polymerase chain reaction (PCR) for resected tissue, biopsy, or blood, or enzyme-linked immunosorbent assay (ELISA) or immunofluorescence assay (IFA) for serum samples is performed to detect the EBV infection. This is unsatisfactory because it increases the expense of diagnosis and, in some instances, where the pathogen test is only run after a type of cancer that is known to be associated with oncogenic pathogen has been diagnosed, delays the development of a treatment plan for the subject until the pathogen assay results have been obtained.

SUMMARY

Given the above background, what is needed in the art are improved systems and methods for pathogen detection that directly determine the presence of a given pathogen detection without a requirement for a separate independent assay for the pathogen detection.

Accordingly, improved methods for distinguishing cancers associated with oncogenic pathogen infections that contribute to the cancer pathology and cancers that are not associated with oncogenic pathogen infections are provided. Improved methods for treating cancer patients, based on whether their cancer is associated with an oncogenic pathogen infection, are also provided. The present disclosure addresses these needs, for example, by providing methods for identifying sets of genes that are differentially expressed in cancers that are associated with an oncogenic pathogen infection than in cancers that are not associated with an oncogenic pathogen infection. The disclosure also provides methods for training classifiers to distinguish between cancers associated with an oncogenic pathogen infection and cancers that are not associated with an oncogenic pathogen infection based on the identified genes that are differentially-regulated in the two types of cancer. Accordingly, methods for classifying cancer in patients as either being associated with an oncogenic pathogen infection or not associated with an oncogenic pathogen infection, using the trained classifiers, are also provided. These methods, in turn, allow for the differential treatment of patients based on whether or not their cancer is associated with an oncogenic pathogen infection.

One aspect of the present disclosure provides methods for training a classifier to discriminate between a first cancer condition and a second cancer condition, where the first cancer condition is associated with infection by a first oncogenic pathogen and the second cancer condition is associated with an oncogenic pathogen free status. The method includes, at a computer, obtaining a dataset that includes, for each respective subject in a plurality of subjects of a species: (i) a corresponding plurality of abundance values, wherein each respective abundance value in the corresponding plurality of abundance values quantifies a level of expression of a corresponding gene, in a plurality of genes, in a tumor sample of the respective subject, and (ii) an indication of cancer condition of the respective subject, where the indication of cancer condition identifies whether the respective subject has the first cancer condition or the second cancer condition, and wherein the plurality of subjects includes a first subset of subjects that are afflicted with the first cancer condition and a second subset of subjects that are afflicted with the second condition.

The method then includes identifying a discriminating gene set using the corresponding plurality of abundance values and respective indication of the cancer condition of respective subjects in the plurality of subjects, where the discriminating gene set includes a subset of the plurality of genes.

In some embodiments, the identifying the discriminating gene set comprises regressing the dataset based on all or a subset of the plurality of abundance values across the plurality of subjects against the respective indication of cancer condition across the plurality of subjects using a regression algorithm to thereby assign a corresponding regression coefficient, in a plurality of regression coefficients, to each respective gene in the plurality of genes, and selecting those genes in the plurality of genes for the discriminating gene set that are assigned a coefficient by the regression algorithm that satisfies a coefficient threshold.

In some alternative embodiments, the identifying the discriminating gene set comprises splitting the dataset into a plurality of sets, where each set in the plurality of sets includes two or more subjects that are afflicted with the first cancer condition and two or more subjects that are afflicted with the second condition, independently regressing each respective set in the plurality of sets based on all or a subset of the plurality of abundance values across the subjects of the respective set against the respective indication of cancer condition across the subject of the respective set using a regression algorithm to thereby assign a corresponding regression coefficient, in a plurality of regression coefficients, to each respective gene in the plurality of genes, and selecting those genes in the plurality of genes for the discriminating gene set that are assigned a coefficient by the regression algorithm that satisfies a coefficient threshold for at least a threshold percentage of the plurality of sets. In some embodiments, the plurality of sets consists of between five and fifty sets (e.g., ten sets).

In some embodiments, the coefficient threshold is zero. the coefficient threshold is satisfied when the absolute value of the corresponding regression coefficient is greater than zero.

In some embodiments, the above-disclosed regression algorithm is logistic regression. In some such embodiments, the logistic regression assumes:

$$P(Y=1 \mid x_i) = \frac{\exp(\beta_0 + \beta_1 x_{i1} + \ldots + \beta_k x_{ik})}{1 + \exp(\beta_0 + \beta_1 x_{i1} + \ldots + \beta_k x_{ik})},$$

where $x_i = (x_{i1}, x_{i2}, \ldots, x_{ik})$ are the corresponding plurality of abundance values for the plurality of genes from the tumor sample of the $i^{th}$ corresponding subject, $Y \in \{0, 1\}$ is a class label that has the value "1" when the corresponding subject i has the first cancer condition and has the value "0" when the corresponding subject i has the second cancer condition, where $P(Y=1|x_i)$ is the estimated probability that the $i^{th}$ corresponding subject is a member of the first cancer class. Further, $\beta_0$ is an intercept, and $\beta_j = (j=1, \ldots k)$ is the plurality of regression coefficients, where each respective regression coefficient in the plurality of regression coefficients is for a corresponding gene in the plurality of genes. In such embodiments, the $i^{th}$ corresponding subject is assigned to the first cancer class when $P(Y=1|x_i)$ exceeds a predefined threshold value (0.5) and to the second cancer class otherwise.

In some embodiments, the logistic regression is logistic least absolute shrinkage and selection operator (LASSO) regression. In such embodiments, the logistic LASSO estimator $\widehat{\beta_0}, \ldots, \widehat{\beta_k}$ is defined as the minimizer of the negative log likelihood:

$$\min(\Sigma_{i=1}^{n}[-y_i(\beta_0 + \beta_1 x_i + \ldots + \beta_k x_{ik}) + \log(1 + \exp(\beta_0 + \beta_1 x_i + \ldots + \beta_k x_{ik}))]),$$

subject to the constraint $\Sigma_{j=1}^{k} |\beta_j| \leq \lambda$.

In some embodiments, the regression algorithm is logistic regression with L1 or L2 regularization.

The method further includes using the respective abundance values for the discriminating gene set and the respective indication of cancer condition across the plurality of subjects to train a classifier (e.g., a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm) to discriminate between the first cancer condition and the second cancer condition as a function of respective abundance values for the discriminating gene set.

Another aspect of the present disclosure provides methods for discriminating between a first cancer condition and a second cancer condition in a subject, where the first cancer condition is associated with infection by a first oncogenic pathogen and the second cancer condition is associated with an oncogenic pathogen-free status. The method includes obtaining a dataset for the subject, the dataset including a plurality of abundance values, where each respective abundance value in the plurality abundance value quantifies a level of expression of a corresponding gene, in a plurality of genes, in a cancerous tissue from the subject. The method then includes inputting the dataset to a classifier trained according to the any one of the methodologies described herein.

Another aspect of the present disclosure provides nucleic acid probes for discriminating between a first cancer condition and a second cancer condition in a human subject, where the first cancer condition is associated with an oncogenic pathogen infection and the second cancer condition is associated with an oncogenic pathogen-free status. The nucleic acid probes have nucleic acid sequences that are complementary or identical to sequences of the genes identified as differentially expressed in cancers associated with an oncogenic pathogen infection.

Another aspect of the present disclosure provides a method for discriminating between a first cancer condition and a second cancer condition in a subject with a first type of cancer, where the first cancer condition is associated with infection by a first oncogenic pathogen and the second cancer condition is associated with an oncogenic pathogen-free status. The method includes obtaining a dataset for the subject, the dataset having a plurality of abundance values (e.g., relative mRNA expression values), where each respective abundance value in the plurality of abundance values quantifies a level of expression of a corresponding gene, in a discriminating gene set, in a cancerous tissue from the subject. The method then includes inputting the dataset to a classifier trained to discriminate between at least the first cancer condition and the second cancer condition based on abundance values for the discriminating gene set in a cancerous tissue of a subject, thereby determining the cancer condition of the subject.

In some embodiments, the first type of cancer is breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer.

In some embodiments, the dataset further includes a variant allele count for one or more variant alleles at one or more locus in the genome of the cancerous tissue from the subject.

In some embodiments, the first cancer condition is associated with infection by a first oncogenic pathogen selected from the group consisting of Epstein-Barr virus (EBV), hepatitis B virus (HBV), hepatitis C virus (HCV), human papilloma virus (HPV), human T-cell lymphotropic virus (HTLV-1), Kaposi's associated sarcoma virus (KSHV), and Merkel cell polyomavirus (MCV).

In some embodiments, the first cancer condition is selected from the group consisting of cervical cancer associated with human papilloma virus (HPV), head and neck cancer associated with HPV, gastric cancer associated with Epstein-Barr virus (EBV), nasopharyngeal cancer associated with EBV, Burkitt lymphoma associated with EBV, Hodgkin lymphoma associated with EBV, liver cancer associated with hepatitis B virus (HBV), liver cancer associated with hepatitis C virus (HCV), Kaposi sarcoma associated with Kaposi's associated sarcoma virus (KSHV), adult T-cell leukemia/lymphoma associated with human T-cell lymphotropic virus (HTLV-1), and Merkel cell carcinoma associated with Merkel cell polyomavirus (MCV).

In some embodiments, the first cancer condition is associated with infection by a human papillomavirus (HPV) oncogenic virus and the second cancer condition is associated with an HPV-free status, and the discriminating gene set includes at least five genes selected from the genes listed in Table 3. In some embodiments, the first cancer condition is cervical cancer associated with infection by a human papillomavirus (HPV). In some embodiments, the first cancer condition is head and neck cancer associated with infection by a human papillomavirus (HPV). In some embodiments, the discriminating gene set includes at least ten genes selected from the genes listed in Table 3. In some embodiments, the discriminating gene set includes at least twenty genes selected from the genes listed in Table 3. In some embodiments, the discriminating gene set includes at least all twenty-four of the genes listed in Table 3. In some embodiments, the dataset also includes a variant allele count for TP53 (ENSG00000141510) and CDKN2A (ENSG00000147889) in the genome of the cancerous tissue from the subject.

In some embodiments, the method also includes treating the subject for cervical cancer by, when the classifier result indicates that the human cancer patient is infected with an HPV oncogenic virus, administering a first therapy tailored for treatment of cervical cancer associated with an HPV infection, and when the classifier result indicates that the human cancer patient is not infected with an HPV oncogenic virus, administering a second therapy tailored for treatment of cervical cancer not associated with an HPV infection. In some embodiments, the first therapy tailored for treatment of cervical cancer associated with an HPV infection includes a therapeutic vaccine or an adoptive cell therapy. In some embodiments, the second therapy tailored for treatment of cervical cancer not associated with an HPV infection is chemotherapy. In some embodiments, the chemotherapy includes co-administration of cisplatin and a second therapeutic agent selected from the group consisting of 5-fluorouracil, paclitaxel, and bevacizumab.

In some embodiments, the method also includes treating the subject for head and neck cancer by, when the classifier result indicates that the human cancer patient is infected with an HPV oncogenic virus, administering a first therapy tailored for treatment of head and neck cancer associated with an HPV infection, and when the classifier result indicates that the human cancer patient is not infected with an HPV oncogenic virus, administering a second therapy tailored for treatment of head and neck cancer not associated with an HPV infection. In some embodiments, the first therapy tailored for treatment of head and neck cancer associated with an HPV infection includes a therapeutic vaccine, an immune checkpoint inhibitor, or a PI3K inhibitor. In some embodiments, the second therapy tailored for treatment of head and neck cancer not associated with an HPV infection includes chemotherapy. In some embodiments, the chemotherapy includes administration of cisplatin, and the second therapy also includes concurrent radiotherapy or postoperative chemoradiation.

In some embodiments, the first cancer condition is associated with infection by an Epstein-Barr virus (EBV) oncogenic virus and the second cancer condition is associated with an EBV-free status, and the discriminating gene set includes at least five genes selected from the genes listed in Table 4. In some embodiments, the first cancer condition is gastric cancer associated with infection by an Epstein-Barr virus (EBV). In some embodiments, the discriminating gene set includes all nine genes listed in Table 4. In some embodiments, the dataset also includes a variant allele count for TP53 (ENSG00000141510) and PIK3CA (ENSG00000121879) in the genome of the cancerous tissue from the subject.

In some embodiments, the method also includes treating the subject for gastric cancer by, when the classifier result indicates that the human cancer patient is infected with an EBV oncogenic virus, administering a first therapy tailored for treatment of gastric cancer associated with an EBV infection, and when the classifier result indicates that the human cancer patient is not infected with an EBV oncogenic virus, administering a second therapy tailored for treatment of gastric cancer not associated with an EBV infection. In some embodiments, the first therapy tailored for treatment of gastric cancer associated with an EBV infection includes an immune checkpoint inhibitor. In some embodiments, the second therapy tailored for treatment of gastric cancer not associated with an EBV infection includes chemotherapy. In some embodiments, the chemotherapy includes administration of a therapeutic agent selected from the group consisting of paclitaxel, carboplatin, cisplatin, 5-fluorouracil, and oxaliplatin.

In some embodiments, the method also includes treating the subject for cancer by, when the classifier result indicates that the human cancer patient is infected with the first oncogenic pathogen, administering a first therapy tailored for treatment of the first type of cancer associated with infection by the first oncogenic pathogen, and when the classifier result indicates that the human cancer patient is not infected with the first oncogenic pathogen, administering a second therapy tailored for treatment of the first type of cancer associated with an oncogenic pathogen-free status.

In some embodiments, the classifier was trained by a method including (1) obtaining a dataset comprising, for each respective subject in a plurality of subjects of a species: (i) a corresponding plurality of abundance values, wherein each respective abundance value in the corresponding plurality of abundance values quantifies a level of expression of a corresponding gene, in a plurality of genes, in a tumor sample of the respective subject, and (ii) an indication of cancer condition of the respective subject, wherein the indication of cancer condition identifies whether the respective subject has the first cancer condition or the second cancer condition, and wherein the plurality of subjects includes a first subset of subjects that are afflicted with the first cancer condition and a second subset of subjects that are afflicted with the second condition; (2) identifying the discriminating gene set using the corresponding plurality of abundance values and respective indication of the cancer condition of respective subjects in the plurality of subjects, wherein the discriminating gene set comprises a subset of the plurality of genes; and (3) using the respective abundance values for the discriminating gene set and the respective indication of cancer condition across the plurality of subjects to train a classifier to discriminate between the first cancer condition and the second cancer condition as a function of respective abundance values for the discriminating gene set.

Other embodiments are directed to systems, portable consumer devices, and computer readable media associated with the methods described herein.

As disclosed herein, any embodiment disclosed herein when applicable can be applied to any aspect.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 2A, 2B, 2C, 2D, and 2E collectively provide a flow chart of processes and features for training a classifier to discriminate between a first cancer condition associated with infection by a first oncogenic pathogen and a second cancer condition associated with an oncogenic pathogen-free status, in which optional blocks are indicated with dashed boxes, in accordance with some embodiments of the present disclosure.

FIG. 4A provides a breakdown of the compositions of the TGCA training and the testing datasets for training a classifier to discriminate between a first cancer condition associated with an HPV oncogenic viral infection and a second cancer condition not associated with an HPV oncogenic viral infection, in accordance with some embodiments of the present disclosure.

FIG. 4B illustrates features of a cancerous tissue that are useful for discriminating between a first cancer condition associated with an HPV oncogenic viral infection and a second cancer condition not associated with an HPV oncogenic viral infection, in accordance with some embodiments of the present disclosure.

FIG. 4D illustrates performance metrics for a trained support vector machine, against a validation dataset, for discriminating between a first cancer condition associated with an HPV oncogenic viral infection and a second cancer condition not associated with an HPV oncogenic viral infection, in accordance with some embodiments of the present disclosure.

FIG. 5A provides a breakdown of the compositions of the TGCA training and the testing datasets for training a classifier to discriminate between a first cancer condition associated with an EBV oncogenic viral infection and a second cancer condition not associated with an EBV oncogenic viral infection, in accordance with some embodiments of the present disclosure.

FIG. 5B illustrates features of a cancerous tissue that are useful for discriminating between a first cancer condition associated with an EBV oncogenic viral infection and a second cancer condition not associated with an HPV oncogenic viral infection, in accordance with some embodiments of the present disclosure.

FIG. 6A illustrates principal component analysis of expression features of the genes identified in Example 3 to be differentially expressed in head and neck and cervical cancers associated with an HPV viral infection, in tissue samples of head and neck and cervical cancers, in accordance with some embodiments of the present disclosure.

FIG. 6B illustrates principal component analysis of expression features of genes identified in Example 4 to be differentially expressed in gastric cancers associated with an EBV viral infection, in tissue samples of head and neck and cervical cancers, in accordance with some embodiments of the present disclosure.

Like reference numerals refer to corresponding parts throughout the several views of the drawings.

DETAILED DESCRIPTION

Figure 1A:
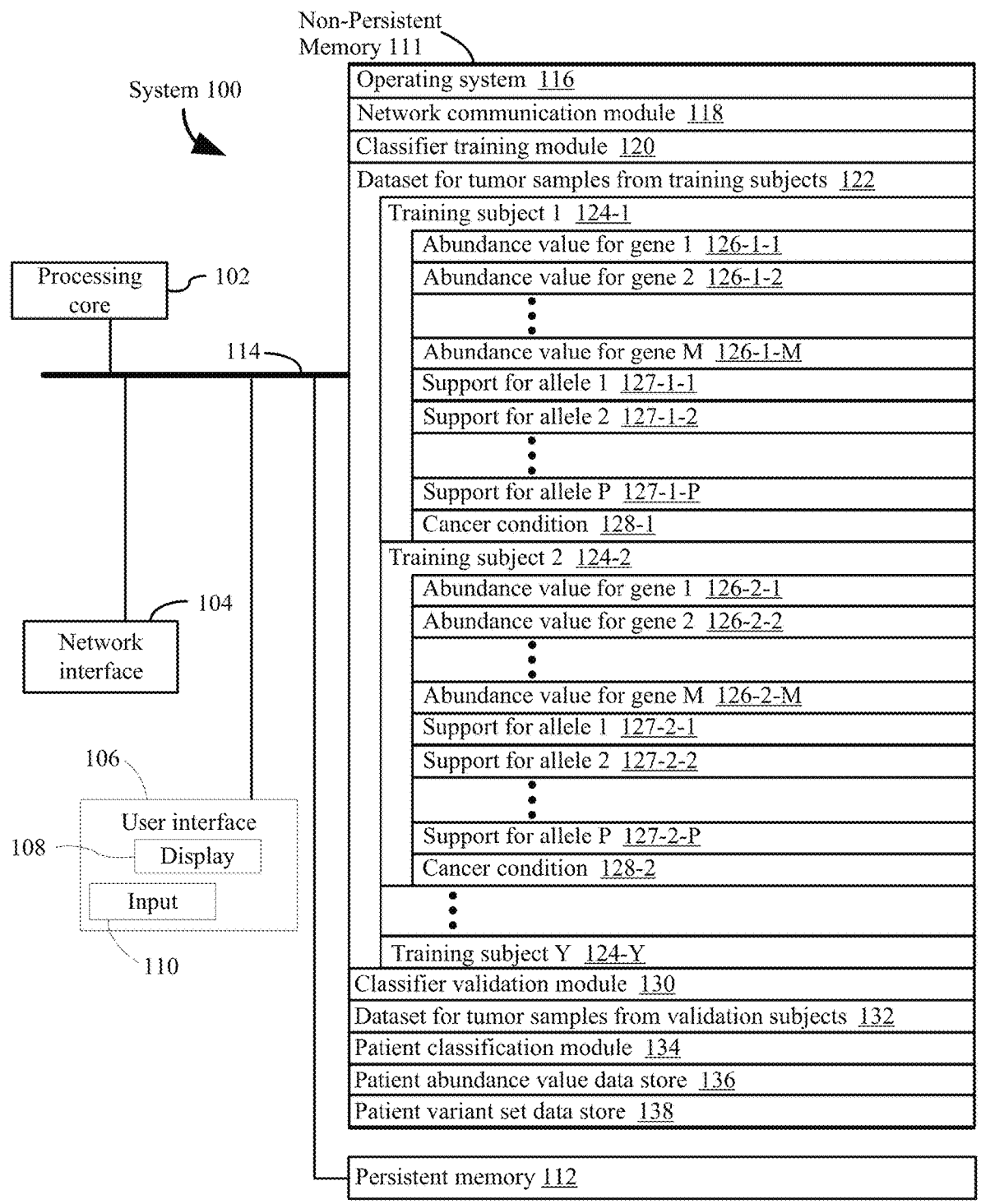
FIGS. 1A and 1B collectively illustrate a block diagram of an example computing device, in accordance with some embodiments of the present disclosure.

The present disclosure provides systems and methods useful for distinguishing cancers associated with oncogenic pathogen infections that contribute to the cancer pathology from cancers that are not associated with oncogenic pathogen infections. The present disclosure further provides systems and methods useful for treating cancer patients, based on whether their cancer is associated with an oncogenic pathogen infection or not.

Advantageously, the systems and methods described herein allow for oncogenic pathogen detection in cancers, without the need for additional diagnostic assays. Surprisingly, it was found that oncogenic pathogen infections could be identified based on mRNA expression levels in a tumor biopsy. As such, additional assays developed to identify nucleic acids or protein components of these pathogens are rendered unnecessary by the present disclosure. Rather, a single mRNA expression analysis can be performed to both characterize the transcriptional profile of the cancer and determine whether it is associated with an oncogenic pathogen infection. For instance, as reported in Example 3, a support vector machine classifier trained against only mRNA expression data and two allele statuses identified HPV infection in head and neck and cervical cancers with 99% specificity and 99% sensitivity. Similarly, as reported in Example 4, a support vector machine classifier trained against only mRNA expression data and two allele statuses identified EBV infection in gastric cancer with 99% specificity and 95% sensitivity.

For example, in one aspect, the present disclosure provides methods for training a classifier to discriminate between first and second cancer conditions, where the first cancer condition is associated with infection by a first oncogenic pathogen and the second cancer condition is associated with an oncogenic pathogen-free status. In accordance with the method, with reference to FIG. 4A, a dataset is obtained that has a corresponding plurality of abundance values for each respective subject in a plurality of subjects of a species. Each respective abundance value quantifies a level of expression of a corresponding gene, in a plurality of genes, in a tumor sample of the respective subject. The dataset further comprises an indication of cancer condition of each respective subject tracked by the dataset. The indication of cancer condition identifies whether a subject has the first or second cancer condition (e.g., HPV positive head and neck or cervical cancer, or HPV negative head and neck or cervical cancer as illustrated in FIG. 4A).

In some embodiments, each of the subjects has a particular cancer with the same origin (e.g., gastric cancer as illustrated in FIG. 5A) and what delineates whether the subject is in the first cancer class or the second cancer class is whether or not the subject also is afflicted with an oncogenic pathogen (e.g., EBV virus in the case of FIG. 5A) that is known to associate with this cancer such that the prognosis of those subjects with the cancer that are also afflicted with the oncogenic pathogen is different than the prognosis of those subjects with the cancer that are not afflicted with the oncogenic pathogen. Some of the subjects tracked by the dataset (a first subset of subjects) are afflicted with the first cancer condition while some of the subject tracked by the dataset (a second subset of subjects) are afflicted with the second condition. Next, a discriminating gene set is identified using the corresponding plurality of abundance values and respective indication of the cancer condition of respective subjects in the plurality of subjects. The discriminating gene set comprises a subset of the plurality of genes. In general, the abundance levels (e.g., expression) of such genes discriminates between the first and second cancer conditions. Details regarding the discriminating gene set are disclosed below with reference to block 218 of FIG. 2C. FIG. 4B illustrates a discriminating gene set for HPV associated cancers (head and neck cancers and cervical cancers) while FIG. 5B illustrates a discriminating gene set for EBV associated cancer (gastric cancer)

The respective abundance values for the discriminating gene set and the respective indication of cancer condition across the plurality of subjects is used to train a classifier to discriminate between the first and second cancer conditions as a function of respective abundance values for the discriminating gene set. In some optional embodiments, the trained classifier is used to classify a test subject to the first cancer or to the second condition (or determine a likelihood that the test subject has the first or second cancer condition) by inputting a test plurality of abundance values into the trained classifier. In such embodiments, each respective abundance value in the test plurality of abundance values quantifies a level of expression of a corresponding gene, in the plurality of genes, in a tumor sample of the test subject. In some optional embodiments the result of the trained classifier is used to provide a therapeutic intervention or imaging of the test subject based on a determination that the test subject has the first cancer condition or the second cancer condition (or likelihood that the test subject has the first or second cancer condition).

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "subject" refers to any living or non-living organism, including but not limited to a human (e.g., a male human, female human, fetus, pregnant female, child, or the like), a non-human mammal, or a non-human animal. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, a subject is a male or female of any stage (e.g., a man, a women or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, i.e., on a particular chromosome. In some embodiments, a locus refers to a single nucleotide position within a genome, i.e., on a particular chromosome. In some embodiments, a locus refers to a small group of nucleotide positions within a genome, e.g., as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, i.e., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation" or "variant" refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein the term "cancer," "cancerous tissue," or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein.

As used herein, a "cancer condition associated with an oncogenic pathogen infection," either generically or with reference to a specific oncogenic pathogen, refers to the condition in which a cancer subject, afflicted with a specific cancer, is further afflicted with a pathogen (e.g., virus) known to associate with the specific cancer.

As used herein, a "cancer condition that is not associated with an on oncogenic pathogen infection," either generically or with reference to a specific oncogenic pathogen, refers to the condition in which a cancer subject, afflicted with a specific cancer, is specifically not afflicted with a pathogen (e.g., virus) known to associate with the specific cancer.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term "read-depth," "sequencing depth," or "depth" refers to a total number of read segments from a sample obtained from an individual at a given position, region, or locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence read. In some embodiments, the depth refers to the average sequencing depth across the genome, across the exome, or across a targeted sequencing panel. Sequencing depth can also be applied to multiple loci, the whole genome, in which case Y can refer to the mean number of times a loci or a haploid genome, a whole genome, or a whole exome, respectively, is sequenced. When a mean depth is quoted, the actual depth for different loci included in the dataset can span over a range of values. Ultra-deep sequencing can refer to at least 100× in sequencing depth at a locus.

As used herein the term "sequencing breadth" refers to what fraction of a particular reference exome (e.g., human reference exome), a particular reference genome (e.g., human reference genome), or part of the exome or genome has been analyzed. The denominator of the fraction can be a repeat-masked genome, and thus 100% can correspond to all of the reference genome minus the masked parts. A repeat-masked exome or genome can refer to an exome or genome in which sequence repeats are masked (e.g., sequence reads align to unmasked portions of the exome or genome). Any parts of an exome or genome can be masked, and thus one can focus on any particular part of a reference exome or genome. Broad sequencing can refer to sequencing and analyzing at least 0.1% of the exome or genome.

As used herein, the term, "reference exome" refers to any particular known, sequenced or characterized exome, whether partial or complete, of any tissue from any organism or pathogen that may be used to reference identified sequences from a subject. Exemplary reference exomes used for human subjects, as well as many other organisms, are provided in Examples 1 and 2.

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes.

Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an oncogenic pathogen infection status, an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the term "relative abundance" can refer to a ratio of a first amount of nucleic acid fragments having a particular characteristic (e.g., aligning to a particular region of the exome) to a second amount of nucleic acid fragments having a particular characteristic (e.g., aligning to a particular region of the exome). In one example, relative abundance may refer to a ratio of the number of mRNA transcripts encoding a particular gene in a sample (e.g., aligning to a particular region of the exome) to the total number of mRNA transcripts in the sample.

As used herein the term "untrained classifier" refers to a classifier that has not been trained on a training dataset.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art.

Several factors are typically taken into account when determining an appropriate dosage to achieve an effective amount. These factors include age, sex and weight of the subject, the condition being treated, the severity of the condition and the form and effective concentration of the therapeutic agent being administered.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments

Figure 1B:
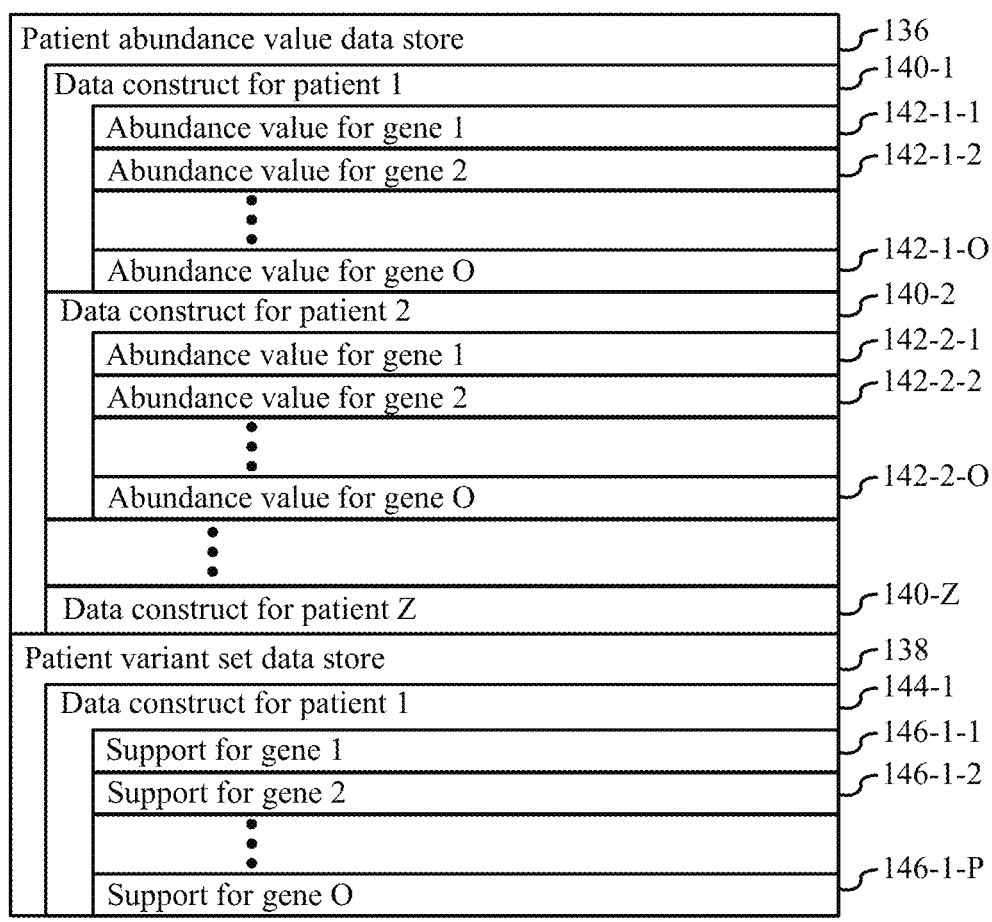

Now that an overview of some aspects of the present disclosure and some definitions used in the present disclosure have been provided, details of an exemplary system are now described in conjunction with FIG. 1. FIG. 1 is a block diagram illustrating a system 100 in accordance with some implementations. The device 100 in some implementations includes one or more processing units CPU(s) 102 (also referred to as processors), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices and/or a communication network 105;
- an optional classifier training module 120 for training classifiers that distinguish a first cancer condition, associated with an oncogenic pathogen infection, from a second cancer condition, that is not associated with an oncogenic pathogen infection;
- an optional data store for datasets for tumor samples from training subjects 122 including expression data from one or more training subjects 124, where the expression data includes a plurality of abundance data for each of a plurality of genes 126, support for a plurality of variant alleles for each of one or more genes 127, and a cancer condition 128;
- an optional classifier validation module 130 for validating classifiers that distinguish a first cancer condition, associated with an oncogenic pathogen infection, from a second cancer condition, that is not associated with an oncogenic pathogen infection;
- an optional data store for datasets for tumor samples from validation subjects including expression data from one or more training subjects, where the expression data includes a plurality of abundance data for each of a plurality of genes and a cancer condition;
- an optional patient classification module 134 for classifying a cancer in a patient as either a first cancer condition, associated with an oncogenic pathogen infection, or a second cancer condition, that is not associated with an oncogenic pathogen infection, using a classifier, e.g., as trained using classifier training module 120;
- an optional data store for data constructs for cancer patients 136 including expression data from one or more cancer patients 140, where the expression data includes a plurality of abundance data for each of a plurality of genes 142; and
- an optional data store for data constructs for cancer patients 138 including variant allele data from one or more cancer patients 144, where the variant allele data includes a plurality of support for variant alleles for each of one or more genes 146.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Classifier Training.

While a system in accordance with the present disclosure has been disclosed with reference to FIG. 1, an overview of methods in accordance with the present disclosure are provided in conjunction with FIG. 2A. In block 204 of FIG. 2A, a dataset is obtained. The dataset comprises a corresponding plurality of abundance values for each respective subject in a plurality of subjects of a species. Each respective abundance value quantifies a level of expression of a corresponding gene, in a plurality of genes, in a tumor sample of the respective subject. The dataset further comprises an indication of cancer condition of each respective subject tracked by the dataset. The indication of cancer condition identifies whether a subject has the first or second cancer condition.

In some embodiments, each of the subjects has a particular cancer with the same origin (e.g., stomach cancer) and what delineates whether the subject is in the first cancer class or the second cancer class is whether or not the subject also is afflicted with an oncogenic pathogen that is known to associate with this cancer such that the prognosis of those subjects with the cancer that are also afflicted with the oncogenic pathogen is different than the prognosis of those subjects with the cancer that are not afflicted with the oncogenic pathogen. For instance, in the case where the specific oncogenic pathogen is Epstein Barr virus (EBV), each of the subjects has a gastric cancer tumor and what determines whether a respective subject is in the first or second cancer class is whether the subject also is inflicted with EBV.

In some embodiments, each of the subjects has a cancer that is associated with a set of cancers and what delineates whether the subject is in the first cancer class or the second cancer class is whether or not the subject also is afflicted with an oncogenic pathogen that is known to associate with any of the respective cancers in this set of cancers such that the prognosis of those subjects with the respective cancer in the set of cancers are also afflicted with the oncogenic pathogen is different than the prognosis of those subjects with the respective cancer that are not afflicted with the oncogenic pathogen. For instance, in the case where the specific oncogenic pathogen is human papilloma virus (HPV), the set of cancers is head and neck squamous cell carcinoma and cervical cancer. That is, each subject has a head and neck squamous cell carcinoma or has cervical cancer and what determines whether a respective subject is in the first or second cancer class is whether the subject also is inflicted with HPV.

In some embodiments, each of the subjects has a cancer set forth in column 2 of the same row set forth in Table 1 below, and what delineates whether the subject is in the first cancer class or the second cancer class is whether or not the subject also is afflicted with the pathogen of column 1 of that same row in Table 1 below. See for example, Flora and Bonanni, Carcinogenesis 32(6), pp. 787-795, which is hereby incorporated by reference tract, a subset of which have been found to be oncogenic. For example, pathogens that have been hypothesized to cause, or are correlated with, colon or colorectal cancers include Sulfidogenic bacteria (e.g. *Fusobacterium, Desulfovibrio,* and *Bilophila wadsworthia*), *Streptococcus bovis,* and *Fusobacterium nucleatum.* For further information, see, Dahmus et al., 2018, J Gastrointest Oncol., 9(4), pp. 769-77, the content of which is hereby incorporated herein, in its entirety, for all purposes.

Some of the subjects tracked by the dataset (a first subset of subjects) are afflicted with the first cancer condition while some of the subject tracked by the dataset (a second subset of subjects) are afflicted with the second condition. More details regarding such datasets are disclosed below with reference to block 202 of FIG. 2B.

Figure 2C:
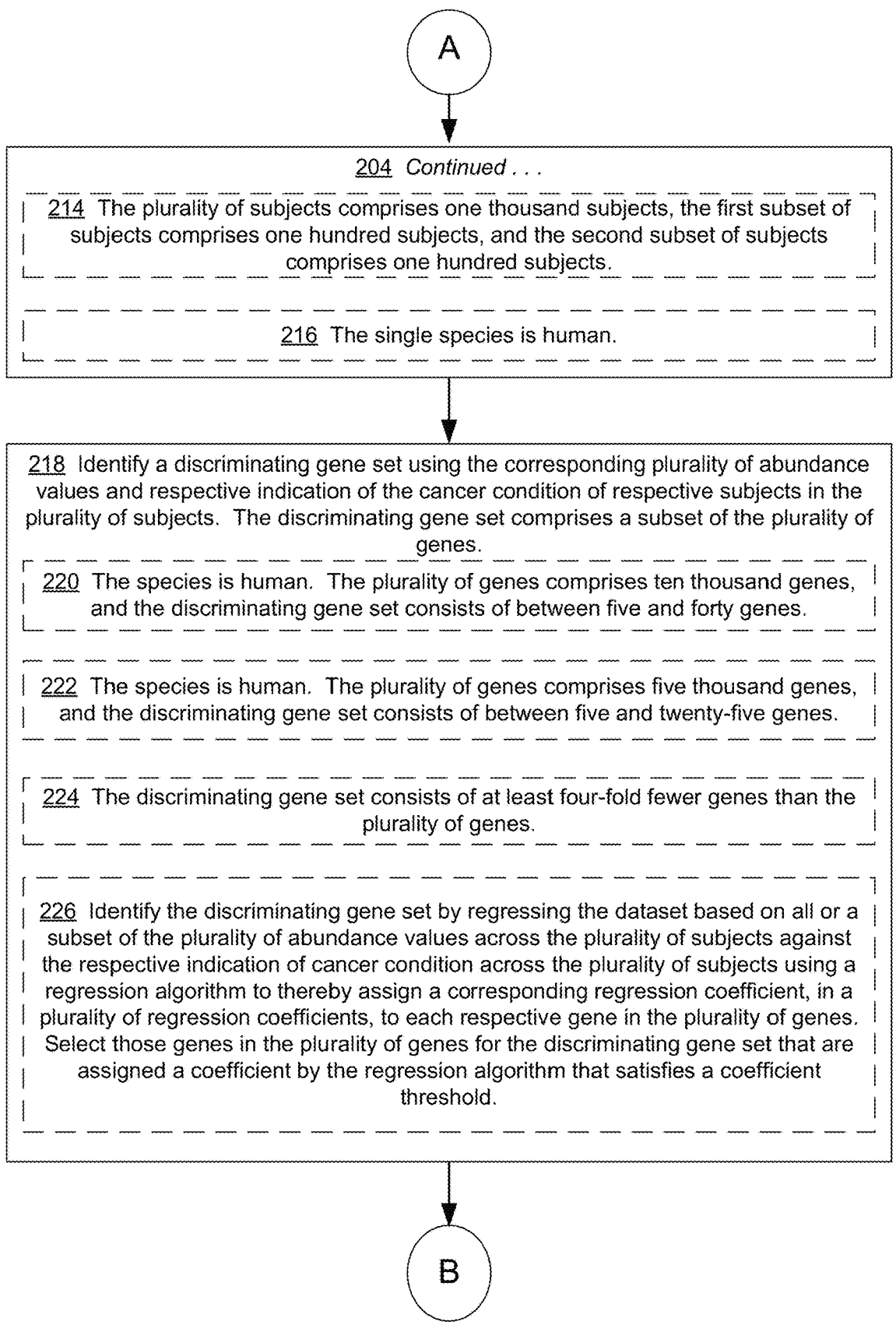

Next, in block 218 of FIG. 2A, a discriminating gene set is identified using the corresponding plurality of abundance values and respective indication of the cancer condition of respective subjects in the plurality of subjects. The discriminating gene set comprises a subset of the plurality of genes. In general, the abundance levels (e.g., expression) of such genes discriminates between the first and second cancer condition. More details regarding the discriminating gene set are disclosed below with reference to block 218 of FIG. 2C.

TABLE 1

Pathogen infections associated with cancer in humans.

| PATHOGEN (COLUMN 1) | ASSOCIATED CANCER (COLUMN 2) |
|---|---|
| Hepatitis virus - HBV | Hepatocellular carcinoma (HCC) |
| Hepatitis virus - HCV | Hepatocellular carcinoma (HCC) |
| Papillomaviruses (HPV) - (e.g., Alpha HPV types 16, 18, 26, 30, 31, 33, 34, 35, 39, 45, 51, 52, 53, 56, 58, 59, 66, 67, 68, 69, 70, 73, 82, 85, and 97) | Cervical cancer, Head and Neck Squamous Cell Carcinoma, ovarian cancer, penile cancer, pharyngeal cancer, anal cancer, vaginal cancer, sino-nasal cancer, and vulvar cancer |
| Papillomaviruses (HPV) - (e.g., Beta HPV types 5 and 8) | Skin Cancer |
| Polyomaviruses - (e.g., JCV) | CNS tumors |
| Merkel Cell Polyomavirus - (e.g., MCV) | Skin cancer, e.g., Merckel cell carcinoma |
| Polyomaviruses - (e.g., SV40) | Malignant mesothelioma |
| Herpesviruses (e.g., EBV or HHV4) | Burkitt's lymphoma, sinonasal angiocentric T-cell lymphoma, immunosuppressor-related non-Hodgkin's lymphoma, Hodgkin's lymphoma, nasopharyngeal carcinoma, Gastric Carcinoma |
| Herpesviruses (e.g., KSHV or HHV8) | Kaposi's sarcoma, primary effusion lymphoma |
| Retroviruses (e.g., HTLV-I) | Adult T-cell leukemia/lymphoma |
| Retroviruses (e.g., HIV-I) | Kaposi's sarcoma, non-Hodgkin's lymphoma, Hodgkin's lymphoma, cervical cancer, anus cancer, conjunctive cancer |
| Retroviruses (e.g., HIV-2) | Kaposi's sarcoma, non-Hodgkin's lymphoma |
| Retroviruses (e.g., HERV-K) | Human breast cancer |
| Retroviruses (e.g., XMRV) | Prostate cancer |
| *Helicobacter pylori* | Non-cardia gastric cancer, MALT lymphoma |
| *Streptococcus bovis* | Colorectal cancer |
| *Salmonella typhi* | Gallbladder cancer |
| *Bartonella* species | Vascular tumors |
| Human gut microbiome | Colon cancer |
| *Clamydophila pneumonia* | Lung cancer |
| *Schistosoma haematobium* | Urinary bladder cancer |
| *Schistosoma japonicum* | Colorectal and liver cancers |
| Liver fluke (e.g., *Opistorchis viverrini, Opistorchis sinensis*) | Cholangiocarcinoma |

As used herein, the term "human gut microbiome" refers to all of the microorganisms living in the human digestive Next, in block 242 of FIG. 2A, the respective abundance values for the discriminating gene set and the respective indication of cancer condition across the plurality of subjects is used to train a classifier to discriminate between the first and second cancer conditions as a function of respective abundance values for the discriminating gene set. More details regarding training such classifiers based on the discriminating gene set are disclosed below with reference to block 242 of FIG. 2E.

Further, with reference to block 246 of FIG. 2A, in some optional embodiments the trained classifier is used to classify a test subject to the first cancer or to the second condition (or determine a likelihood that the test subject has the first or second cancer condition) by inputting a test plurality of abundance values into the classifier. In such embodiments, each respective abundance value in the test plurality of abundance values quantifies a level of expression of a corresponding gene, in the plurality of genes, in a tumor sample of the test subject. The test subject is a subject whose test plurality of abundance values were not used to train the classifier. Moreover, in typical instances, a test subject is a subject for which it has not been confirmed whether the subject has the first or second cancer condition. More details regarding the diagnosis of a test subject using the classifier trained in accordance with the present disclosure are disclosed below with reference to block 246 of FIG. 2E.

Further, with reference to block 248 of FIG. 2A, in some optional embodiments the result of the trained classifier is used to provide a therapeutic intervention or imaging of the test subject based on a determination that the test subject has the first cancer condition or the second cancer condition (or likelihood that the test subject has the first or second cancer condition). More details regarding such treatment options that arise as a result of the application of the trained classifier against the abundance data of the plurality of test genes is disclosed below with reference to block 248 of FIG. 2E.

Now that an overview of the disclosed methods has been provided in conjunction with FIG. 2A, attention turns to FIGS. 2B through 2E, which provide further details regarding the disclosed methods.

Block 202.

Referring to block 202 of FIG. 2A, methods are provided for training a classifier to discriminate between a first cancer condition and a second cancer condition. As discussed above, the first cancer condition is associated with infection by a first oncogenic pathogen and the second cancer condition is associated with an oncogenic pathogen-free status. Non-limited examples of cancers known to be associated with oncogenic pathogen infections are described below, with reference to FIG. 3. Accordingly, in some embodiments, the first cancer condition is a particular type of cancer that is associated with a particular oncogenic pathogen infection, e.g., as described below, and the second cancer condition is the same particular type of cancer which is not associated with the particular oncogenic pathogen infection. For example, in one embodiment, the first cancer condition is cervical cancer associated with an HPV infection and the second cancer condition is cervical cancer that is not associated with a pathogen infection.

Block 204.

Referring to block 204 of FIG. 2A, a dataset is obtained that comprises a corresponding plurality of abundance values for each respective subject in a plurality of subjects of a single species. Each respective abundance value in the corresponding plurality of abundance values quantifies a level of expression of a corresponding gene, in a plurality of genes, in a tumor sample of the respective subject. The dataset further comprises an indication of cancer condition of the respective subject. The indication of cancer condition identifies whether the respective subject has the first or second cancer condition. The plurality of subjects includes a first subset of subjects that are afflicted with the first cancer condition and a second subset of subjects that are afflicted with the second condition.

Block 206.

Referring to block 206, in some embodiments, the corresponding plurality of abundance values is obtained by RNA-seq. RNA-seq is a methodology for RNA profiling based on next-generation sequencing that enables the measurement and comparison of gene expression patterns across a plurality of subjects. In some embodiments, millions of short strings, called 'sequence reads,' are generated from sequencing random positions of cDNA prepared from the input RNAs that are obtained from tumor tissue of a subject. These reads can then be computationally mapped on a reference genome to reveal a 'transcriptional map', where the number of sequence reads aligned to each gene gives a measure of its level of expression (e.g., abundance). Next-generation sequencing is disclosed in Shendure, 2008, "Next-generation DNA sequencing," Nat. Biotechnology 26, pp. 1135-1145, which is hereby incorporated by reference. RNA-seq is disclosed in Nagalakshmi et al., 2008, "The transcriptional landscape of the yeast genome defined by RNA sequencing," Science 320, pp. 1344-1349; and Finotell and Camillo, 2014, "Measuring differential gene expression with RNA-seq: challenges and strategies for data analysis," Briefings in Functional Genomics 14(2), pp. 130-142, each of which is hereby incorporated by reference.

In accordance with block 206, for each tumor sample for each subject in the plurality of subjects, The RNAs in the sample of interest are initially fragmented and reverse-transcribed into complementary DNAs (cDNAs). The obtained cDNAs are then amplified and subjected to next-generation DNA sequencing (NGS). In principle, any NGS technology can be used for RNA-seq. In some embodiments, the Illumina sequencer (see the Internet at illumina.com) is used. See, Wang, Z., et al., "RNA-Seq: a revolutionary tool for transcriptomics," Nat Rev Genet., 10(1):57-63 (2009), which is hereby incorporated by reference. The millions of short reads generated for each such sample are then mapped on a reference genome and the number of reads aligned to each gene, called 'counts', gives a digital measure of gene expression levels in the sample under investigation.

In some alternative embodiments, rather than using RNA-seq, microarrays are used to measure gene abundance values. Such microarrays are disclosed in Wang et al., 2009, "RNA-Seq: a revolutionary tool for transcriptomics," Nat Rev Genet 10, pp. 57-63; Roy et al., 2011, "A comparison of analog and next-generation transcriptomic tools for mammalian studies," Brief Funct Genomic 10:135-150; Shendure, 2008, "The beginning of the end for microarrays?," Nat Methods 5, pp. 585-587; Cloonan et al., 2008, "Stem cell transcriptome profiling via massive-scale mRNA sequencing," Nat. Methods 5, pp. 613-619; Mortazavi et al., 2008, "Mapping and quantifying mammalian transcriptomes by RNA-Seq," Nat Methods 5, pp. 621-628; and Bullard et al., 2010, "Evaluation of statistical methods for normalization and differential expression in mRNA-Seq experiments" BMC Bioinformatics 11, p. 94, each of which is hereby incorporated by reference.

The first computational step of the RNA-seq data analysis pipeline is read mapping: reads are aligned to a reference genome or transcriptome by identifying gene regions that match read sequences. Any of a variety of alignment tools can be used for this task. See, for example, Hatem et al., 2013, "Benchmarking short sequence mapping tools," BMC Bioinformatics 14, p. 184; and Engstrom et al., "Systematic evaluation of spliced alignment programs for RNA-seq data, Nat Methods 10, pp. 1185-1191, each of which is hereby incorporated by reference. In some embodiments, the mapping process starts by building an index of either the reference genome or the reads, which is then used to retrieve the set of positions in the reference sequence where the reads are more likely to align. Once this subset of possible mapping locations has been identified, alignment is performed in these candidate regions with slower and more sensitive algorithms. See, for example, Hatem et al., 2013, "Benchmarking short sequence mapping tools," BMC Bioinformatics 14: p. 184; and Flicek and Bimey, 2009, "Sense from sequence reads: methods for alignment and assembly," Nat Methods 6(Suppl. 11), S6-S12, each of which is hereby incorporated by reference. In some embodiments, the mapping tools is a methodology that makes use of a hash table or makes use of a Burrows-Wheeler transform (BWT). See, for example, Li and Homer, 2010, "A survey of sequence alignment algorithms for next-generation sequencing," Brief Bioinformatics 11, pp. 473-483, which is hereby incorporated by reference.

After mapping, the reads aligned to each coding unit, such as exon, transcript or gene, are used to compute counts, in order to provide an estimate of its abundance (e.g., expression) level. In some embodiments, such counting considers the total number of reads overlapping the exons of a gene. However, because in some instance some of the sequence reads map outside the boundaries of known exons alternative embodiments consider the whole length of a gene, also counting reads from introns. Further still, in some embodiments spliced reads are used to model the abundance of different splicing isoforms of a gene. See, for example, Trapnell et al., 2010, "Transcript assembly and quantification by RNA-Seq reveals unannotated transcripts and isoform switching during cell differentiation," Nat Biotechnol 28, pp. 511-515; and Gatto et al, 2014, "Fine-Splice, enhanced splice junction detection and quantification: a novel pipeline based on the assessment of diverse RNA-Seq alignment solutions," Nucleic Acids Res 42, p. e71, each of which is hereby incorporated by reference.

As explained above, quantification of gene abundance from RNA-seq data is typically implemented in the analysis pipeline through two computational steps: alignment of reads to a reference genome or transcriptome, and subsequent estimation of gene and isoform abundances based on aligned reads. Unfortunately, the reads generated by the most used RNA-Seq technologies are generally much shorter than the transcripts from which they are sampled. As a consequence, in the presence of transcripts with similar sequences, it is not always possible to uniquely assign short sequence reads to a specific gene. Such sequence reads are referred to as "multireads" because they are homologous to more than one region of the reference genome. In some embodiments, such multireads are discarded, that is, they do not contribute to gene abundance counts. In some embodiments, programs such as MMSEQ or RSEM, are used to resolve the ambiguity. See for example, Turro et al., 2011, "Haplotype and isoform specific expression estimation using multi-mapping RNAseq reads," Genome Biol 12, p. R13; and Nicolae et al., "Estimation of alternative splicing isoform frequencies from RNA-Seq data," Algorithms Mol Biol 6, p. 9, each of which is hereby incorporated by reference.

Another aspect of RNA-seq is normalization of sequence read counts. In some embodiments, this includes normalization to take into account different sequencing depths. See, for example, Lin et al., 2011, "Comparative studies of de novo assembly tools for next-generation sequencing technologies," Bioinformatics 27, pp. 2031-2037; Robinson Oshlack, 2010, "A scaling normalization method for differential expression analysis of RNA-seq data," Genome Biol 11, p. R25; and Li et al., 2012, "Normalization, testing, and false discovery rate estimation for RNA-sequencing data, Biostatistics 13, pp. 523-538, each of which is hereby incorporated by reference. In some embodiments, sequence read counts are normalized to account for gene length bias. See, Finotell and Camillo, 2014, "Measuring differential gene expression with RNA-seq: challenges and strategies for data analysis," Briefings in Functional Genomics 14(2), pp. 130-142, which is hereby incorporated by reference.

Block 208.

Referring to block 208 of FIG. 2B, in some embodiments each subject in the plurality of subjects is afflicted with a first type of cancer. In other words, in some embodiments, each subject in database 122 is afflicted with the same type of cancer. In some such embodiments, each subject in the plurality of subjects has breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer.

Block 210.

Referring to block 208 of FIG. 2B, in some embodiments, each subject in the plurality of subjects is afflicted with a first stage of a first type of cancer. In other words, in some embodiments, each subject in database 122 is afflicted with the same type of cancer and this cancer is at the same stage. In some such embodiments, each subject in the plurality of subjects has breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer. Moreover, in such embodiments, the stage of this cancer in each subject in the plurality of subjects is stage I, stage II, stage III, or stage IV cancer.

Blocks 212-214.

Referring to block 212 of FIG. 2B and block 214 of FIG. 2C, the cohort used in the disclosed methods is of sufficient size to develop a classifier that has suitable performance for screening subjects to ascertain whether they have a first or second cancer condition. Thus, in some embodiments, the plurality of subjects comprises one hundred subjects, the first subset of subjects (those that have the first cancer condition) comprises twenty subjects, and the second subset of subjects (those that have the second cancer condition) comprises twenty subjects. This is just an example. In other embodiments, the plurality of subjects comprises one thousand subjects, the first subset of subjects comprises one hundred subjects, and the second subset of subjects comprises one hundred subjects. In still other embodiments, the plurality of subjects comprises one hundred, five hundred, two thousand, four thousand, or ten thousand subjects, the first subset of subjects comprises one hundred subjects, five hundred subjects, or one thousand subjects, and the second subset of subjects comprises one hundred subjects, five hundred subjects, or one thousand subjects. In some embodiments, more of the subjects have the first cancer condition than the second cancer condition. For instance, in some embodiments, more than ten percent, more than twenty percent, more than thirty percent, more than forty percent, more than fifty percent, more than sixty percent, more than seventy percent, more than eighty percent, or more than ninety percent of the subjects in dataset 122 have the first cancer condition while the remainder have the second cancer condition.

Block 216.

Referring to block 216 of FIG. 2C, in some embodiments, the disclosed methods are used with training subjects that are human. Although each training subject in dataset 122 is from the same species, there is no requirement that the species is human. In some embodiments, the species is canine, bovine, porcine, or some other species.

Block 218.

Referring to block 218 of FIG. 2C, once a dataset 122 comprising a corresponding plurality of abundance values for each respective subject in a plurality of subjects of a single species has been obtained, the dataset 122 is used to identify a discriminating gene set using the abundance values and the respective indication of the cancer condition of respective subjects in the plurality of subjects of the dataset 122. The discriminating gene set comprises a subset of the plurality of genes. Specific methods for identifying the discriminating gene set in accordance with some embodiments of the disclosure are detailed below with reference to blocks 226 through 240.

Blocks 220-224.

Referring to block 220 of FIG. 2C, in some embodiments the species under consideration is human, the plurality of genes (for which abundance data is considered) includes ten thousand or more genes, for example, the xGen Exome Research Panel v1.0 (IDT) spans a 39 Mb target region that includes 19,396 genes (see, Nguyen, A., et al., "Multiplexed Hybrid Capture for Whole Exome Sequencing," Technical Note, Integrated DNA Technologies, Inc., (2018), the content of which is hereby incorporated by reference, in its entirety, for all purposes), and the discriminating gene set consists of between five and forty genes. Referring to block 222 of FIG. 2C, in some embodiments the species is human, the plurality of genes includes five thousand genes, and the discriminating gene set consists of between five and twenty-five genes. Other ranges are possible. For instance, in some embodiments, the plurality of genes (for which abundance data is considered) includes at least two hundred, five hundred, one thousand, two thousand, three thousand, four thousand, five thousand, six thousand, seven thousand, eight thousand, nine thousand, ten thousand, fifteen thousand, or twenty thousand genes, and the discriminating gene set consists of between five genes and five hundred genes, between five genes and one hundred genes, between five genes and fifty genes, or between five genes and twenty-five genes. Regardless, of the range, the discriminating gene is smaller than the original plurality of genes. In some embodiments, the discriminating set consists of at least four-fold fewer genes than the plurality of genes in dataset 122 (e.g., a drop from 1000 genes to 250 genes or less). By selecting fewer genes for the discriminating gene set than are available in the dataset 122, algorithms for discriminating between the first and second state can be trained on smaller, more informative data (e.g., abundance data for fewer genes), which leads to more computationally efficient training of classifiers that discriminate between the first and second cancer states. Such improvements in computational efficiency, owing to the reduced size of the discriminating gene set, can advantageously either be used to speed up classifier training or be used to improve the performance of such classifiers (e.g., through more extensive training of the classifier). In some embodiments, the discriminating gene set consists of at least four-fold, five-fold, six-fold, seven-fold, eight-fold, nine-fold, ten-fold, twenty-fold, thirty-fold, forty-fold, or fifty-fold fewer genes than the plurality of genes in dataset 122. Further, reducing the number of genes used for the analysis improves the model, by preventing overfitting of the data.

Block 226.

Referring to block 226 of FIG. 2C, in some embodiments, the identification of the discriminating gene set comprises regressing the dataset 122 based on all or a subset of the plurality of abundance values 126 across the plurality of training subjects 124 against the respective indication of cancer condition 128 across the plurality of training subjects 124 using a regression algorithm to thereby assign a corresponding regression coefficient, in a plurality of regression coefficients, to each respective gene in the plurality of genes. Thus, in such embodiments, the cancer condition is the dependent variable and the abundance values of genes are the independent variables. In such embodiments, genes from the plurality of genes that are selected for the discriminating gene set are those genes that have been assigned a coefficient by the regression algorithm that satisfies a coefficient threshold. In such embodiments, a gene whose coefficient satisfies a coefficient threshold is deemed to be significant enough to have an appreciable effect on the dependent variable, cancer class, and thus is retained for the discriminating gene set. More details on such regression in particular embodiments of the present disclosure is presented below.

Blocks 228 Through 232.

Referring to block 228 of FIG. 2D, in some embodiments, the identification of the discriminating gene set comprises splitting the dataset into a plurality of sets (e.g., between five and fifty sets, exactly 10 sets, etc.). Each set in the plurality of sets includes two or more subjects that are afflicted with the first cancer condition and two or more subjects that are afflicted with the second cancer condition. Then, each respective set in the plurality of sets is independently regressed based on all or a subset of the plurality of abundance values across the subjects of the respective set against the respective indication of cancer condition across the subjects of the respective set using the regression algorithm to thereby assign a corresponding regression coefficient, in the plurality of regression coefficients, to each respective gene in the plurality of genes. Those genes that are assigned a regression coefficient by the regression algorithm that satisfies a coefficient threshold for at least a threshold percentage of the plurality of sets are selected for the discriminating gene set. Referring to block 230, in some embodiments, the coefficient threshold is zero. In some embodiments, the threshold percentage required is at least forty percent of the plurality of sets. Thus, to illustrate, consider the case in which there are 10 sets. In such a case, for gene A to be included in the discriminating gene set, the regression coefficient for gene A, upon regression of each of the 10 sets against cancer condition would need to satisfy a regression threshold in 4 out of the 10 sets. If the regression threshold is zero, meaning that a positive regression coefficient is required to satisfy the regression threshold, the regression coefficient for gene A in at least four of the ten sets would need to be positive. In some embodiments, a threshold is applied to the absolute value of the coefficient. However, in some embodiments as described herein, the threshold is set to 0 because the LASSO regression is designed to return sparse coefficients. In some embodiments, the threshold percentage required is at least fifty percent, at least sixty percent, at least seventy percent, at least eighty percent, at least ninety percent, or all of the plurality of sets. Referring to block 232, in some embodiments the regression coefficient threshold is greater than zero (e.g., 0.1, 0.2, 0.3, or some other positive value). It will be appreciated that requiring larger regression coefficients serves to increase the stringency of what is required for a gene to be included in the discriminating dataset. In vary alternative embodiments, a regression coefficient satisfies a regression coefficient threshold when the absolute value of the regression coefficient upon regression is other than zero, greater than 0.1, or greater than 0.2.

Blocks 234-240.

It will be noted that the dependent variable used in the identification of the discriminating gene set adopts one of two labels, the first cancer condition or the second cancer condition. Accordingly, referring to block 234 of FIG. 2D, in some embodiments, the regression algorithm is logistic regression that assumes:

$$P(Y=1 \mid x_i) = \frac{\exp(\beta_0 + \beta_1 x_{i1} + \ldots + \beta_k x_{ik})}{1 + \exp(\beta_0 + \beta_1 x_{i1} + \ldots + \beta_k x_{ik})},$$

Here, $x_i = (x_{i1}, x_{i2}, \ldots, x_{ik})$ are the corresponding plurality of abundance values for the plurality of genes from the tumor sample of the $i^{th}$ corresponding subject. Further $Y \in \{0, 1\}$ is the class label having the value "1" when the corresponding subject i has the first cancer condition and having the value "0" when the corresponding subject i has the second cancer condition. Thus, $P(Y=1|x_i)$ is the estimated probability that the $i^{th}$ corresponding subject is a member of the first cancer class. The term $\beta_0$ is an intercept and $\beta_j = (j=1, \ldots k)$ is the plurality of regression coefficients. Each respective regression coefficient in the plurality of regression coefficients is for a corresponding gene in the plurality of genes. More specifically, each respective regression coefficient is for the abundance value of a corresponding gene in the plurality of genes across the training subjects 124 in the dataset 122. In the logistic regression in accordance with such embodiments, the $i^{th}$ corresponding subject is assigned to the first cancer class when $P(Y=1|x_i)$ exceeds a predefined threshold value and to the second cancer class otherwise. In some embodiments, this predefined threshold value is 0.5. In some embodiments, this predefined threshold value is a number between 0.25 and 0.75.

Referring to block 238, in some embodiments, the logistic regression is logistic least absolute shrinkage and selection operator (LASSO) regression. In such embodiments, the logistic LASSO estimator $\widehat{\beta_0}, \ldots, \widehat{\beta_k}$ is defined as the minimizer of the negative log likelihood:

$$\min(\Sigma_{i=1}^n [-y_i(\beta_0 + \beta_1 x_i + \ldots + \beta_k x_{ik}) + \log(1 + \exp(\beta_0 + \beta_1 x_i + \ldots + \beta_k x_{ik}))]),$$

subject to the constraint $\Sigma_{j=1}^k |\beta_j| \leq \lambda$. Here, which is $\lambda > 0$, is a tuning parameter that controls the sparsity of the estimator (e.g., the number of regression coefficients with a value of zero) and is selected in practice by using, for example, validation samples or cross-validation. In some embodiments, the glmnet package in R is used to obtain the logistic LASSO estimator. See Friedman et al., 2008, "Regularization Paths for Generalized Linear Models via Coordinate Descent," Journal of Statistical Software 33(1); and Kim, 2018, "Logistic LASSO regression for the diagnosis of breast cancer using clinical demographic data and the BI-RADS lexicon for ultrasonography," Ultrasonography 37, pp. 36-42, each of which is hereby incorporated by reference.

In some embodiments, a regularization method other than LASSO is used to identify the genes in the plurality of genes that discriminate between the first and second cancer state based on gene abundance values across the training subjects 124 of the dataset 122. For instance, in some embodiments, an elastic net is used to identify the genes in the plurality of genes that discriminate between the first and second cancer state based on gene abundance values across the training subjects 124 of the dataset 122. See Zou and Hastie, 2005, "Regularization and variable selection via the elastic net, J R Stat Soc Series B Stat Methodol 67, pp. 301-320, which is hereby incorporated by reference. In some embodiments, a sparse Laplacian penalty is used to identify the genes in the plurality of genes that discriminate between the first and second cancer state based on gene abundance values across the training subjects 124 of the dataset 122. See Huang et al., 2011, "The sparse Laplacian shrinkage estimator for high-dimensional regression, Ann Stat 39, pp. 2021-2046, which is hereby incorporated by reference. In some embodiments, elastic net, group LASSO (Yuan and Lin, 2006, "Model Selection and Estimation in Regression with Grouped Variables," Journal of the Royal Statistical Society. Series B Statistical Methodology 68(1), pp. 49-67), fused LASSO (Tibshirani et al., 2005, "Sparsity and Smoothness via the Fused lasso," Journal of the Royal Statistical Society. Series B Statistical Methodology 67(1), pp. 91-108), quasi-norms and bridge regression (Fu, 1998, "The Bridge versus the Lasso," Journal of Computational and Graphical Statistics 7(3), pp. 397-416), or adaptive LASSO is used to identify the genes in the plurality of genes that discriminate between the first and second cancer state based on gene abundance values across the training subjects 124 of the dataset 122. Referring to block 240 of FIG. 2E, in some embodiments, the regression algorithm includes an L1 (LASSO) or L2 (Ridge) regularization term.

Block 242-244.

The above disclosure details how the gene abundance values 126 of subjects 124 in a training set 122 are used to identify a discriminating gene set whose abundance values collectively discriminate between a first and second cancer state. Once this discriminating gene set is identified, the training set 122 is then used to formally train a classifier that can discriminate between the first and second cancer states for a test subject using the abundance values of the discriminating genes that are measured from a biological sample taken from a test subject. In typical embodiments, the cancer state of this test subject is not known. That is, while it may be known that the test subject has a particular cancer, it is not known whether the subject has been afflicted with a pathogen that has an adverse effect on the prognosis of the subject's cancer. In typical embodiments the biological sample used to measure the gene abundance values of the test subject is a solid tumor within the test subject. Referring to block 242, in some embodiments, the respective abundance values for the discriminating gene set and the respective indication of cancer condition across the plurality of subjects are used to train a classifier to discriminate between the first cancer condition and the second cancer condition as a function of respective abundance values for the discriminating gene set. In some embodiments, as disclosed in the Examples below, make use of additional features in addition to abundance values of the discriminating gene set to train the classifier. For instance, in some embodiments absence of presence of specific mutations in select genes is also used to train the classifier in conjunction with the abundance values for the discriminating gene set.

Referring to block 244 of FIG. 2E, in some embodiments, by way of non-limiting example, the classifier used in block 242 is a logistic regression algorithm, a neural network algorithm, a convolutional neural network algorithm, a support vector machine (SVM) algorithm, a Naive Bayes algorithm, a nearest neighbor algorithm, a boosted trees algorithm, a random forest algorithm, a decision tree algorithm, a clustering algorithm, or combinations thereof.

Logistic regression algorithms suitable for use as the classifier of block 242 are disclosed, for example, in Agresti, *An Introduction to Categorical Data Analysis,* 1996, Chapter 5, pp. 103-144, John Wiley & Son, New York, which is hereby incorporated by reference.

Neural network algorithms, including convolutional neural network algorithms, suitable for use as the classifier of block 242 are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. In multilayer neural networks, there are input units (input layer), hidden units (hidden layer), and output units (output layer). There is, furthermore, a single bias unit that is con-nected to each unit other than the input units. Additional example neural networks suitable for use as the classifier of block 242 are disclosed in Duda et al., 2001, *Pattern Classification,* Second Edition, John Wiley & Sons, Inc., New York; and Hastie et al., 2001, *The Elements of Statistical Learning,* Springer-Verlag, New York, each of which is hereby incorporated by reference in its entirety. Additional example neural networks suitable for use as the classifier of block 242 are also described in Draghici, 2003, *Data Analysis Tools for DNA Microarrays,* Chapman & Hall/CRC; and Mount, 2001, *Bioinformatics: sequence and genome analysis,* Cold Spring Harbor Laboratory Press, Cold Spring Harbor, N.Y., each of which is hereby incorporated by reference in its entirety.

SVM algorithms suitable for use as the classifier of block 242 are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5$^{th}$ Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data training set (here, the first and second cancer condition of each subject in dataset 122) with a hyperplane that is maximally distant from the labeled data. For cases in which no linear separation is possible, SVMs can work in combination with the technique of kernels, which automatically realize a non-linear mapping to a feature space. The hyperplane found by the SVM in feature space corresponds to a non-linear decision boundary in the input space.

Naïve Bayes classifiers suitable for use as the classifier of block 242 are disclosed, for example, in Ng et al., 2002, "On discriminative vs. generative classifiers: A comparison of logistic regression and naive Bayes," Advances in Neural Information Processing Systems, 14, which is hereby incorporated by reference.

Decision trees algorithms suitable for use as the classifier of block 242 are described in, for example, Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used as the classifier of block 244 is a classification and regression tree (CART). Other examples of specific decision tree algorithms that can be used as the classifier of block 244 include, but are not limited to, ID3, C4.5, MART, and Random Forests. CART, ID3, and C4.5 are described in Duda, 2001, *Pattern Classification,* John Wiley & Sons, Inc., New York. pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U. C. Berkeley, September 1999, which is hereby incorporated by reference in its entirety.

Clustering algorithms suitable for use as the classifier of block 242 are described, for example, at pages 211-256 of Duda and Hart, *Pattern Classification and Scene Analysis,* 1973, John Wiley & Sons, Inc., New York, (hereinafter "Duda 1973") which is hereby incorporated by reference in its entirety. As set forth in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Here, the similarity measure is on the abundance levels of the discriminating gene set across the training dataset 122. Second, a mechanism for partitioning the data into clusters using the similarity measure is determined. Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 216 of Duda 1973.

Once a method for measuring "similarity" or "dissimilarity" between points in a dataset has been selected, clustering makes use of a criterion function that measures the clustering quality of any partition of the data. Partitions of the dataset that extremize the criterion function are used to cluster the data. See page 217 of Duda 1973. Criterion functions are discussed in Section 6.8 of Duda 1973. More recently, Duda et al., Pattern Classification, $2^{nd}$ edition, John Wiley & Sons, Inc. New York, has been published. Pages 537-563 describe clustering in detail. More information on clustering techniques suitable for use as the classifier in block 242 are disclosed in Kaufman and Rousseeuw, 1990, *Finding Groups in Data: An Introduction to Cluster Analysis*, Wiley, New York, N.Y.; Everitt, 1993, Cluster analysis (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used as the classifier of block 242 include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

In some embodiments, the classifier used for block 242 is a nearest neighbor algorithm. For nearest neighbors, given a query point $x_0$ (a test subject), the k training points $x_{(r)}$, r, . . . , k (here the training subjects) closest in distance to $x_0$ are identified and then the point $x_0$ is classified using the k nearest neighbors. Here, the distance to these neighbors is a function of the abundance values of the discriminating gene set. In some embodiments, Euclidean distance in feature space is used to determine distance as $d_{(i)}=\|x_{(i)}-x_{(o)}\|$. Typically, when the nearest neighbor algorithm is used, the abundance data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference.

Blocks 246-248.

The above disclosure describes the training of a classifier using the abundance values of a discriminating gene set.

Referring to block 246, in some embodiments, the trained classifier is then used to classify a test subject to determine whether the test subject has the first cancer condition or the second cancer condition by inputting a test plurality of abundance values into the classifier. In such embodiments, each respective abundance value in the test plurality of abundance values quantifies a level of expression of a corresponding gene, in the plurality of genes, and more specifically in the discriminating gene set, in a biological sample (e.g., tumor sample) of the test subject. Responsive to this input, the classifier specifies whether the test subject has the first cancer condition or the second cancer condition.

Referring to block 246, in some alternative embodiments, the trained classifier is used to determine the likelihood or probability that a test subject has the first cancer condition or the second condition. This is done in such embodiments by inputting a test plurality of abundance values into the classifier. In such embodiments, each respective abundance value in the test plurality of abundance values quantifies a level of expression of a corresponding gene, in the plurality of genes (more specifically in the discriminating gene set) in a biological sample (e.g., tumor sample) of the test subject. Responsive to this input, the classifier specifies a likelihood or probability that the test subject has the first cancer condition or, alternatively, a likelihood or probability that the test subject has the second cancer condition.

Referring to block 248, in some embodiments, a therapeutic intervention or imaging of the test subject is provided based on a determination that the test subject has the first cancer condition or the second cancer condition (or likelihood that the test subject has the first or second cancer condition). Examples of such conditional therapies are provided below in conjunction with FIG. 3. For example, non-limited examples of ongoing clinical trials of therapies for particular cancer types that are associated with oncogenic pathogen infections are provided in Table 2, below.

RNA Analysis Pipeline

In some embodiments, the methods and systems described herein are performed in conjunction with sequencing of RNA molecules isolated from a biological sample of a patient. In some embodiments, a FASTQ file, or equivalent file format, of the sequencing data is the output of such a sequencing reaction.

In some embodiments, each FASTQ file contains reads that may be paired-end or single reads, and may be short-reads or long-reads, where each read shows one detected sequence of nucleotides in an mRNA molecule that was isolated from the patient sample, inferred by using the sequencer to detect the sequence of nucleotides contained in a cDNA molecule generated from the isolated mRNA molecules during library preparation. Each read in the FASTQ file is also associated with a quality rating. The quality rating may reflect the likelihood that an error occurred during the sequencing procedure that affected the associated read.

Each FASTQ file may be processed by a bioinformatics pipeline. In various embodiments, the bioinformatics pipeline may filter FASTQ data. Filtering FASTQ data may include correcting sequencer errors and removing (trimming) low quality sequences or bases, adapter sequences, contaminations, chimeric reads, overrepresented sequences, biases caused by library preparation, amplification, or capture, and other errors. Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools. FASTQ files may be analyzed for rapid assessment of quality control and reads, for example, by a sequencing data QC software such as AfterQC, Kraken, RNA-SeQC, FastQC, (see Illumina, BaseSpace Labs or https://www.illumina.com/products/by-type/informatics-products/basespace-sequence-hub/apps/fastqc.html), or another similar software program. For paired-end reads, reads may be merged.

For each FASTQ file, each read in the file may be aligned to the location in the reference genome having a sequence that best matches the sequence of nucleotides in the read. There are many software programs designed to align reads, for example, Bowtie, Burrows Wheeler Aligner (BWA), programs that use a Smith-Waterman algorithm, etc. Alignment may be directed using a reference genome (for example, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may take RNA splice sites into account. The alignment may generate a SAM file, which stores the locations of the start and end of each read in the reference genome and the coverage (number of reads) for each nucleotide in the reference genome. The SAM files may be converted to BAM files, BAM files may be sorted, and duplicate reads may be marked for deletion.

In one example, kallisto software may be used for alignment and RNA read quantification (see Nicolas L Bray, Harold Pimentel, Pill Melsted and Lior Pachter, Near-optimal probabilistic RNA-seq quantification, Nature Biotechnology 34, 525-527 (2016), doi:10.1038/nbt.3519). In an alternative embodiment, RNA read quantification may be conducted using another software, for example, Sailfish or Salmon (see Rob Patro, Stephen M. Mount, and Carl Kingsford (2014) Sailfish enables alignment-free isoform quantification from RNA-seq reads using lightweight algorithms. Nature Biotechnology (doi:10.1038/nbt.2862) or Patro, R., Duggal, G., Love, M. I., Irizarry, R. A., & Kingsford, C. (2017). Salmon provides fast and bias-aware quantification of transcript expression. Nature Methods.). These RNA-seq quantification methods may not require alignment. There are many software packages that may be used for normalization, quantitative analysis, and differential expression analysis of RNA-seq data.

For each gene, the raw RNA read count for a given gene may be calculated. The raw read counts may be saved in a tabular file for each sample, where columns represent genes and each entry represents the raw RNA read count for that gene. In one example, kallisto alignment software calculates raw RNA read counts as a sum of the probability, for each read, that the read aligns to the gene. Raw counts are therefore not integers in this example.

Raw RNA read counts may then be normalized to correct for GC content and gene length, for example, using full quantile normalization and adjusted for sequencing depth, for example, using the size factor method. In one example, RNA read count normalization is conducted according to the methods disclosed in U.S. patent application Ser. No. 16/581,706 or PCT19/52801, titled Methods of Normalizing and Correcting RNA Expression Data and filed Sep. 24, 2019, which are incorporated by reference herein in their entirety. The rationale for normalization is the number of copies of each cDNA molecule in the sequencer may not reflect the distribution of mRNA molecules in the patient sample. For example, during library preparation, amplification, and capture steps, certain portions of mRNA molecules may be over or under-represented due to artifacts that arise during various aspects of priming of reverse transcription caused by random hexamers, amplification (PCR enrichment), rRNA depletion, and probe binding and errors produced during sequencing that may be due to the GC content, read length, gene length, and other characteristics of sequences in each nucleic acid molecule. Each raw RNA read count for each gene may be adjusted to eliminate or reduce over- or under-representation caused by any biases or artifacts of NGS sequencing protocols. Normalized RNA read counts may be saved in a tabular file for each sample, where columns represent genes and each entry represents the normalized RNA read count for that gene.

A transcriptome value set may refer to either normalized RNA read counts or raw RNA read counts, as described above.

HPV Classifier Training

In one aspect, the disclosure provides a method for training a classifier to detect human papillomavirus (HPV) infection in a cancer. The method includes obtaining abundance values 126, e.g., mRNA expression levels, for genes that are informative for evaluating the HPV status of HPV-associated cancers, from a training set of subjects 124 with an HPV-associated cancer and known HPV status. The method then includes training a classifier, e.g., using classifier training module 120, against, for each respective training subject, at least (i) the abundance values 126, and (ii) the HPV status of the patient's cancer. In some embodiments, the classifier is also trained against the status of one or more variant alleles 127 in the cancer of each training subject.

In some embodiments, each training subject has an HPV-associated cancer selected from cervical cancer, head and neck squamous cell carcinoma, ovarian cancer, penile cancer, pharyngeal cancer, anal cancer, vaginal cancer, and vulvar cancer. In some embodiments, a classifier is trained against data from patients that all have the same type of cancer, e.g., cervical cancer, head and neck squamous cell carcinoma, ovarian cancer, penile cancer, pharyngeal cancer, anal cancer, vaginal cancer, or vulvar cancer. However, as classifier training is generally improved by increasing the size of the training dataset, in some embodiments, the classifier is trained against data from patients that have two or more type of HPV-associated cancers, e.g., two, three, four, five, six, seven, or all eight of cervical cancer, head and neck squamous cell carcinoma, ovarian cancer, penile cancer, pharyngeal cancer, anal cancer, vaginal cancer, and vulvar cancer. In a particular embodiment, exemplified by Example 3 each training subject has either head and neck squamous cell carcinoma or cervical cancer.

In some embodiments, the classifier is trained against abundance values for a plurality of genes selected from those listed in Table 3, e.g., KRT86, CRISPLD1, DSG1, SESN3, DAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1. As reported below, e.g., in reference to Example 3, these twenty-four genes were found to be differentially expressed, dependent upon the HPV status of the subject, in at least eight of the ten training sets formed from expression data of cervical or head and neck cancers with known HPV statuses in The Cancer Genome Atlas (TCGA). However, the skilled artisan will appreciate that, is some instances, the use of different training data sets may yield different results, e.g., one or more of these genes may not be informative in at least 80% of training folds and/or one or more genes found not to be informative in at least 80% of training folds in the study reported in Example 3 may be informative. These differences may arise, for example, when different criteria are used to select the training population, e.g., different inclusion and/or exclusion criteria such as cancer type, personal characteristics (e.g., age, gender, ethnicity, family history, smoking status, etc.), or simply by using a smaller or larger data set.

Accordingly, in some embodiments, the classifier is trained against at least five of the genes listed in Table 3. In some embodiments, the classifier is trained against at least ten of the genes listed in Table 3. In some embodiments, the classifier is trained against at least fifteen of the genes listed in Table 3. In some embodiments, the classifier is trained against at least twenty of the genes listed in Table 3. In some embodiments, the classifier is trained against all twenty-four of the genes listed in Table 3. In some embodiments, the classifier is trained against 5, 6, 7, 8, 9, 10, 11, 12, 13, 14, 15, 16, 17, 18, 19, 20, 21, 22, 23, or all 24 of the genes listed in Table 3. Further, in some embodiments, the classifier is also trained against the abundance values for one or more genes not listed in Table 3. In some embodiments, the classifier is also trained against the abundance value for 1, 2, 3, 4, 5, 6, 7, 8, 9, 10 or more genes not listed in Table 3. In some embodiments, the classifier is also trained against the abundance values for 1-10 genes not listed in Table 3. In some embodiments, the classifier is also trained against 1-5 genes not listed in Table 3. In other embodiments, the classifier is not trained against the abundance values for any genes not listed in Table 3.

Further, the skilled artisan will also appreciate that some features, e.g., abundance values for a particular gene, will be more informative than other features in a particular classifier. One measure of the predictive power of respective features in a classifier based on multiple features is the regression coefficient calculated for the features during training of the model. Regression coefficients describe the relationship between each feature and the response of the model. The coefficient value represents the mean change in the response given a one-unit increase in the feature value. As such, at least for variables of the same type, the magnitude, e.g., absolute value, of a regression coefficient is correlated with the importance of the feature in the model. That is, the higher the magnitude of the regression coefficient, the more important the variable is to the model. For instance, as reported in Example 3, in a particular support vector machine (SVM) classifier trained against the abundance values of all twenty-four of the genes listed in Table 3, as well as a variant allele status for the TP53 and CDKN2A genes, only six of the 24 genes had regression coefficients with magnitudes of at least 0.5-CDKN2A (1.13), SMC1B (1.02), EFNB3 (−0.97), KCNS1 (0.74), CCND1 (−0.65), and RNF212 (0.517).

As such, the skilled artisan may select a feature set that includes less than all of the genes listed in Table 3 based, at least in part, upon the importance of the respective features in one or more classification models. For instance, in some embodiments, one or more genes with lower predictive power in a classification model may be left out during classifier training. For example, in some embodiments, the features used for training include at least the gene expression features listed in Table 5 with a regression coefficient of at least 0.5, e.g., CDKN2A, SMC1B, EFNB3, KCNS1, CCND1, and RNF212. In some embodiments, the features used for training include at least the gene expression features listed in Table 5 with a regression coefficient of at least 0.4. In some embodiments, the features used for training include at least the gene expression features listed in Table 5 with a regression coefficient of at least 0.3. In some embodiments, the features used for training include at least the gene expression features listed in Table 5 with a regression coefficient of at least 0.2. In some embodiments, the features used for training include at least the gene expression features listed in Table 5 with a regression coefficient of at least 0.1.

Similarly, the size of the feature set may be affected by which features are included and/or excluded. For instance, in some embodiments, if particular features having high predictive power are included in a classification model, fewer total features may be included in the model. For instance, in some embodiments, if the abundance values for SMC1B, CDKN2A, and EFNB3 are included in the model, the abundance values for no more than two of the other genes whose abundance values are used as features in Table 5 need to be included in the model. Accordingly, in some embodiments, the features used to train the model include abundance values for SMC1B, CDKN2A, and EFNB3, and at least two other genes whose abundance values are used as features in Table 5. In some embodiments, the features used to train the model include abundance values for SMC1B, CDKN2A, and EFNB3, and at least five other genes whose abundance values are used as features in Table 5. In some embodiments, the features used to train the model include abundance values for SMC1B, CDKN2A, and EFNB3, and at least ten other genes whose abundance values are used as features in Table 5. In some embodiments, the features used to train the model include abundance values for SMC1B, CDKN2A, and EFNB3, and at least fifteen other genes whose abundance values are used as features in Table 5.

Similarly, in some embodiments, if features having high predictive power are excluded from the classification model, more of the other features may be included in the model. For instance, in some embodiments, if the abundance values for one or more of SMC1B, CDKN2A, and EFNB3 are not included in the model, the abundance values for at least fifteen of the other whose abundance values are used as features in Table 5 are included in the model. In some embodiments, if the abundance values for one or more of SMC1B, CDKN2A, and EFNB3 are not included in the model, the abundance values for at least twenty of the other genes whose abundance values are used as features in Table 5 are included in the model. In some embodiments, if the abundance values for one or more of SMC1B, CDKN2A, and EFNB3 are not included in the model, the abundance values for at least 15, 16, 17, 18, 19, 20, or all 21 of the other genes whose abundance values are used as features in Table 5 are included in the model.

Of course, other metrics are also available for evaluating the importance of a feature in a model, such as standardized regression coefficients and change in R-squared when the feature is added to the model last.

When selecting a feature set, the skilled artisan will also consider the degree to which features are correlated to each other. Correlation is a statistical measure of how linearly dependent two variables are upon each other. As such, two correlated features provide duplicative information to a predictive model, which can be detrimental to a classifier. As such, there are several reasons why a correlated feature may be excluded from a model. For instance, removing a correlated feature will make the algorithm faster, as the larger the number of features in a classifier the more computations that need to be made. Removing a correlated feature may also remove harmful bias, arising from the correlation, from a model. Finally, removing a correlated feature may make the model more interpretable.

As such, the skilled artisan may select a feature set that includes less than all of the genes listed in Table 3 based, at least in part, upon the correlation between respective features in one or more classification models. In some embodiments, the selection to remove one or the other feature of a correlated feature set is informed by predictive powers of the two features, e.g., their respective regression coefficients. For example, the gene expression values for ENSG00000105278 (CXCL14) and ENSG00000077935 (SMC1B) are highly correlated in the feature set listed in Table 3 (correlation=0.718983175). Accordingly, in some embodiments, the feature set does not include either CXCL14 or SMC1B. In some embodiments, CXCL14, rather than SMC1B is excluded from the feature set because, as reported in Table 5, SMC1B has a higher regression coefficient (1.02) than CXCL14 (−0.29) in the SVM model described in Example 3.

As reported in Table 6, ten pairs of gene expression features have a correlation of at least 0.6. Accordingly, in some embodiments, a feature in at least one pair of features having a correlation of at least 0.6 is excluded from the model. In some embodiments, a feature in at least two pairs of features having a correlation of at least 0.6 is excluded from the model. In other embodiments, a feature in at least 3, 4, 5, 6, 7, 8, 9, or all 10 pairs of features having a correlation of at least 0.6 is excluded from the model. In some embodiments, an excluded feature is the feature in a pair of highly correlated features having the lower regression coefficient reported in Table 5. For instance, with reference to Table 6, the feature having the lower regression coefficient in each highly correlated pair (e.g., corresponding to a correlation of at least 0.6) are:

Pair 1=DSG1
Pair 2=ZFR2
Pair 3=RNF212
Pair 4=SYCP2
Pair 5=ZFR2
Pair 6=MYO3A
Pair 7=SYCP2
Pair 8=DSG1
Pair 9=KCNS1
Pair 10=ZFR2

Accordingly, in some embodiments, one or more of DSG1, ZFR2, RNF212, SYCP2, MYO3A, and KCNS1 are excluded from the features set on the basis that they are the least informative feature in a pair of highly correlated features.

However, in some embodiments, this selection process does not allow both features of a highly correlated pair of features to be excluded from the feature set, e.g., on the basis that both genes are the least informative feature in at least one of the highly correlated pairs of features. Thus, in some embodiments, one or more of SYCP2, MYO3A, and KCNS1 are not excluded from the feature set. Similarly, in some embodiments, this selection process does not allow highly informative features, e.g., features with regression coefficients of at least 0.5, to be excluded from the feature set. Thus, in some embodiments, one or both of RNF212 and KCNS1 are not excluded from the feature set.

Accordingly, in one embodiment, the feature set includes abundance values for at least KRT86, CRISPLD1, SESN3, DAMTS20, IRX1, SMC1B, CDKN2A, EFNB3, CXCL14, MKRN3, SYCP2, MYL1, MYO3A, RNASE10, GALNT13, C19orf26, MUC4, PCDHGB1, CCND1, LCE1F, and KCNS1.

Similarly, in one embodiment, the feature set includes abundance values for at least KRT86, CRISPLD1, SESN3, DAMTS20, IRX1, SMC1B, CDKN2A, EFNB3, CXCL14, RNF212, MKRN3, MYL1, RNASE10, GALNT13, C19orf26, MUC4, PCDHGB1, CCND1, LCE1F, and KCNS1.

Similarly, in one embodiment, the feature set includes abundance values for at least KRT86, CRISPLD1, SESN3, DAMTS20, IRX1, SMC1B, CDKN2A, EFNB3, CXCL14, RNF212, MKRN3, SYCP2, MYL1, MYO3A, RNASE10, GALNT13, C19orf26, MUC4, PCDHGB1, CCND1, LCE1F, and KCNS1.

In some embodiments, the classifier has a specificity of at least 70% and a sensitivity of at least 70% for a validation data set of at least 50 data constructs, e.g., where none of the data constructs in the validation data set were used in the training of the classifier. In some embodiments, the classifier has a specificity of at least 75% and a sensitivity of at least 75% for a validation data set of at least 50 data constructs, e.g., where none of the data constructs in the validation data set were used in the training of the classifier. In some embodiments, the classifier has a specificity of at least 80% and a sensitivity of at least 80% for a validation data set of at least 50 data constructs, e.g., where none of the data constructs in the validation data set were used in the training of the classifier. In some embodiments, the classifier has a specificity of at least 85% and a sensitivity of at least 85% for a validation data set of at least 50 data constructs, e.g., where none of the data constructs in the validation data set were used in the training of the classifier. In some embodiments, the classifier has a specificity of at least 90% and a sensitivity of at least 90% for a validation data set of at least 50 data constructs, e.g., where none of the data constructs in the validation data set were used in the training of the classifier. In some embodiments, the classifier has a specificity of at least 95% and a sensitivity of at least 95% for a validation data set of at least 50 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 50 data constructs. In some embodiments, the classifier has a sensitivity of at least 70%, 75%, 80%, 85%, 90%, 95%, 96%, 97%, 98%, 99%, or higher for a validation data set of at least 50 data constructs.

In some embodiments, the classifier has a specificity of at least 70% and a sensitivity of at least 70% for a validation data set of at least 100 data constructs, e.g., where none of the data constructs in the validation data set were used in the training of the classifier. In some embodiments, the classifier has a specificity of at least 75% and a sensitivity of at least 75% for a validation data set of at least 100 data constructs, e.g., where none of the data constructs in the validation data set were used in the training of the classifier. In some embodiments, the classifier has a specificity of at least 80% and a sensitivity of at least 80% for a validation data set of at least 100 data constructs, e.g., where none of the data constructs in the validation data set were used in the training of the classifier. In some embodiments, the classifier has a specificity of at least 85% and a sensitivity of at least 85% for a validation data set of at least 100 data constructs, e.g., where none of the data constructs in the validation data set were used in the training of the classifier. In some embodiments, the classifier has a specificity of at least 90% and a sensitivity of at least 90% for a validation data set of at least 100 data constructs, e.g., where none of the data constructs in the validation data set were used in the training of the classifier. In some embodiments, the classifier has a specificity of at least 95% and a sensitivity of at least 95% for a validation data set of at least 100 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 100 data constructs. In some embodiments, the classifier has a sensitivity of at least 70%, 75%, 80%, 85%, 90%, 95%, 96%, 97%, 98%, 99%, or higher for a validation data set of at least 100 data constructs.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

EBV Classifier Training

In one aspect, the disclosure provides a method for training a classifier to detect Epstein-Barr virus (EBV) infection in a cancer. The method includes obtaining abundance values 126, e.g., mRNA expression levels, for genes that are informative for evaluating the EBV status of EBV-associated cancers, from a training set of subjects 124 with an EBV-associated cancer and known EBV status. The method then includes training a classifier, e.g., using classifier training module 120, against, for each respective training subject, at least (i) the abundance values 126, and (ii) the EBV status of the patient's cancer. In some embodiments, the classifier is also trained against the status of one or more variant alleles 127 in the cancer of each training subject.

In some embodiments, each training subject has an EBV-associated cancer selected from Burkitt's lymphoma, sinonasal angiocentric T-cell lymphoma, non-Hodgkin's lymphoma, Hodgkin's lymphoma, nasopharyngeal carcinoma, and gastric cancer. In some embodiments, a classifier is trained against data from patients that all have the same type of cancer, e.g., Burkitt's lymphoma, sinonasal angiocentric T-cell lymphoma, non-Hodgkin's lymphoma, Hodgkin's lymphoma, nasopharyngeal carcinoma, or gastric cancer. However, as classifier training is generally improved by increasing the size of the training dataset, in some embodiments, the classifier is trained against data from patients that have two or more type of EBV-associated cancers, e.g., two, three, four, five, or all six of Burkitt's lymphoma, sinonasal angiocentric T-cell lymphoma, non-Hodgkin's lymphoma, Hodgkin's lymphoma, nasopharyngeal carcinoma, and gastric cancer. In a particular embodiment, exemplified by Example 4 each training subject has gastric cancer.

In some embodiments, the classifier is trained against abundance values for a plurality of genes selected from those listed in Table 4, e.g., SCNN1A, CDX1, KCNK15, PRKCG, KRT7, NKD2, GPR158, CLDN3, and ZNF683. As reported below, e.g., in reference to Example 4, these nine genes were found to be differentially expressed, dependent upon the EBV status of the subject, in at least 80% of the gastric cancer training sets in The Cancer Genome Atlas (TCGA). However, the skilled artisan will appreciate that, is some instances, the use of different training data sets may yield different results, e.g., one or more of these genes may not be informative in at least 80% of training folds and/or one or more genes found not to be informative in at least 80% of training folds in the study reported in Example 4 may be informative. These differences may arise, for example, when different criteria are used to select the training population, e.g., different inclusion and/or exclusion criteria such as cancer type, personal characteristics (e.g., age, gender, ethnicity, family history, smoking status, etc.), or simply by using a smaller or larger data set.

Accordingly, in some embodiments, the classifier is trained against at least five of the genes listed in Table 4. In some embodiments, the classifier is trained against at least six of the genes listed in Table 4. In some embodiments, the classifier is trained against at least seven of the genes listed in Table 4. In some embodiments, the classifier is trained against at least eight of the genes listed in Table 4. In some embodiments, the classifier is trained against all nine of the genes listed in Table 4. Further, in some embodiments, the classifier is also trained against the abundance values for one or more genes not listed in Table 4. In some embodiments, the classifier is also trained against the abundance value for 1, 2, 3, 4, 5, 6, 7, 8, 9, 10 or more genes not listed in Table 4. In some embodiments, the classifier is also trained against the abundance values for 1-10 genes not listed in Table 4. In some embodiments, the classifier is also trained against 1-5 genes not listed in Table 4. In other embodiments, the classifier is not trained against the abundance values for any genes not listed in Table 4.

Further, the skilled artisan will also appreciate that some features, e.g., abundance values for a particular gene, will be more informative than other features in a particular classifier. One measure of the predictive power of respective features in a classifier based on multiple features is the regression coefficient calculated for the features during training of the model. Regression coefficients describe the relationship between each feature and the response of the model. The coefficient value represents the mean change in the response given a one-unit increase in the feature value. As such, at least for variables of the same type, the magnitude, e.g., absolute value, of a regression coefficient is correlated with the importance of the feature in the model. That is, the higher the magnitude of the regression coefficient, the more important the variable is to the model. For instance, as reported in Example 4, in a particular support vector machine (SVM) classifier trained against the abundance values of all nine of the genes listed in Table 4, as well as a variant allele status for the TP53 and PIK3CA genes, only four of the nine genes had regression coefficients with magnitudes of at least 0.75-SCNN1A (−1.26), KCNK15 (−1.04), KRT7 (−0.94), and CLDN3 (−1.68).

As such, the skilled artisan may select a feature set that includes less than all of the genes listed in Table 4 based, at least in part, upon the importance of the respective features in one or more classification models. For instance, in some embodiments, one or more genes with lower predictive power in a classification model may be left out during classifier training. For example, in some embodiments, the features used for training include at least the gene expression features listed in Table 5 with a regression coefficient of at least 0.75, e.g., SCNN1A (−1.26), KCNK15 (−1.04), KRT7 (−0.94), and CLDN3 (−1.68). In some embodiments, the features used for training include at least the gene expression features listed in Table 5 with a regression coefficient of at least 0.6.

Similarly, the size of the feature set may be affected by which features are included and/or excluded. For instance, in some embodiments, if particular features having high predictive power are included in a classification model, fewer total features may be included in the model. For instance, in some embodiments, if the abundance values for SCNN1A, KCNK15, KRT7, and CLDN3 are included in the model, the abundance values for no more than one of the other genes listed in Table 4 need to be included in the model. Accordingly, in some embodiments, the features used to train the model include abundance values for SCNN1A, KCNK15, KRT7, and CLDN3, and at least one other genes listed in Table 4. In some embodiments, the features used to train the model include abundance values for SCNN1A, KCNK15, KRT7, and CLDN3, and at least two other genes listed in Table 4. SCNN1A, KCNK15, KRT7, and CLDN3, and at least three other genes listed in Table 4. SCNN1A, KCNK15, KRT7, and CLDN3, and at least four other genes listed in Table 4.

Similarly, in some embodiments, if features having high predictive power are excluded from the classification model, more of the other features may be included in the model. For instance, in some embodiments, if the abundance values for one or more of SCNN1A, KCNK15, KRT7, and CLDN3 are not included in the model, the abundance values for at least four of the other genes listed in Table 4 are included in the model. In some embodiments, if the abundance values for one or more of SCNN1A, KCNK15, KRT7, and CLDN3 are not included in the model, the abundance values for all five of the other genes listed in Table 4 are included in the model.

Of course, other metrics are also available for evaluating the importance of a feature in a model, such as standardized regression coefficients and change in R-squared when the feature is added to the model last.

When selecting a feature set, the skilled artisan will also consider the degree to which features are correlated to each other. Correlation is a statistical measure of how linearly dependent two variables are upon each other. As such, two correlated features provide duplicative information to a predictive model, which can be detrimental to a classifier. As such, there are several reasons why a correlated feature may be excluded from a model. For instance, removing a correlated feature will make the algorithm faster, as the larger the number of features in a classifier the more computations that need to be made. Removing a correlated feature may also remove harmful bias, arising from the correlation, from a model. Finally, removing a correlated feature may make the model more interpretable. As such, the skilled artisan may select a feature set that includes less than all of the genes listed in Table 3 based, at least in part, upon the correlation between respective features in one or more classification models. For example, statistical analysis of the SVM model trained in Example 4 revealed that the gene expression values for ENSG00000135480 (KRT7) and ENSG00000124249 (KCNK15) were highly correlated (0.650). Accordingly, in some embodiments, the abundance value for one of KRT7 and KCNK15 are excluded from the feature set.

For example, in one embodiment, the feature set includes abundance values for at least SCNN1A, CDX1, KCNK15, PRKCG, NKD2, GPR158, CLDN3, and ZNF683. In another embodiment, the feature set includes abundance values for at least SCNN1A, CDX1, PRKCG, KRT7, NKD2, GPR158, CLDN3, and ZNF683.

In some embodiments, the classifier has a specificity of at least 70% and a sensitivity of at least 70% for a validation data set of at least 50 data constructs, e.g., where none of the data constructs in the validation data set were used in the training of the classifier. In some embodiments, the classifier has a specificity of at least 75% and a sensitivity of at least 75% for a validation data set of at least 50 data constructs, e.g., where none of the data constructs in the validation data set were used in the training of the classifier. In some embodiments, the classifier has a specificity of at least 80% and a sensitivity of at least 80% for a validation data set of at least 50 data constructs, e.g., where none of the data constructs in the validation data set were used in the training of the classifier. In some embodiments, the classifier has a specificity of at least 85% and a sensitivity of at least 85% for a validation data set of at least 50 data constructs, e.g., where none of the data constructs in the validation data set were used in the training of the classifier. In some embodiments, the classifier has a specificity of at least 90% and a sensitivity of at least 90% for a validation data set of at least 50 data constructs, e.g., where none of the data constructs in the validation data set were used in the training of the classifier. In some embodiments, the classifier has a specificity of at least 95% and a sensitivity of at least 95% for a validation data set of at least 50 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 50 data constructs. In some embodiments, the classifier has a sensitivity of at least 70%, 75%, 80%, 85%, 90%, 95%, 96%, 97%, 98%, 99%, or higher for a validation data set of at least 50 data constructs.

In some embodiments, the classifier has a specificity of at least 70% and a sensitivity of at least 70% for a validation data set of at least 100 data constructs, e.g., where none of the data constructs in the validation data set were used in the training of the classifier. In some embodiments, the classifier has a specificity of at least 75% and a sensitivity of at least 75% for a validation data set of at least 100 data constructs, e.g., where none of the data constructs in the validation data set were used in the training of the classifier. In some embodiments, the classifier has a specificity of at least 80% and a sensitivity of at least 80% for a validation data set of at least 100 data constructs, e.g., where none of the data constructs in the validation data set were used in the training of the classifier. In some embodiments, the classifier has a specificity of at least 85% and a sensitivity of at least 85% for a validation data set of at least 100 data constructs, e.g., where none of the data constructs in the validation data set were used in the training of the classifier. In some embodiments, the classifier has a specificity of at least 90% and a sensitivity of at least 90% for a validation data set of at least 100 data constructs, e.g., where none of the data constructs in the validation data set were used in the training of the classifier. In some embodiments, the classifier has a specificity of at least 95% and a sensitivity of at least 95% for a validation data set of at least 100 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 100 data constructs. In some embodiments, the classifier has a sensitivity of at least 70%, 75%, 80%, 85%, 90%, 95%, 96%, 97%, 98%, 99%, or higher for a validation data set of at least 100 data constructs.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

Classification Methods.

In some embodiments, the disclosure provides methods for discriminating between a first cancer condition and a second cancer condition in a human subject, where the first cancer condition is associated with infection by an oncogenic pathogen and the second cancer condition is associated with an oncogenic pathogen-free status. Generally, the methods include obtaining abundance data, e.g., relative expression levels, for a plurality of genes that are differentially expressed in cancerous tissue associated with an oncogenic pathogen infections and the same type of cancerous tissue that is not associated with an oncogenic pathogen infection. The abundance data is then input into a classifier that is trained to discriminate between the first cancer condition and the second cancer condition, at least in part, based on the abundance of the genes that are differentially expressed in the two types of cancerous tissues. Examples of the training of such classifiers are provided above in conjunction with the description of FIG. 2.

Many of the embodiments described below, in conjunction with FIG. 3, relate to analyses performed using expression data from the exome of a cancer patient, e.g., obtained from a sample of the cancerous tissue in the patient. Generally, these embodiments are independent and, thus, not reliant upon any particular expression data generation methods, e.g., sequencing, hybridization, and/or qPCR methodologies. However, in some embodiments, the methods described below include one or more steps (301) of generating expression data.

In some embodiments, these methods include obtaining (302) a sample of the cancerous tissue. Method for obtaining samples of cancerous tissue are known in the art, and are dependent upon the type of cancer being sampled. For example, bone marrow biopsies and isolation of circulating tumor cells can be used to obtain samples of blood cancers, endoscopic biopsies can be used to obtain samples of cancers of the digestive tract, bladder, and lungs, needle biopsies (e.g., fine-needle aspiration, core needle aspiration, vacuum-assisted biopsy, and image-guided biopsy, can be used to obtain samples of subdermal tumors, skin biopsies, e.g., shave biopsy, punch biopsy, incisional biopsy, and excisional biopsy, can be used to obtain samples of dermal cancers, and surgical biopsies can be used to obtain samples of cancers affecting internal organs of a patient.

In some embodiments, mRNA is then isolated (304) from the sample of the cancerous tissue. Many techniques for RNA isolation from a tissue sample are known in the art. For example, acid guanidinium thiocyanate-phenol-chloroform extraction (see, for example, Chomczynski and Sacchi, Nat Protoc, 1(2):581-85 (2006), the content of which is incorporated herein by reference, in its entirety, for all purposes), and silica bead/glass fiber adsorption (see, for example, Poeckh, T. et al., Anal Biochem., 373(2):253-62 (2008), the content of which is incorporated herein by reference, in its entirety, for all purposes). The selection of any particular RNA isolation technique for use in conjunction with the embodiments described herein is well within the skill of the person having ordinary skill in the art, who will consider the tissue type, the state of the tissue, e.g., fresh, frozen, formalin-fixed, paraffin-embedded (FFPE), and the type of nucleic acid analysis that is to be performed with the RNA sample.

In some embodiments, RNA is isolated from blood samples and/or tissue sections (e.g., a tumor biopsy) using commercially available reagents, for example, proteinase K, TURBO DNase-I, and/or RNA clean XP beads. In some embodiments, the isolated RNA is subjected to a quality control protocol to determine the concentration and/or quantity of the RNA molecules, including the use of a fluorescent dye and a fluorescence microplate reader, standard spectrofluorometer, or filter fluorometer.

In some embodiments, expression data is obtained directly from the isolated mRNA, e.g., by direct RNA sequencing (314). Methods for direct RNA sequencing are well known in the art. See, for example, Ozsolak F., et al., Nature 461:814-18 (2009), and Garalde, D. R., et al., Nat Methods, 15(3):201-206 (2018), the contents of which are incorporated herein by reference, in their entireties, for all purposes.

In other embodiments, expression data is obtained through a cDNA intermediate. Accordingly, in some embodiments, the isolated RNA is used to create a cDNA library via cDNA synthesis (310). In some embodiments, cDNA libraries are prepared from isolated RNA that is purified and selected for cDNA molecule size selection using commercially available reagents, for example Roche KAPA Hyper Beads. In another example, a New England Biolabs (NEB) kit may be used.

In some embodiments, cDNA library preparation includes ligation of adapters onto the cDNA molecules. For example, UDI adapters, such as Roche SeqCap dual end adapters, or UMI adapters (for example, full length or stubby Y adapters) may be ligated to the cDNA molecules. Adapters are nucleic acid molecules that may serve as barcodes to identify cDNA molecules according to the sample from which they were derived and/or to facilitate the downstream bioinformatics processing and/or the next generation sequencing reaction. The sequence of nucleotides in the adapters may be specific to a sample in order to distinguish samples. The adapters may facilitate the binding of the cDNA molecules to anchor oligonucleotide molecules on the sequencer flow cell and may serve as a seed for the sequencing process by providing a starting point for the sequencing reaction.

cDNA libraries may be amplified and purified using reagents, for example, Axygen MAG PCR clean up beads. Then the concentration and/or quantity of the cDNA molecules may be quantified using a fluorescent dye and a fluorescence microplate reader, standard spectrofluorometer, or filter fluorometer.

In some embodiments, both for direct RNA sequencing and prior to cDNA library construction, the isolated RNA is first enriched (308) for a desired type of RNA (e.g., mRNA) or species (e.g., specific mRNA transcripts), prior to cDNA library construction. Methods of enriching for desired RNA molecules are also well known in the art. For example, mRNA molecules can be enriched, e.g., relative to other RNA molecules in a total RNA preparation, using oligo-dT affinity techniques (see, for example, Rio, D. C., et al., Cold Spring Harb Protoc., 2010 Jul. 1; 2010(7), the content of which is incorporated herein by reference, in its entirety, for all purposes). Specific mRNA transcripts can also be isolated, e.g., using hybridization probes that specifically bind to one or more mRNA sequences of interest.

In some embodiments, cDNA libraries are pooled and treated with reagents to reduce off-target capture, for example Human COT-1 and/or IDT xGen Universal Blockers, before being dried in a vacufuge. Pools may then be resuspended in a hybridization mix, for example, IDT xGen Lockdown, and probes may be added to each pool, for example, IDT xGen Exome Research Panel v1.0 probes, IDT xGen Exome Research Panel v2.0 probes, other IDT probe panels, Roche probe panels, or other probes. Pools may be incubated in an incubator, PCR machine, water bath, or other temperature-modulating device to allow probes to hybridize. Pools may then be mixed with Streptavidin-coated beads or another means for capturing hybridized cDNA-probe molecules, especially cDNA molecules representing exons of the human genome. In another embodiment, polyA capture may be used. Pools may be amplified and purified once more using commercially available reagents, for example, the KAPA HiFi Library Amplification kit and Axygen MAG PCR clean up beads, respectively.

cDNA library construction from isolated mRNAs is also well known in the art. In some embodiments, cDNA library construction is performed by first-strand DNA synthesis from the isolated mRNA using a reverse transcriptase, followed by second-strand synthesis using a DNA polymerase. Example methods for cDNA synthesis are described in McConnell and Watson, 1986, FEBS Lett. 195(1-2), pp. 199-202; Lin and Ying, 2003, Methods Mol Biol. 221, pp. 129-143, and Oh et al., 2003, Exp Mol Med. 35(6), pp. 586-90, the contents of which are hereby incorporated herein by reference, in their entireties, for all purposes.

The cDNA library may also be analyzed to determine the fragment size of cDNA molecules, which may be done through gel electrophoresis techniques and may include the use of a device such as a LabChip GX Touch. Pools may be cluster amplified using a kit (for example, Illumina Paired-end Cluster Kits with PhiX-spike in). In one example, the cDNA library preparation and/or whole exome capture steps may be performed with an automated system, using a liquid handling robot (for example, a SciClone NGSx).

The library amplification may be performed on a device, for example, an Illumina C-Bot2, and the resulting flow cell containing amplified target-captured cDNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. The next generation sequencer may generate a FASTQ, BCL, or other file for each patient sample or each flow cell.

If two or more patient samples are processed simultaneously on the same sequencer flow cell, reads from multiple patient samples may be contained in the same BCL file initially and then divided into a separate FASTQ file for each patient. A difference in the sequence of the adapters used for each patient sample could serve the purpose of a barcode to facilitate associating each read with the correct patient sample and placing it in the correct FASTQ file.

Methods for mRNA sequencing are well known in the art. In some embodiments, the mRNA sequencing is performed by whole exome sequencing (WES). Generally, WES is performed by isolating RNA from a tissue sample, optionally selecting for desired sequences and/or depleting unwanted RNA molecules, generating a cDNA library, and then sequencing the cDNA library (312), for example, using next generation sequencing (NGS) techniques. For a review of the use of whole exome sequencing techniques in cancer diagnosis, see, Serrati et al., 2016, Onco Targets Ther. 9, pp. 7355-7365, the content of which is hereby incorporated herein by reference, in its entirety, for all purposes.

Next generation sequencing methods are also well known in the art, including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference exome or reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. Non-limited examples of well-known software for assembling and managing transcriptome information from RNA-seq data include TopHat and Cufflinks, see, Trapnell et al., 2012, Nat Protoc. 7(3), pp. 562-578, the content of which is hereby incorporated herein by reference, in its entirety, for all purposes. See, also, Hintzsche et al., 2016, Int J Genomics 7983236, the content of which is hereby incorporated herein by reference, in its entirety, for all purposes.

In other embodiments, expression data is generated by hybridization (313) of the cDNA library, e.g., using a microarray. The use of microarray-based gene profiling to identify differential gene expression following pathogen infection is known in the art. For example, see, Adomas et al., 2008, Tree Physiol. 28(6), pp. 885-897, the content of which is hereby incorporated herein by reference, in its entirety, for all purposes. Similarly, in other embodiments, yet other methods for quantifying expression based on a cDNA library are used, for example, quantitative real-time PCR (RT-qPCR). See, for example, Wagner, 2013, Methods Mol Biol. 1027, pp. 19-45, the content of which is hereby incorporated herein by reference, in its entirety, for all purposes.

Figure 3:
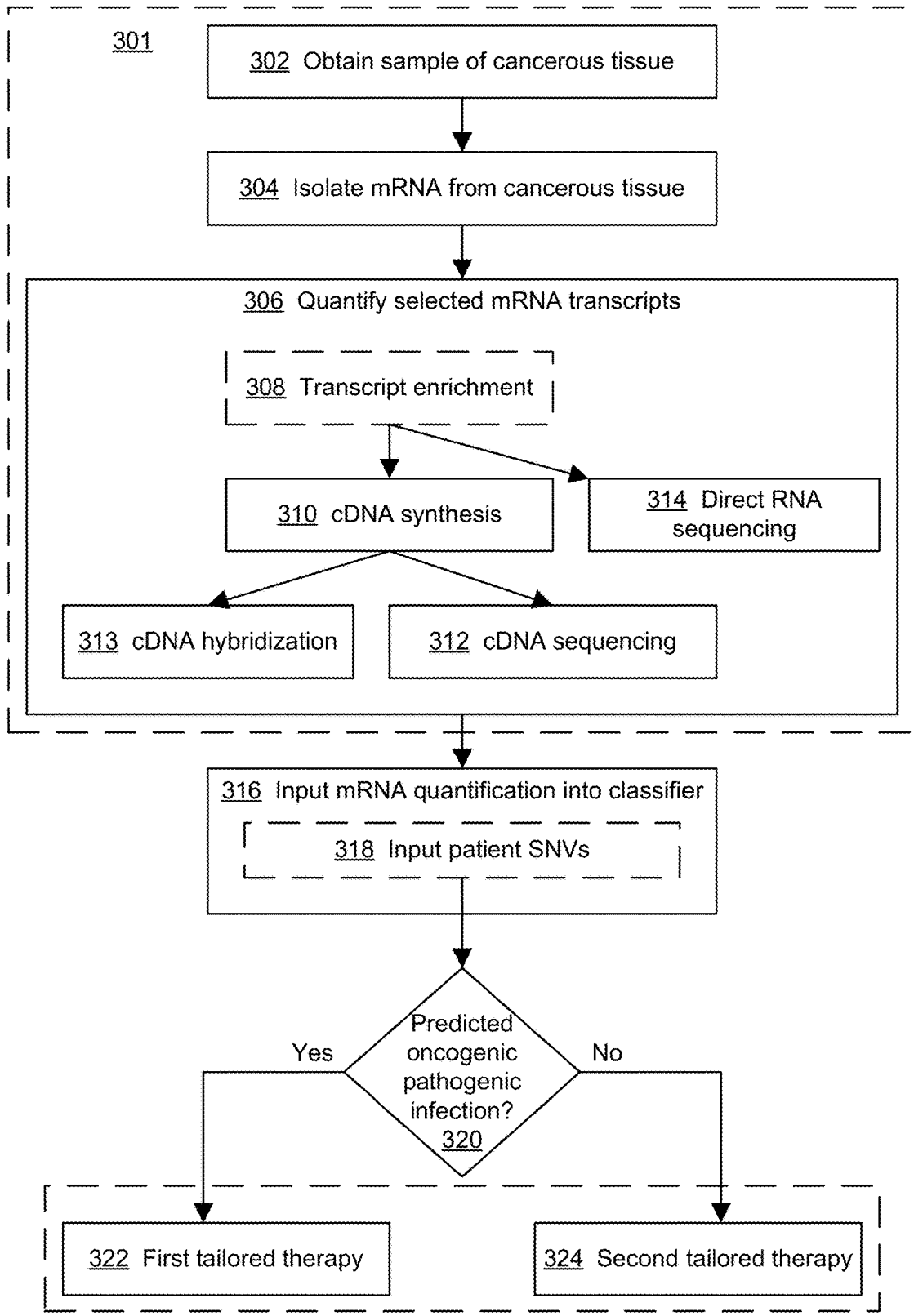
FIG. 3 provides a flow chart of processes and features for discriminate between a first cancer condition associated with infection by a first oncogenic pathogen and a second cancer condition associated with an oncogenic pathogen-free status, and optionally treating the cancer condition based on the oncogenic pathogen status of the cancer, in accordance with some embodiments of the present disclosure.

As illustrated with respect to FIG. 3, in some embodiments, method 300 is performed, at least partially, at a computer system (e.g., computer system 100 in FIG. 1) having one or more processors, and memory storing one or more programs for execution by the one or more processors for discriminating between a first cancer condition and a second cancer condition in a subject, where the first cancer condition is associated with infection by a first oncogenic pathogen and the second cancer condition is associated with an oncogenic pathogen-free status. Some operations in method 300 are, optionally, combined and/or the order of some operations is, optionally, changed.

In some embodiments, the method includes obtaining a dataset for the subject, the dataset including a plurality of abundance values, where each respective abundance value in the plurality abundance value quantifies a level of expression of a corresponding gene, in a plurality of genes, in a cancerous tissue from the subject. In some embodiments, the obtained abundance values are determined according to any of the methodologies described with respect to sub-method 301. In some embodiments, the abundance data is pre-generated and communicated to computer system 100 over a network, e.g., using network interface 104. Method 300 then includes inputting (316) the dataset to a classifier trained for discriminating between a first cancer condition and a second cancer condition in a human subject, where the first cancer condition is associated with infection by an oncogenic pathogen and the second cancer condition is associated with an oncogenic pathogen-free status. Examples of such classifiers are provided above in conjunction with FIG. 2. Thereby, the method determines (320) whether the subject has the first cancer condition, associated with the oncogenic pathogen infection, or the second cancer condition, that is not associated with the oncogenic pathogen infection.

In some embodiments, method 300 also include inputting a variant allele count for one or more variant alleles at one or more locus in the genome of the cancerous tissue from the subject into the classifier. That is, in some embodiments, the classifier is also trained against data relating to the presence or absence of one or more variant alleles in subjects with cancers that are either associated with an oncogenic pathogen infection or not associated with an oncogenic pathogen infection. In some embodiments, the one or more variant alleles are selected from variant alleles in a gene selected from the group consisting of TP53 (ENSG00000141510), CDKN2A (ENSG00000147889), and PIK3CA (ENSG00000121879).

In some embodiments, the subject is afflicted with breast cancer, lung cancer, prostate cancer, colorectal cancer, renal cancer, uterine cancer, pancreatic cancer, esophagus cancer, head/neck cancer, ovarian cancer, hepatobiliary cancer, cervical cancer, thyroid cancer, or bladder cancer.

In some embodiments, the first cancer condition is associated with infection by a first oncogenic pathogen selected from Epstein-Barr virus (EBV), hepatitis B virus (HBV), hepatitis C virus (HCV), human papilloma virus (HPV), human T-cell lymphotropic virus (HTLV-1), Kaposi's associated sarcoma virus (KSHV), and Merkel cell polyomavirus (MCV).

More specifically, in some embodiments, the first cancer condition is selected from cervical cancer associated with human papilloma virus (HPV), head and neck cancer associated with HPV, gastric cancer associated with Epstein-Barr virus (EBV), nasopharyngeal cancer associated with EBV, Burkitt lymphoma associated with EBV, Hodgkin lymphoma associated with EBV, liver cancer associated with hepatitis B virus (HBV), liver cancer associated with hepatitis C virus (HCV), Kaposi sarcoma associated with Kaposi's associated sarcoma virus (KSHV), adult T-cell leukemia/lymphoma associated with human T-cell lymphotropic virus (HTLV-1), and Merkel cell carcinoma associated with Merkel cell polyomavirus (MCV). For a summary of cancer conditions known to be associated with an oncogenic viral infection, see, de Flora, 2011, "The prevention of infection-associated cancers," Carcinogenesis 32, pp. 787-795.

Accordingly, when the first cancer condition is a particular type of cancer associated with a particular oncogenic pathogen, the second cancer condition is the same particular type of cancer associated with no infection of the particular oncolytic pathogen. For example, when the first cancer condition is cervical cancer associated with a human papilloma virus (HPV) infection, the second cancer condition is cervical cancer that is not associated with a human papilloma virus (HPV) infection. Further, as described above, the classifier used to discriminate between the two cancer conditions is trained against a dataset including at least gene abundance values (e.g., mRNA expression profiles) from subjects known to have cervical cancer associated with a human papilloma virus (HPV) infection and from subject known to have cervical cancer that is not associate with a human papilloma virus (HPV) infection.

In some embodiments, the method further includes treating the subject with either a first therapy (322) tailored for treatment of the first cancer condition, associated with the oncogenic pathogenic infection, or a second therapy (324) tailored for treatment of the second cancer condition, not associated with the oncogenic pathogen infection.

Accordingly, in one embodiment, a method is provided for treating a cancer in a human cancer patient. The method includes determining whether the patient is infected with an oncogenic pathogen linked to the pathology of the cancer by obtaining a dataset for the patient, the dataset including a plurality of abundance values, and inputting the dataset into a classifier trained to discriminate between at least a first cancer condition associated with an infection of the oncogenic pathogen and a second cancer condition that is not associated with an infection of the oncogenic pathogen. Each abundance value in the dataset quantifies a level of expression of a corresponding gene found to be differentially expressed in cancers associated with an infection of the oncogenic pathogen and cancers that are not associated with an infection of the oncogenic pathogen. In some embodiments, the genes for which abundance values are used to discriminate between cancer conditions for any particular type of cancer are selected according to any of the selection methodologies described above with reference to FIG. 2. Similarly, in some embodiments, the classifier used is trained according to any of the training methodologies described above with reference to FIG. 2.

In some embodiments, when the subject is determined to have a first cancer condition, associated with an oncogenic pathogen infection, the method includes assigning and/or administering immunotherapy to the subject. In some embodiments, when the subject is determined to have a second cancer condition, that is not associated with an oncogenic pathogen infection, the method includes assigning and/or administering chemotherapy to the subject.

As summarized in Table 2, several clinical trials are ongoing for the treatment of virally associated tumors. Accordingly, in some embodiments, the methods described herein include assigning and/or administering a treatment for a particular cancer associated with a particular oncogenic viral infection, as listed in Table 2. For example, in some embodiments, upon a determination that the subject has a phase 3 cervical cancer associated with an HPV infection, the subject is assigned and/or administered a therapeutically effective dosing regimen of axalimogene filolisbac, which is a live attenuated *Listeria monocytogenes* transfected with plasmids encoding the HPV-16E7 protein fused to a truncated fragment of the Lm protein listeriolysin O.

TABLE 2

Clinical trials for the treatment of cancers associated with oncogenic viral infections.

| Therapy | Mechanism of Action | Virus | Cancer/Stage of Development/ Clinical Trial |
|---|---|---|---|
| Axalimogene filolisbac (AXAL/ADXS11-001) | Therapeutic vaccine | HPV | Phase 3 cervical cancer (AIM2CERV; NCT02853604); Phase 2 NSCLC (NCT02531854); Phase ½ HNSCC (NCT02291055) |
| TG4001 | Therapeutic vaccine | HPV | Phase ½ HNSCC (NCT03260023) |
| GX-188E | Therapeutic vaccine | HPV | Phase ½ cervical cancer (NCT03444376) |
| VGX-3100 | Therapeutic vaccine | HPV | Phase 3 cervical cancer (REVEAL; NCT03185013); Phase 2 vulval cancer (NCT0318-684) |
| MEDI-0457 | Therapeutic vaccine | HPV | Phase 2 HPV+ cancer (NCT03439085); Phase ½ HNSCC (NCT03162224) |
| INO-3106 | Therapeutic vaccine | HPV | Phase 1 HPV+ cancers (NCT02241369) |
| TA-CIN | Therapeutic vaccine | HPV | Phase 1 cervical cancer (NCT02405221) |
| TA-HPV | Therapeutic vaccine | HPV | Phase 1 cervical cancer (NCT00788164) |
| ISA-101 | Therapeutic vaccine | HPV | Phase 2 HNSCC (NCT03258008) |

TABLE 2-continued

Clinical trials for the treatment of cancers associated with oncogenic viral infections.

| Therapy | Mechanism of Action | Virus | Cancer/Stage of Development/ Clinical Trial |
|---|---|---|---|
| PepCan | Therapeutic vaccine | HPV | Phase 2 cervical cancer (NCT02481414) |
| Nivolumab (Opdivo) | Immune checkpoint inhibitor | HPV | Phase 2 HNSCC (NCT03342911) |
| AMG319 | PI3K inhibitor | HPV | Phase 2 HNSCC (NCT02540928) |
| BKM120 | PI3K inhibitor | HPV | Phase 1 HNSCC (NCT02113878) |
| HPV-specific T cells | Adoptive cell therapy | HPV | Phase 1 HPV+ tumors (NCT02379520); Phase 1 vulvar cancers (NCT03197025) |
| ATA 129 | Adoptive cell therapy | EBV | Phase 3 EBV+ lymphoproliferative disease (NCT03394365/ALLELE, NCT03392142/MATCH) |
| EBVST | Adoptive cell therapy | EBV | Phase 3 EBV+ nasopharyngeal carcinoma (NCT02578641) |
| CMD-003 | Adoptive cell therapy | EBV | Phase 2 EBV+ lymphomas (NCT02763254, NCT01948180/CITADEL) |
| Ibrutinib | BTK inhibitor | EBV | Phase 2 EBV+ DLBCL (NCT02670616) |
| Pembrozilumab | Immune checkpoint inhibitor | EBV | Phase 2 EBV+ gastric cancer (NCT03257163); Phase 1 KSHV+ Kaposo sarcoma (NCT02595866) |
| Nivolumab | Immune checkpoint inhibitor | EBV | Phase 2 EBV+ lymphoproliferative disorders and NHL (NCT03258567) |
| Avelumab | Immune checkpoint inhibitor | MCV | Phase ½ MCV+ MCC (NCT02584829) |
| Talimogene laherparepvec | Vaccine | MCV | Phase 2 MCV+ MCC (NCT02819843) |
| Sapanisertib | mTOR inhibitor | MCV | Phase ½ MCV+ MCC (NCT02514824) |

HPV Oncogenic Viral Infections.

In some embodiments, the methods described herein relate to classification and/or treatment of cancers known to be associated with a human papillomavirus (HPV) infection. As reported in Example 3 below, the twenty-four genes listed in Table 3, and shown in FIG. 4B, were found to be differentially expressed in at least eight of the ten training sets formed from expression data of cervical or head and neck cancers with known HPV statuses in The Cancer Genome Atlas (TCGA). Accordingly, in some embodiments the expression levels of one or more of the genes listed in Table 3 are used for the classification of a cervical cancer or a head and neck cancer as either associated with an HPV infection or not associated with an HPV infection. In some embodiments, expression levels of at least 2, 3, 4, 5, 6, 7, 8, 9, 10, 11, 12, 13, 14, 15, 16, 17, 18, 19, 20, 21, 22, 23, or all 24 of the genes listed in Table 3 are used for the classification of a cervical cancer or a head and neck cancer as either associated with an HPV infection or not associated with an HPV infection.

TABLE 3

Genes found to be differentially expressed in at least 80% of the cervical cancer or head and neck cancer training sets derived from the TCGA database.

| ENSEMBL ACCESSION ID | GENE NAME |
|---|---|
| ENSG00000170442 | KRT86 |
| ENSG00000121005 | CRISPLD1 |
| ENSG00000134760 | DSG1 |
| ENSG00000149212 | SESN3 |
| ENSG00000173157 | ADAMTS20 |
| ENSG00000170549 | IRX1 |
| ENSG00000077935 | SMC1B |
| ENSG00000147889 | CDKN2A |
| ENSG00000108947 | EFNB3 |
| ENSG00000145824 | CXCL14 |
| ENSG00000105278 | ZFR2 |
| ENSG00000178222 | RNF212 |
| ENSG00000179455 | MKRN3 |
| ENSG00000196074 | SYCP2 |
| ENSG00000168530 | MYL1 |
| ENSG00000095777 | MYO3A |
| ENSG00000182545 | RNASE10 |
| ENSG00000144278 | GALNT13 |
| ENSG00000099625 | C19orf26 |
| ENSG00000145113 | MUC4 |
| ENSG00000254221 | PCDHGB1 |
| ENSG00000110092 | CCND1 |
| ENSG00000240386 | LCE1F |
| ENSG00000124134 | KCNS1 |

In one embodiment, a method is provided for discriminating between a first cancer condition and a second cancer condition in a human subject, wherein the first cancer condition is associated with infection by a human papillomavirus (HPV) oncogenic virus and the second cancer condition is associated with an HPV-free status. The method includes obtaining a dataset for the subject, e.g., as described above with reference to FIG. 3. The dataset includes a plurality of abundance values from the subject, where each respective abundance value in the plurality abundance value quantifies a level of expression of a corresponding gene, in a plurality of genes, in a cancerous tissue from the subject. In some embodiments, the plurality of genes includes at least five genes selected from the genes listed in table 3. The method then includes inputting the dataset to a classifier trained to discriminate between at least the first cancer condition and the second cancer condition based on the abundance values of the plurality of genes. In some embodiments, the classifier is trained in accordance with any of the methodologies described above, with respect to FIG. 2.

In some embodiments, the first cancer condition is cervical cancer associated with an HPV infection, and the second cancer condition is cervical cancer that is not associated with an HPV infection. In some embodiments, the first cancer condition is head and neck cancer associated with an HPV infection, and the second cancer condition is head and neck cancer that is not associated with an HPV infection. In some embodiments, the head and neck cancer is a specific form or head and neck cancer, e.g., hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, or salivary gland cancer.

In some embodiments, the plurality of genes includes at least ten of the genes listed in Table 3. In some embodiments, the plurality of genes includes at least fifteen of the genes listed in Table 3. In some embodiments, the plurality of genes includes at least twenty of the genes listed in Table 3. In some embodiments, the plurality of genes includes all of the genes listed in Table 3. In some embodiment, the plurality of genes includes one or more genes that are not listed in Table 3, e.g., 1, 2, 3, 4, 5, 6, 7, 8, 9, 10, or more of the genes not listed in Table 3. In some embodiments, the plurality of genes includes no more than 20 genes. In some embodiments, the plurality of genes includes no more than 25 genes. In some embodiments, the plurality of genes includes no more than 50 genes. In some embodiments, the plurality of genes includes no more than 10, 15, 20, 25, 30, 35, 40, 50, 60, 70, 80, 90, 100, 125, 150, 175, 200, 250, or 300 genes.

In some embodiments, the dataset also includes a variant allele count for one or more alleles at one or more locus in the genome of the cancerous tissue from the subject. In some embodiments, the variant allele count is either 1, representing a state in which the subject carries the variant allele, or 0, representing a state in which the subject does not carry the variant allele. In some embodiments, the variant allele is a somatic variant, originating from the germ line of the subject. In some embodiments, the variant allele is a cancer-derived variant, originating from the cancerous tissue. In some embodiments, the variant allele is located in the TP53 (ENSG00000141510) or CDKN2A (ENSG00000147889) gene.

In some embodiments, the classifier is trained for determining the HPV status of a test subject having an HPV-associated cancer selected from cervical cancer, head and neck squamous cell carcinoma, ovarian cancer, penile cancer, pharyngeal cancer, anal cancer, vaginal cancer, and vulvar cancer. In some embodiments, the classifier is trained for determining the HPV status of a test patient having a specific HPV-associated cancer, e.g., cervical cancer, head and neck squamous cell carcinoma, ovarian cancer, penile cancer, pharyngeal cancer, anal cancer, vaginal cancer, or vulvar cancer. However, as classifier training is generally improved by increasing the size of the training dataset, in some embodiments, the classifier is trained against data from patients that have two or more type of HPV-associated cancers, e.g., two, three, four, five, six, seven, or all eight of cervical cancer, head and neck squamous cell carcinoma, ovarian cancer, penile cancer, pharyngeal cancer, anal cancer, vaginal cancer, and vulvar cancer. In a particular embodiment, exemplified by Example 3, the classifier is trained against subjects having either head and neck squamous cell carcinoma or cervical cancer. However, in some embodiments, a classifier trained against patients having one or more types of HPV-associated cancer is useful for determining the HPV status of a patient having a different type of HPV-associated cancer.

In some embodiments, the features of the classifier include abundance values for a plurality of genes selected from those listed in Table 3, e.g., KRT86, CRISPLD1, DSG1, SESN3, DAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1. As reported below, e.g., in reference to Example 3, these twenty-four genes were found to be differentially expressed, dependent upon the HPV status of the subject, in at least eight of the ten training sets formed from expression data of cervical or head and neck cancers with known HPV statuses in The Cancer Genome Atlas (TCGA). However, the skilled artisan will appreciate that, is some instances, the use of different training data sets may yield different results, e.g., one or more of these genes may not be informative in at least 80% of training folds and/or one or more genes found not to be informative in at least 80% of training folds in the study reported in Example 3 may be informative. These differences may arise, for example, when different criteria are used to select the training population, e.g., different inclusion and/or exclusion criteria such as cancer type, personal characteristics (e.g., age, gender, ethnicity, family history, smoking status, etc.), or simply by using a smaller or larger data set.

Accordingly, in some embodiments, the features of the classifier include at least five of the genes listed in Table 3. In some embodiments, the features of the classifier include at least ten of the genes listed in Table 3. In some embodiments, the features of the classifier include at least fifteen of the genes listed in Table 3. In some embodiments, the features of the classifier include at least twenty of the genes listed in Table 3. In some embodiments, the features of the classifier include all twenty-four of the genes listed in Table 3. In some embodiments, the features of the classifier include 5, 6, 7, 8, 9, 10, 11, 12, 13, 14, 15, 16, 17, 18, 19, 20, 21, 22, 23, or all 24 of the genes listed in Table 3. Further, in some embodiments, the features of the classifier include the abundance values for one or more genes not listed in Table 3. In some embodiments, the features of the classifier include abundance values for 1, 2, 3, 4, 5, 6, 7, 8, 9, 10 or more genes not listed in Table 3. In some embodiments, the features of the classifier include the abundance values for 1-10 genes not listed in Table 3. In some embodiments, the features of the classifier include the abundance values for 1-5 genes not listed in Table 3. In other embodiments, the features of the classifier do not include the abundance values for any genes not listed in Table 3.

Further, the skilled artisan will also appreciate that some features, e.g., abundance values for a particular gene, will be more informative than other features in a particular classifier. One measure of the predictive power of respective features in a classifier based on multiple features is the regression coefficient calculated for the features during training of the model. Regression coefficients describe the relationship between each feature and the response of the model. The coefficient value represents the mean change in the response given a one-unit increase in the feature value. As such, at least for variables of the same type, the magnitude, e.g., absolute value, of a regression coefficient is correlated with the importance of the feature in the model. That is, the higher the magnitude of the regression coefficient, the more important the variable is to the model. For instance, as reported in Example 3, in a particular support vector machine (SVM) classifier trained against the abundance values of all twenty-four of the genes listed in Table 3, as well as a variant allele status for the TP53 and CDKN2A genes, only six of the 24 genes had regression coefficients with magnitudes of at least 0.5—CDKN2A (1.13), SMC1B (1.02), EFNB3 (−0.97), KCNS1 (0.74), CCND1 (−0.65), and RNF212 (0.517).

As such, the skilled artisan may select a feature set that includes less than all of the genes listed in Table 3 based, at least in part, upon the importance of the respective features in one or more classification models. For instance, in some embodiments, one or more genes with lower predictive power in a classification model may be left out during classifier training. For example, in some embodiments, the features of the classifier include at least the gene expression features listed in Table 5 with a regression coefficient of at least 0.5, e.g., CDKN2A, SMC1B, EFNB3, KCNS1, CCND1, and RNF212. In some embodiments, the features of the classifier include at least the gene expression features listed in Table 5 with a regression coefficient of at least 0.4. In some embodiments, the features of the classifier include at least the gene expression features listed in Table 5 with a regression coefficient of at least 0.3. In some embodiments, the features of the classifier include at least the gene expression features listed in Table 5 with a regression coefficient of at least 0.2. In some embodiments, the features of the classifier include at least the gene expression features listed in Table 5 with a regression coefficient of at least 0.1.

Similarly, the size of the feature set may be affected by which features are included and/or excluded. For instance, in some embodiments, if particular features having high predictive power are included in a classification model, fewer total features may be included in the model. For instance, in some embodiments, if the abundance values for SMC1B, CDKN2A, and EFNB3 are included in the model, the abundance values for no more than two of the other genes whose abundance values are used as features in Table 5 need to be included in the model. Accordingly, in some embodiments, the features of the classifier include abundance values for SMC1B, CDKN2A, and EFNB3, and at least two other genes whose abundance values are used as features in Table 5. In some embodiments, the features of the classifier include abundance values for SMC1B, CDKN2A, and EFNB3, and at least five other genes whose abundance values are used as features in Table 5. In some embodiments, the features of the classifier include abundance values for SMC1B, CDKN2A, and EFNB3, and at least ten other genes whose abundance values are used as features in Table 5. In some embodiments, the features of the classifier include abundance values for SMC1B, CDKN2A, and EFNB3, and at least fifteen other genes whose abundance values are used as features in Table 5.

Similarly, in some embodiments, if features having high predictive power are excluded from the classification model, more of the other features may be included in the model. For instance, in some embodiments, if the abundance values for one or more of SMC1B, CDKN2A, and EFNB3 are not included in the model, the abundance values for at least fifteen of the other whose abundance values are used as features in Table 5 are included in the model. In some embodiments, if the abundance values for one or more of SMC1B, CDKN2A, and EFNB3 are not included in the model, the abundance values for at least twenty of the other genes whose abundance values are used as features in Table 5 are included in the model. In some embodiments, if the abundance values for one or more of SMC1B, CDKN2A, and EFNB3 are not included in the model, the abundance values for at least 15, 16, 17, 18, 19, 20, or all 21 of the other genes whose abundance values are used as features in Table 5 are included in the model.

Of course, other metrics are also available for evaluating the importance of a feature in a model, such as standardized regression coefficients and change in R-squared when the feature is added to the model last.

When selecting a feature set, the skilled artisan will also consider the degree to which features are correlated to each other. Correlation is a statistical measure of how linearly dependent two variables are upon each other. As such, two correlated features provide duplicative information to a predictive model, which can be detrimental to a classifier. As such, there are several reasons why a correlated feature may be excluded from a model. For instance, removing a correlated feature will make the algorithm faster, as the larger the number of features in a classifier the more computations that need to be made. Removing a correlated feature may also remove harmful bias, arising from the correlation, from a model. Finally, removing a correlated feature may make the model more interpretable.

As such, the skilled artisan may select a feature set that includes less than all of the genes listed in Table 3 based, at least in part, upon the correlation between respective features in one or more classification models. In some embodiments, the selection to remove one or the other feature of a correlated feature set is informed by predictive powers of the two features, e.g., their respective regression coefficients. For example, the gene expression values for ENSG00000105278 (CXCL14) and ENSG00000077935 (SMC1B) are highly correlated in the feature set listed in Table 3 (correlation=0.718983175). Accordingly, in some embodiments, the feature set does not include either CXCL14 or SMC1B. In some embodiments, CXCL14, rather than SMC1B is excluded from the feature set because, as reported in Table 5, SMC1B has a higher regression coefficient (1.02) than CXCL14 (−0.29) in the SVM model described in Example 3.

As reported in Table 6, ten pairs of gene expression features have a correlation of at least 0.6. Accordingly, in some embodiments, a feature in at least one pair of features having a correlation of at least 0.6 is excluded from the model. In some embodiments, a feature in at least two pairs of features having a correlation of at least 0.6 is excluded from the model. In other embodiments, a feature in at least 3, 4, 5, 6, 7, 8, 9, or all 10 pairs of features having a correlation of at least 0.6 is excluded from the model. In some embodiments, an excluded feature is the feature in a pair of highly correlated features having the lower regression coefficient reported in Table 5. For instance, with reference to Table 6, the feature having the lower regression coefficient in each highly correlated pair (e.g., corresponding to a correlation of at least 0.6) are:

Pair 1=DSG1
Pair 2=ZFR2
Pair 3=RNF212
Pair 4=SYCP2

Pair 5=ZFR2
Pair 6=MYO3A
Pair 7=SYCP2
Pair 8=DSG1
Pair 9=KCNS1
Pair 10=ZFR2

Accordingly, in some embodiments, one or more of DSG1, ZFR2, RNF212, SYCP2, MYO3A, and KCNS1 are excluded from the features set on the basis that they are the least informative feature in a pair of highly correlated features.

However, in some embodiments, this selection process does not allow both features of a highly correlated pair of features to be excluded from the feature set, e.g., on the basis that both genes are the least informative feature in at least one of the highly correlated pairs of features. Thus, in some embodiments, one or more of SYCP2, MYO3A, and KCNS1 are not excluded from the feature set. Similarly, in some embodiments, this selection process does not allow highly informative features, e.g., features with regression coefficients of at least 0.5, to be excluded from the feature set. Thus, in some embodiments, one or both of RNF212 and KCNS1 are not excluded from the feature set.

Accordingly, in one embodiment, the feature set includes abundance values for at least KRT86, CRISPLD1, SESN3, DAMTS20, IRX1, SMC1B, CDKN2A, EFNB3, CXCL14, MKRN3, SYCP2, MYL1, MYO3A, RNASE10, GALNT13, C19orf26, MUC4, PCDHGB1, CCND1, LCE1F, and KCNS1.

Similarly, in one embodiment, the feature set includes abundance values for at least KRT86, CRISPLD1, SESN3, DAMTS20, IRX1, SMC1B, CDKN2A, EFNB3, CXCL14, RNF212, MKRN3, MYL1, RNASE10, GALNT13, C19orf26, MUC4, PCDHGB1, CCND1, LCE1F, and KCNS1.

Similarly, in one embodiment, the feature set includes abundance values for at least KRT86, CRISPLD1, SESN3, DAMTS20, IRX1, SMC1B, CDKN2A, EFNB3, CXCL14, RNF212, MKRN3, SYCP2, MYL1, MYO3A, RNASE10, GALNT13, C19orf26, MUC4, PCDHGB1, CCND1, LCE1F, and KCNS1.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

In some embodiments, the classifier has a specificity of at least 70% and a sensitivity of at least 70% for a validation data set of at least 50 data constructs, e.g., where none of the data constructs in the validation data set were used in the training of the classifier. In some embodiments, the classifier has a specificity of at least 75% and a sensitivity of at least 75% for a validation data set of at least 50 data constructs, e.g., where none of the data constructs in the validation data set were used in the training of the classifier. In some embodiments, the classifier has a specificity of at least 80% and a sensitivity of at least 80% for a validation data set of at least 50 data constructs, e.g., where none of the data constructs in the validation data set were used in the training of the classifier. In some embodiments, the classifier has a specificity of at least 85% and a sensitivity of at least 85% for a validation data set of at least 50 data constructs, e.g., where none of the data constructs in the validation data set were used in the training of the classifier. In some embodiments, the classifier has a specificity of at least 90% and a sensitivity of at least 90% for a validation data set of at least 50 data constructs, e.g., where none of the data constructs in the validation data set were used in the training of the classifier. In some embodiments, the classifier has a specificity of at least 95% and a sensitivity of at least 95% for a validation data set of at least 50 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 50 data constructs. In some embodiments, the classifier has a sensitivity of at least 70%, 75%, 80%, 85%, 90%, 95%, 96%, 97%, 98%, 99%, or higher for a validation data set of at least 50 data constructs.

In some embodiments, the classifier has a specificity of at least 70% and a sensitivity of at least 70% for a validation data set of at least 100 data constructs, e.g., where none of the data constructs in the validation data set were used in the training of the classifier. In some embodiments, the classifier has a specificity of at least 75% and a sensitivity of at least 75% for a validation data set of at least 100 data constructs, e.g., where none of the data constructs in the validation data set were used in the training of the classifier. In some embodiments, the classifier has a specificity of at least 80% and a sensitivity of at least 80% for a validation data set of at least 100 data constructs, e.g., where none of the data constructs in the validation data set were used in the training of the classifier. In some embodiments, the classifier has a specificity of at least 85% and a sensitivity of at least 85% for a validation data set of at least 100 data constructs, e.g., where none of the data constructs in the validation data set were used in the training of the classifier. In some embodiments, the classifier has a specificity of at least 90% and a sensitivity of at least 90% for a validation data set of at least 100 data constructs, e.g., where none of the data constructs in the validation data set were used in the training of the classifier. In some embodiments, the classifier has a specificity of at least 95% and a sensitivity of at least 95% for a validation data set of at least 100 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 100 data constructs. In some embodiments, the classifier has a sensitivity of at least 70%, 75%, 80%, 85%, 90%, 95%, 96%, 97%, 98%, 99%, or higher for a validation data set of at least 100 data constructs.

In some embodiments, the method further includes assigning therapy and/or administering therapy to the subject based on the classification of the cancer condition, e.g., based on whether or not the subject's cancer is associated with an HPV viral infection.

Accordingly, in one embodiment, a method is provided for treating cervical cancer in a human cancer patient. The method includes determining whether the human cancer patient is infected with a human papillomavirus (HPV) oncogenic virus by obtaining a dataset for the human cancer patient, the dataset including a plurality of abundance values where each respective abundance value in the plurality abundance value quantifies a level of expression of a corresponding gene, in a plurality of genes, and the plurality of genes includes at least five genes selected from the genes listed in Table 3. The method then includes inputting the dataset to a classifier trained to discriminate between at least a first cervical cancer condition associated with HPV infection and a second cervical cancer condition associated with an HPV-free status based on the abundance values of the plurality of genes, in a cancerous tissue of the subject. In some embodiments, the classifier is trained according to a methodology described above, referring to FIG. 2. The method then includes treating the cervical cancer. When the classifier result indicates that the human cancer patient is infected with an HPV oncogenic virus, administering a first therapy tailored for treatment of cervical cancer associated with an HPV infection. When the classifier result indicates that the human cancer patient is not infected with an HPV oncogenic virus, administering a second therapy tailored for treatment of cervical cancer not associated with an HPV infection.

In some embodiments, the plurality of genes includes at least ten of the genes listed in Table 3. In some embodiments, the plurality of genes includes at least fifteen of the genes listed in Table 3. In some embodiments, the plurality of genes includes at least twenty of the genes listed in Table 3. In some embodiments, the plurality of genes includes all of the genes listed in Table 3. In some embodiment, the plurality of genes includes one or more genes that are not listed in Table 3, e.g., 1, 2, 3, 4, 5, 6, 7, 8, 9, 10, or more of the genes not listed in Table 3. In some embodiments, the plurality of genes includes no more than 20 genes. In some embodiments, the plurality of genes includes no more than 25 genes. In some embodiments, the plurality of genes includes no more than 50 genes. In some embodiments, the plurality of genes includes no more than 10, 15, 20, 25, 30, 35, 40, 50, 60, 70, 80, 90, 100, 125, 150, 175, 200, 250, or 300 genes.

In some embodiments, the dataset also includes a variant allele count for one or more alleles at one or more locus in the genome of the cancerous tissue from the subject. In some embodiments, the variant allele count is either 1, representing a state in which the subject carries the variant allele, or 0, representing a state in which the subject does not carry the variant allele. In some embodiments, the variant allele is a somatic variant, originating from the germ line of the subject. In some embodiments, the variant allele is a cancer-derived variant, originating from the cancerous tissue. In some embodiments, the variant allele is located in the TP53 (ENSG00000141510) or CDKN2A (ENSG00000147889) gene.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

In some embodiments, the first therapy tailored for treatment of cervical cancer associated with an HPV infection is a therapeutic vaccine. In some embodiments, the therapeutic vaccine is selected from axalimogene filolisbac (Advaxis), TG4001 (Transgene), GX-188E (Genexine), VGX-3100 (Inovio), MEDI-0457 (Inovio), INO-3106 (Inovio), TA-CIN (Cancer Research Technology), TA-HPV (Cancer Research Technology), ISA-101 (Isa), and PepCan (University of Arkansas).

In some embodiments, the first therapy tailored for treatment of cervical cancer associated with an HPV infection is an adoptive cell therapy. In some embodiments, adoptive cell therapy includes the administration of HPV-specific T cells, for example, as described for clinical trial ID NCT02379520 or NCT03197025 (Baylor College of Medicine).

In some embodiments, the first therapy tailored for treatment of cervical cancer associated with an HPV infection is an immune checkpoint inhibitor. In some embodiments, the immune checkpoint inhibitor is nivolumab (Bristol-Myers Squibb).

In some embodiments, the first therapy tailored for treatment of cervical cancer associated with an HPV infection is a PI3K inhibitor. In some embodiments, the PI3K inhibitor is AMG319 (Amgen) or BKM120 (Novartis).

Similarly, in one embodiment, a method is provided for treating head and neck cancer in a human cancer patient. The method includes determining whether the human cancer patient is infected with a human papillomavirus (HPV) oncogenic virus by obtaining a dataset for the human cancer patient, the dataset including a plurality of abundance values where each respective abundance value in the plurality abundance value quantifies a level of expression of a corresponding gene, in a plurality of genes, and the plurality of genes includes at least five genes selected from the genes listed in Table 3. The method then includes inputting the dataset to a classifier trained to discriminate between at least a first head and neck cancer condition associated with HPV infection and a second head and neck cancer condition associated with an HPV-free status based on the abundance values of the plurality of genes, in a cancerous tissue of the subject. In some embodiments, the classifier is trained according to a methodology described above, referring to FIG. 2. The method then includes treating the head and neck cancer. When the classifier result indicates that the human cancer patient is infected with an HPV oncogenic virus, the method includes administering a first therapy tailored for treatment of head and neck cancer associated with an HPV infection. When the classifier result indicates that the human cancer patient is not infected with an HPV oncogenic virus, the method includes administering a second therapy tailored for treatment of head and neck cancer not associated with an HPV infection.

In some embodiments, the plurality of genes includes at least ten of the genes listed in Table 3. In some embodiments, the plurality of genes includes at least fifteen of the genes listed in Table 3. In some embodiments, the plurality of genes includes at least twenty of the genes listed in Table 3. In some embodiments, the plurality of genes includes all of the genes listed in Table 3. In some embodiment, the plurality of genes includes one or more genes that are not listed in Table 3, e.g., 1, 2, 3, 4, 5, 6, 7, 8, 9, 10, or more of the genes not listed in Table 3. In some embodiments, the plurality of genes includes no more than 20 genes. In some embodiments, the plurality of genes includes no more than 25 genes. In some embodiments, the plurality of genes includes no more than 50 genes. In some embodiments, the plurality of genes includes no more than 10, 15, 20, 25, 30, 35, 40, 50, 60, 70, 80, 90, 100, 125, 150, 175, 200, 250, or 300 genes.

In some embodiments, the dataset also includes a variant allele count for one or more alleles at one or more locus in the genome of the cancerous tissue from the subject. In some embodiments, the variant allele count is either 1, representing a state in which the subject carries the variant allele, or 0, representing a state in which the subject does not carry the variant allele. In some embodiments, the variant allele is a somatic variant, originating from the germ line of the subject. In some embodiments, the variant allele is a cancer-derived variant, originating from the cancerous tissue. In some embodiments, the variant allele is located in the TP53 (ENSG00000141510) or CDKN2A (ENSG00000147889) gene.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

In some embodiments, the first therapy tailored for treatment of head and neck cancer associated with an HPV infection is a therapeutic vaccine. In some embodiments, the therapeutic vaccine is selected from axalimogene filolisbac (Advaxis), TG4001 (Transgene), GX-188E (Genexine), VGX-3100 (Inovio), MEDI-0457 (Inovio), INO-3106 (Inovio), TA-CIN (Cancer Research Technology), TA-HPV (Cancer Research Technology), ISA-101 (Isa), and PepCan (University of Arkansas).

In some embodiments, the first therapy tailored for treatment of head and neck cancer associated with an HPV infection is an adoptive cell therapy. In some embodiments, adoptive cell therapy includes the administration of HPV-specific T cells, for example, as described for clinical trial ID NCT02379520 or NCT03197025 (Baylor College of Medicine).

In some embodiments, the first therapy tailored for treatment of head and neck cancer associated with an HPV infection is an immune checkpoint inhibitor. In some embodiments, the immune checkpoint inhibitor is nivolumab (Bristol-Myers Squibb).

In some embodiments, the first therapy tailored for treatment of head and neck cancer associated with an HPV infection is a PI3K inhibitor. In some embodiments, the PI3K inhibitor is AMG319 (Amgen) or BKM120 (Novartis).

HPV Probe Sets.

In some embodiments, the present disclosure provides probes for binding, enriching, and or detecting nucleic acid molecules, e.g., mRNA transcripts that are isolated from a cancerous tissue sample from a subject and/or cDNA molecules prepared from those mRNA transcripts, that are informative of whether the subject has a first cancer condition associated with an HPV oncogenic viral infection or a second cancer condition that is not associated with an HPV oncogenic viral infection. Generally, the probes include DNA, RNA, or a modified nucleic acid structure with a base sequence that is complementary of a nucleic acid molecule of interest. Accordingly, when the probe is designed to hybridize to an mRNA molecule isolated from the cancerous tissue, the probe will include a nucleic acid sequence that is complementary to the coding strand of the gene from which the transcript originated, i.e., the probe will include an antisense sequence of the gene. However, when the probe is designed to hybridize to a cDNA molecule, the probe can contain either a sequence that is complementary to the coding sequence of the gene of interest (an antisense sequence) or a sequence that is identical to the coding sequence of the gene of interest (a sense sequence), because the molecules in the cDNA library are double stranded.

In some embodiments, the probes include additional nucleic acid sequences that do not share any homology to the gene sequence of interest. For example, in some embodiments, the probes also include nucleic acid sequences containing an identifier sequence, e.g., a unique molecular identifier (UMI), e.g., that is unique to a particular cancerous tissue sample or cancer patient. Examples of identifier sequences are described, for example, in Kivioja et al., 2011, Nat. Methods 9(1), pp. 72-74 and Islam et al., 2014, Nat. Methods 11(2), pp. 163-66, the contents of which are hereby incorporated herein by reference, in their entireties, for all purposes. Similarly, in some embodiments, the probes also include primer nucleic acid sequences useful for amplifying the nucleic acid molecule of interest, e.g., using PCR. In some embodiments, the probes also include a capture sequence designed to hybridize to an anti-capture sequence for recovering the nucleic acid molecule of interest from the sample.

Likewise, in some embodiments, the probe includes a non-nucleic acid affinity moiety covalently attached to nucleic acid molecule that is complementary to the gene of interest, for recovering the nucleic acid molecule of interest. Non-limited examples of non-nucleic acid affinity moieties include biotin, digoxigenin, and dinitrophenol. In some embodiments, the probe is attached to a solid-state surface or particle, e.g., a dip-stick or magnetic bead, for recovering the nucleic acid of interest.

Accordingly, in one embodiment, the disclosure provides a plurality of nucleic acid probes for discriminating between a first cancer condition and a second cancer condition in a human subject, where the first cancer condition is associated with infection by a human papillomavirus (HPV) oncogenic virus and the second cancer condition is associated with an HPV-free status. The plurality of nucleic acid probes includes at least five nucleic acid probes, and each of the at least five nucleic acid probes includes a respective nucleic acid sequence that is identical or complementary to at least 10 consecutive bases of an RNA transcript of a different respective gene selected from the genes listed in Table 3.

In some embodiments, the plurality of nucleic acid probes includes at least ten probes with sequences that are complementary to or identical to sequences from different genes listed in Table 3. In some embodiments, the plurality of nucleic acid probes includes at least fifteen probes with sequences that are complementary to or identical to sequences from different genes listed in Table 3. In some embodiments, the plurality of nucleic acid probes includes at least twenty probes with sequences that are complementary to or identical to sequences from different genes listed in Table 3. In some embodiments, the plurality of nucleic acid probes includes probes with sequences that are complementary to or identical to sequences from all of the genes listed in Table 3. In some embodiments, the plurality of nucleic acid probes includes 2, 3, 4, 5, 6, 7, 8, 9, 10, 11, 12, 13, 14, 15, 16, 17, 18, 19, 20, 21, 22, 23, or 24 probes with sequences that are complementary to or identical to sequences from different genes listed in Table 3.

In some embodiments, the plurality of nucleic acid probes includes one or more probes that bind to a sequence of a gene that is not listed in Table 3. In some embodiments, the plurality of nucleic acid probes includes at least 2, 3, 4, 5, 6, 7, 8, 9, 10, or more probes that bind to a sequence of a gene that is not listed in Table 3. In some embodiments, the plurality of nucleic acid probes includes probes with sequences that bind to no more than 20 genes. In some embodiments, the plurality of nucleic acid probes includes probes with sequences that bind to no more than 25 genes. In some embodiments, the plurality of nucleic acid probes includes probes with sequences that bind to no more than 50 genes. In some embodiments, the plurality of nucleic acid probes includes probes with sequences that bind to no more than 10, 15, 20, 25, 30, 35, 40, 50, 60, 70, 80, 90, 100, 125, 150, 175, 200, 250, or 300 genes.

In some embodiments, each probe in the plurality of probes includes a nucleic acid sequence that is identical or complementary to at least 15 consecutive bases of an RNA transcript of interest, e.g., a transcript from a gene listed in Table 3. In some embodiments, each probe in the plurality of probes includes a nucleic acid sequence that is identical or complementary to at least 30 consecutive bases of an RNA transcript of interest, e.g., a transcript from a gene listed in Table 3. In some embodiments, each probe in the plurality of probes includes a nucleic acid sequence that is identical or complementary to at least 50 consecutive bases of an RNA transcript of interest, e.g., a transcript from a gene listed in Table 3. In some embodiments, each probe in the plurality of probes includes a nucleic acid sequence that is identical or complementary to at least 10, 15, 20, 25, 30, 35, 40, 50, 60, 70, 80, 90, 100, 125, 150, 175, 200, or more consecutive bases of an RNA transcript of interest, e.g., a transcript from a gene listed in Table 3.

EBV Oncogenic Viral Infections.

In some embodiments, the methods described herein relate to classification and/or treatment of cancers known to be associated with an Epstein-Barr virus (EBV) infection. As reported in Example 4, below, the twenty-four genes listed in Table 4, and shown in FIG. 5B, were found to be differentially expressed in at least eight of the ten training sets formed from expression data of gastric cancer with known EBV statuses in The Cancer Genome Atlas (TCGA). Accordingly, in some embodiments the expression levels of one or more of the genes listed in Table 4 are used for the classification of gastric cancer as either associated with an EBV infection or not associated with an EBV infection. In some embodiments, expression levels of at least 2, 3, 4, 5, 6, 7, 8, or all 9 of the genes listed in Table 4 are used for the classification of gastric cancer as either associated with an EBV infection or not associated with an EBV infection.

TABLE 4

Genes found to be differentially expressed in at least 80% of the gastric cancer training sets derived from the TCGA database.

| ENSEMBL ACCESSION ID | GENE NAME |
| --- | --- |
| ENSG00000111319 | SCNN1A |
| ENSG00000113722 | CDX1 |
| ENSG00000124249 | KCNK15 |
| ENSG00000126583 | PRKCG |
| ENSG00000135480 | KRT7 |
| ENSG00000145506 | NKD2 |
| ENSG00000151025 | GPR158 |
| ENSG00000165215 | CLDN3 |
| ENSG00000176083 | ZNF683 |

In one embodiment, a method is provided for discriminating between a first cancer condition and a second cancer condition in a human subject, wherein the first cancer condition is associated with infection by an Epstein-Barr virus (EBV) oncogenic virus and the second cancer condition is associated with an EBV-free status. The method includes obtaining a dataset for the subject, e.g., as described above with reference to FIG. 3. The dataset includes a plurality of abundance values from the subject, where each respective abundance value in the plurality abundance value quantifies a level of expression of a corresponding gene, in a plurality of genes, in a cancerous tissue from the subject. In some embodiments, the plurality of genes includes at least five genes selected from the genes listed in Table 4. The method then includes inputting the dataset to a classifier trained to discriminate between at least the first cancer condition and the second cancer condition based on the abundance values of the plurality of genes. In some embodiments, the classifier is trained in accordance with any of the methodologies described above, with respect to FIG. 2.

In some embodiments, the plurality of genes includes all of the genes listed in Table 4. In some embodiment, the plurality of genes includes one or more genes that are not listed in Table 4, e.g., 1, 2, 3, 4, 5, 6, 7, 8, 9, 10, or more of the genes not listed in Table 4. In some embodiments, the plurality of genes includes no more than 20 genes. In some embodiments, the plurality of genes includes no more than 25 genes. In some embodiments, the plurality of genes includes no more than 50 genes. In some embodiments, the plurality of genes includes no more than 10, 15, 20, 25, 30, 35, 40, 50, 60, 70, 80, 90, 100, 125, 150, 175, 200, 250, or 300 genes.

In some embodiments, the dataset also includes a variant allele count for one or more alleles at one or more locus in the genome of the cancerous tissue from the subject. In some embodiments, the variant allele count is either 1, representing a state in which the subject carries the variant allele, or 0, representing a state in which the subject does not carry the variant allele. In some embodiments, the variant allele is a somatic variant, originating from the germ line of the subject. In some embodiments, the variant allele is a cancer-derived variant, originating from the cancerous tissue. In some embodiments, the variant allele is located in the TP53 (ENSG00000141510) or PIK3CA (ENSG00000121879) gene.

In some embodiments, the classifier is trained for determining the EBV status of a test subject having an EBV-associated cancer selected from Burkitt's lymphoma, sinonasal angiocentric T-cell lymphoma, non-Hodgkin's lymphoma, Hodgkin's lymphoma, nasopharyngeal carcinoma, and gastric cancer. In some embodiments, the classifier is trained for determining the EBV status of a test patient having a specific EBV-associated cancer, e.g., Burkitt's lymphoma, sinonasal angiocentric T-cell lymphoma, non-Hodgkin's lymphoma, Hodgkin's lymphoma, nasopharyngeal carcinoma, or gastric cancer. However, as classifier training is generally improved by increasing the size of the training dataset, in some embodiments, the classifier is trained against data from patients that have two or more type of EBV-associated cancers, e.g., two, three, four, five, or all six of Burkitt's lymphoma, sinonasal angiocentric T-cell lymphoma, non-Hodgkin's lymphoma, Hodgkin's lymphoma, nasopharyngeal carcinoma, and gastric cancer. In a particular embodiment, exemplified by Example 4, the classifier is trained against patients having gastric cancer. However, in some embodiments, a classifier trained against patients having one or more types of EBV-associated cancer is useful for determining the EBV status of a patient having a different type of EBV-associated cancer.

In some embodiments, the features of the classifier include abundance values for a plurality of genes selected from those listed in Table 4, e.g., SCNN1A, CDX1, KCNK15, PRKCG, KRT7, NKD2, GPR158, CLDN3, and ZNF683. As reported below, e.g., in reference to Example 4, these nine genes were found to be differentially expressed, dependent upon the EBV status of the subject, in at least 80% of the gastric cancer training sets in The Cancer Genome Atlas (TCGA). However, the skilled artisan will appreciate that, is some instances, the use of different training data sets may yield different results, e.g., one or more of these genes may not be informative in at least 80% of training folds and/or one or more genes found not to be informative in at least 80% of training folds in the study reported in Example 4 may be informative. These differences may arise, for example, when different criteria are used to select the training population, e.g., different inclusion and/or exclusion criteria such as cancer type, personal characteristics (e.g., age, gender, ethnicity, family history, smoking status, etc.), or simply by using a smaller or larger data set.

Accordingly, in some embodiments, the features of the classifier include at least five of the genes listed in Table 4. In some embodiments, the features of the classifier include at least six of the genes listed in Table 4. In some embodiments, the features of the classifier include at least seven of the genes listed in Table 4. In some embodiments, the features of the classifier include at least eight of the genes listed in Table 4. In some embodiments, the features of the classifier include all nine of the genes listed in Table 4. Further, in some embodiments, the features of the classifier also include the abundance values for one or more genes not listed in Table 4. In some embodiments, the features of the classifier include the abundance value for 1, 2, 3, 4, 5, 6, 7, 8, 9, 10 or more genes not listed in Table 4. In some embodiments, the features of the classifier include the abundance values for 1-10 genes not listed in Table 4. In some embodiments, the features of the classifier include 1-5 genes not listed in Table 4. In other embodiments, the features of the classifier do not include the abundance values for any genes not listed in Table 4.

Further, the skilled artisan will also appreciate that some features, e.g., abundance values for a particular gene, will be more informative than other features in a particular classifier. One measure of the predictive power of respective features in a classifier based on multiple features is the regression coefficient calculated for the features during training of the model. Regression coefficients describe the relationship between each feature and the response of the model. The coefficient value represents the mean change in the response given a one-unit increase in the feature value. As such, at least for variables of the same type, the magnitude, e.g., absolute value, of a regression coefficient is correlated with the importance of the feature in the model. That is, the higher the magnitude of the regression coefficient, the more important the variable is to the model. For instance, as reported in Example 4, in a particular support vector machine (SVM) classifier trained against the abundance values of all nine of the genes listed in Table 4, as well as a variant allele status for the TP53 and PIK3CA genes, only four of the nine genes had regression coefficients with magnitudes of at least 0.75-SCNN1A (−1.26), KCNK15 (−1.04), KRT7 (−0.94), and CLDN3 (−1.68).

As such, the skilled artisan may select a feature set that includes less than all of the genes listed in Table 4 based, at least in part, upon the importance of the respective features in one or more classification models. For instance, in some embodiments, one or more genes with lower predictive power in a classification model may be left out during classifier training. For example, in some embodiments, the features of the classifier include at least the gene expression features listed in Table 5 with a regression coefficient of at least 0.75, e.g., SCNN1A (−1.26), KCNK15 (−1.04), KRT7 (−0.94), and CLDN3 (−1.68). In some embodiments, the features of the classifier include at least the gene expression features listed in Table 5 with a regression coefficient of at least 0.6.

Similarly, the size of the feature set may be affected by which features are included and/or excluded. For instance, in some embodiments, if particular features having high predictive power are included in a classification model, fewer total features may be included in the model. For instance, in some embodiments, if the abundance values for SCNN1A, KCNK15, KRT7, and CLDN3 are included in the model, the abundance values for no more than one of the other genes listed in Table 4 need to be included in the model. Accordingly, in some embodiments, the features of the classifier include abundance values for SCNN1A, KCNK15, KRT7, and CLDN3, and at least one other genes listed in Table 4. In some embodiments, the features of the classifier include abundance values for SCNN1A, KCNK15, KRT7, and CLDN3, and at least two other genes listed in Table 4. In some embodiments, the features of the classifier include abundance values for SCNN1A, KCNK15, KRT7, and CLDN3, and at least three other genes listed in Table 4. In some embodiments, the features of the classifier include abundance values for SCNN1A, KCNK15, KRT7, and CLDN3, and at least four other genes listed in Table 4.

Similarly, in some embodiments, if features having high predictive power are excluded from the classification model, more of the other features may be included in the model. For instance, in some embodiments, if the abundance values for one or more of SCNN1A, KCNK15, KRT7, and CLDN3 are not included in the model, the abundance values for at least four of the other genes listed in Table 4 are included in the model. In some embodiments, if the abundance values for one or more of SCNN1A, KCNK15, KRT7, and CLDN3 are not included in the model, the abundance values for all five of the other genes listed in Table 4 are included in the model.

Of course, other metrics are also available for evaluating the importance of a feature in a model, such as standardized regression coefficients and change in R-squared when the feature is added to the model last.

When selecting a feature set, the skilled artisan will also consider the degree to which features are correlated to each other. Correlation is a statistical measure of how linearly dependent two variables are upon each other. As such, two correlated features provide duplicative information to a predictive model, which can be detrimental to a classifier. As such, there are several reasons why a correlated feature may be excluded from a model. For instance, removing a correlated feature will make the algorithm faster, as the larger the number of features in a classifier the more computations that need to be made. Removing a correlated feature may also remove harmful bias, arising from the correlation, from a model. Finally, removing a correlated feature may make the model more interpretable. As such, the skilled artisan may select a feature set that includes less than all of the genes listed in Table 3 based, at least in part, upon the correlation between respective features in one or more classification models. For example, statistical analysis of the SVM model trained in Example 4 revealed that the gene expression values for ENSG00000135480 (KRT7) and ENSG00000124249 (KCNK15) were highly correlated (0.650). Accordingly, in some embodiments, the abundance value for one of KRT7 and KCNK15 are excluded from the feature set.

For example, in one embodiment, the feature set includes abundance values for at least SCNN1A, CDX1, KCNK15, PRKCG, NKD2, GPR158, CLDN3, and ZNF683. In another embodiment, the feature set includes abundance values for at least SCNN1A, CDX1, PRKCG, KRT7, NKD2, GPR158, CLDN3, and ZNF683.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

In some embodiments, the classifier has a specificity of at least 70% and a sensitivity of at least 70% for a validation data set of at least 50 data constructs, e.g., where none of the data constructs in the validation data set were used in the training of the classifier. In some embodiments, the classifier has a specificity of at least 75% and a sensitivity of at least 75% for a validation data set of at least 50 data constructs, e.g., where none of the data constructs in the validation data set were used in the training of the classifier. In some embodiments, the classifier has a specificity of at least 80% and a sensitivity of at least 80% for a validation data set of at least 50 data constructs, e.g., where none of the data constructs in the validation data set were used in the training of the classifier. In some embodiments, the classifier has a specificity of at least 85% and a sensitivity of at least 85% for a validation data set of at least 50 data constructs, e.g., where none of the data constructs in the validation data set were used in the training of the classifier. In some embodiments, the classifier has a specificity of at least 90% and a sensitivity of at least 90% for a validation data set of at least 50 data constructs, e.g., where none of the data constructs in the validation data set were used in the training of the classifier. In some embodiments, the classifier has a specificity of at least 95% and a sensitivity of at least 95% for a validation data set of at least 50 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 50 data constructs. In some embodiments, the classifier has a sensitivity of at least 70%, 75%, 80%, 85%, 90%, 95%, 96%, 97%, 98%, 99%, or higher for a validation data set of at least 50 data constructs.

In some embodiments, the classifier has a specificity of at least 70% and a sensitivity of at least 70% for a validation data set of at least 100 data constructs, e.g., where none of the data constructs in the validation data set were used in the training of the classifier. In some embodiments, the classifier has a specificity of at least 75% and a sensitivity of at least 75% for a validation data set of at least 100 data constructs, e.g., where none of the data constructs in the validation data set were used in the training of the classifier. In some embodiments, the classifier has a specificity of at least 80% and a sensitivity of at least 80% for a validation data set of at least 100 data constructs, e.g., where none of the data constructs in the validation data set were used in the training of the classifier. In some embodiments, the classifier has a specificity of at least 85% and a sensitivity of at least 85% for a validation data set of at least 100 data constructs, e.g., where none of the data constructs in the validation data set were used in the training of the classifier. In some embodiments, the classifier has a specificity of at least 90% and a sensitivity of at least 90% for a validation data set of at least 100 data constructs, e.g., where none of the data constructs in the validation data set were used in the training of the classifier. In some embodiments, the classifier has a specificity of at least 95% and a sensitivity of at least 95% for a validation data set of at least 100 data constructs, e.g., where none of the data constructs in the validation data set were used in the training of the classifier. In some embodiments, the classifier has a specificity of at least 70%, 75%, 80%, 85%, 90%, 95%, 96%, 97%, 98%, 99%, or higher for a validation data set of at least 100 data constructs. In some embodiments, the classifier has a sensitivity of at least 70%, 75%, 80%, 85%, 90%, 95%, 96%, 97%, 98%, 99%, or higher for a validation data set of at least 100 data constructs.

In some embodiments, the method further includes assigning therapy and/or administering therapy to the subject based on the classification of the cancer condition, e.g., based on whether or not the subject's cancer is associated with an EBV viral infection.

Accordingly, in one embodiment, a method is provided for treating gastric cancer in a human cancer patient. The method includes determining whether the human cancer patient is infected with an Epstein-Barr virus (EBV) oncogenic virus by obtaining a dataset for the human cancer patient, the dataset including a plurality of abundance values where each respective abundance value in the plurality abundance value quantifies a level of expression of a corresponding gene, in a plurality of genes, and the plurality of genes includes at least five genes selected from the genes listed in Table 4. The method then includes inputting the dataset to a classifier trained to discriminate between at least a first gastric cancer condition associated with an EBV infection and a second gastric cancer condition associated with an EBV-free status based on the abundance values of the plurality of genes, in a cancerous tissue of the subject. In some embodiments, the classifier is trained according to a methodology described above, referring to FIG. 2. The method then includes treating the gastric cancer. When the classifier result indicates that the human cancer patient is infected with an EBV oncogenic virus, administering a first therapy tailored for treatment of gastric cancer associated with an EBV infection. When the classifier result indicates that the human cancer patient is not infected with an EBV oncogenic virus, administering a second therapy tailored for treatment of gastric cancer not associated with an EBV infection.

In some embodiments, the plurality of genes includes all of the genes listed in Table 4. In some embodiment, the plurality of genes includes one or more genes that are not listed in Table 4, e.g., 1, 2, 3, 4, 5, 6, 7, 8, 9, 10, or more of the genes not listed in Table 4. In some embodiments, the plurality of genes includes no more than 20 genes. In some embodiments, the plurality of genes includes no more than 25 genes. In some embodiments, the plurality of genes includes no more than 50 genes. In some embodiments, the plurality of genes includes no more than 10, 15, 20, 25, 30, 35, 40, 50, 60, 70, 80, 90, 100, 125, 150, 175, 200, 250, or 300 genes.

In some embodiments, the dataset also includes a variant allele count for one or more alleles at one or more locus in the genome of the cancerous tissue from the subject. In some embodiments, the variant allele count is either 1, representing a state in which the subject carries the variant allele, or 0, representing a state in which the subject does not carry the variant allele. In some embodiments, the variant allele is a somatic variant, originating from the germ line of the subject. In some embodiments, the variant allele is a cancer-derived variant, originating from the cancerous tissue. In some embodiments, the variant allele is located in the TP53 (ENSG00000141510) or PIK3CA (ENSG00000121879) gene.

In some embodiments, as described above referring to FIG. 2, the classifier is a logistic regression algorithm, a neural network algorithm, a convolutional neural network algorithm, a support vector machine algorithm, a Naive Bayes algorithm, a nearest neighbor algorithm, a boosted trees algorithm, a random forest algorithm, a decision tree algorithm, or a clustering algorithm. In some embodiments, the classifier was trained according to a methodology described above, in reference to FIG. 2.

In some embodiments, the first therapy tailored for treatment of gastric cancer associated with an EBV infection is an adoptive cell therapy. In some embodiments, the adoptive cell therapy includes is ATA 129 (Atara), EBVST (Tessa), or CMD-003 (Cell Medica).

In some embodiments, the first therapy tailored for treatment of gastric cancer associated with an EBV infection is an immune checkpoint inhibitor. In some embodiments, the immune checkpoint inhibitor is Pembrozilumab (Merck) or nivolumab (Bristol-Myers Squibb).

In some embodiments, the first therapy tailored for treatment of gastric cancer associated with an EBV infection is a BTK inhibitor. In some embodiments, the BTK inhibitor is ibrutinib (Pharmacyclics).

Reporting

In some embodiments, the methods described herein include a step of generating a patient report for the cancer status of a test subject. The report may be presented to a patient, physician, medical personnel, or researcher in a digital copy (for example, a JSON object, a pdf file, or an image on a website or portal), a hard copy (for example, printed on paper or another tangible medium), as audio (for example, recorded or streaming), or in another format.

The report includes information related to the specific characteristics of the patient's cancer, e.g., detected genetic variants, epigenetic abnormalities, associated oncogenic pathogenic infection, and/or pathology abnormalities. In some embodiments, other characteristics of a patient's sample and/or clinical records are also included in the report. In some embodiments, report includes information about clinical trials for which the patient is eligible, therapies that are specific to the patient's cancer, and/or possible therapeutic adverse effects associated with the specific characteristics of the patient's cancer, e.g., the patient's genetic variations, epigenetic abnormalities, associated oncogenic pathogenic infections, and/or pathology abnormalities, or other characteristics of the patient's sample and/or clinical records.

In some embodiments, the results included in the report, and/or any additional results (for example, from the bioinformatics pipeline), are used to query a database of clinical data, for example, to determine whether there is a trend showing that a particular therapy was effective in treating (e.g., slowing or halting cancer progression) in other patients having the same or similar characteristics.

In some embodiments, the results are used to design cell-based studies of the patient's biology, e.g., tumor organoid experiments. For example, an organoid may be genetically engineered to have the same characteristics as the specimen and may be observed after exposure to a therapy to determine whether the therapy can reduce the growth rate of the organoid, and thus may be likely to reduce the growth rate of the patient associated with the specimen. Similarly, in some embodiments, the results are used to direct studies on tumor organoids derived directly from the patient. An example of such experimentation is described in U.S. Provisional Patent Application No. 62/944,292, filed on Dec. 5, 2019, the content of which is incorporated herein by reference, in its entirety, for all purposes.

Figure 7A:
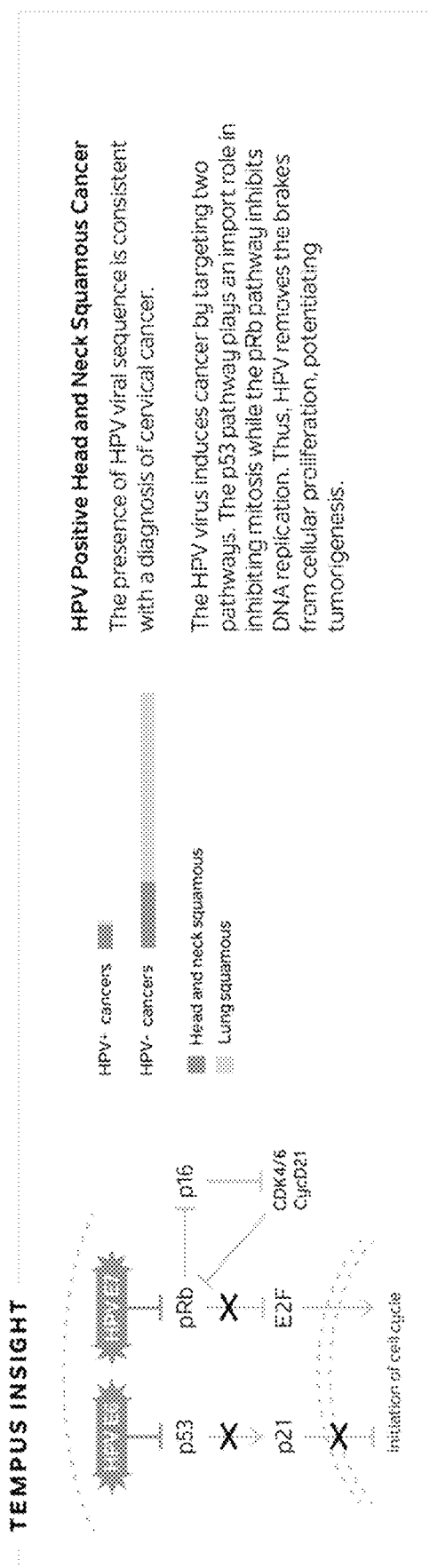
FIG. 7A illustrates an example report for an HPV positive head and neck squamous cancer, in accordance with some embodiments of the present disclosure.
Figure 7B:
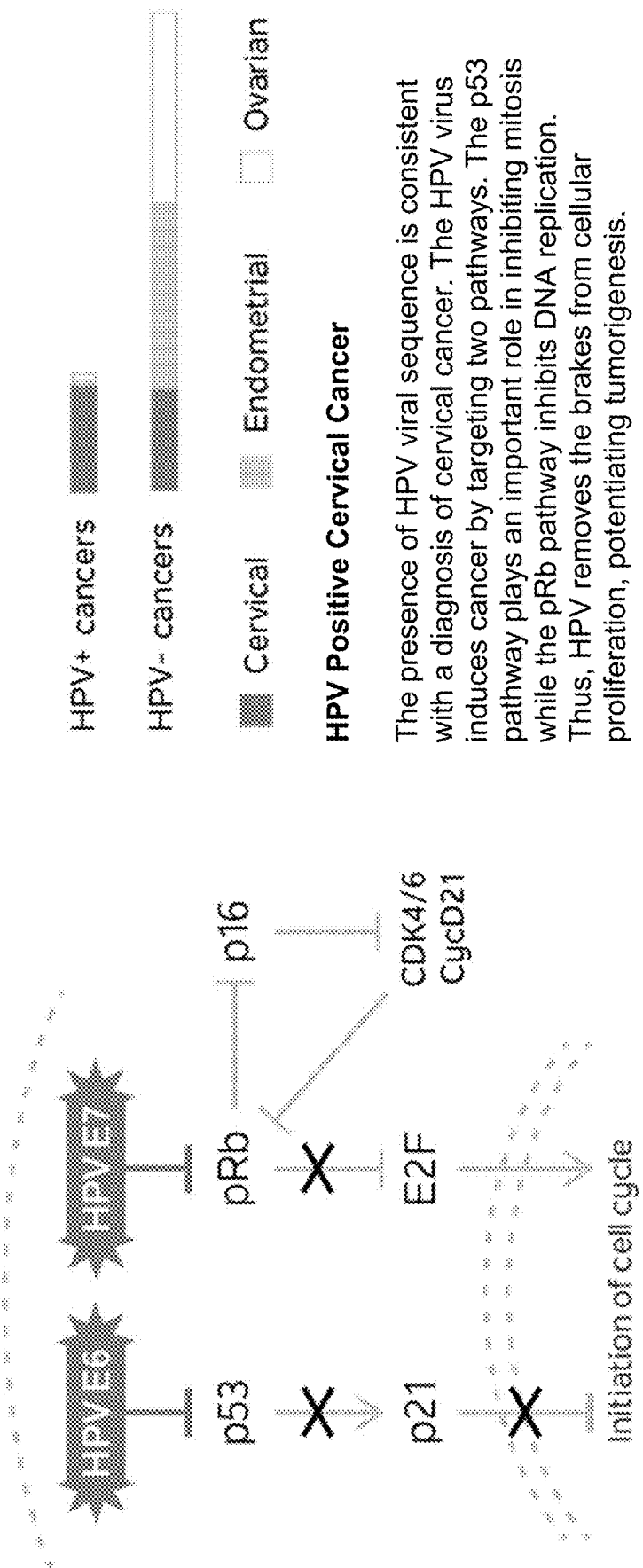
FIG. 7B illustrates an example report for an HPV positive cervical cancer, in accordance with some embodiments of the present disclosure.

In some embodiments, the patient report includes a section on the oncogenic pathogen infection status of the subject. For instance, FIGS. 7A and 7B illustrate example information provided upon diagnosis of HPV positive head and neck cancer and HPV positive cervical cancer, respectively.

EBV Probe Sets.

In some embodiments, the present disclosure provides probes for binding, enriching, and or detecting nucleic acid molecules, e.g., mRNA transcripts that are isolated from a cancerous tissue sample from a subject and/or cDNA molecules prepared from those mRNA transcripts, that are informative of whether the subject has a first cancer condition associated with an EBV oncogenic viral infection or a second cancer condition that is not associated with an EBV oncogenic viral infection. Generally, the probes include DNA, RNA, or a modified nucleic acid structure with a base sequence that is complementary of a nucleic acid molecule of interest. Accordingly, when the probe is designed to hybridize to an mRNA molecule isolated from the cancerous tissue, the probe will include a nucleic acid sequence that is complementary to the coding strand of the gene from which the transcript originated, e.g., the probe will include an antisense sequence of the gene. However, when the probe is designed to hybridize to a cDNA molecule, the probe can contain either a sequence that is complementary to the coding sequence of the gene of interest (an antisense sequence) or a sequence that is identical to the coding sequence of the gene of interest (a sense sequence), because the molecules in the cDNA library are double stranded.

In some embodiments, the probes include additional nucleic acid sequences that do not share any homology to the gene sequence of interest. For example, in some embodiments, the probes also include nucleic acid sequences containing an identifier sequence, e.g., a unique molecular identifier (UMI), e.g., that is unique to a particular cancerous tissue sample or cancer patient. Examples of identifier sequences are described, for example, in Kivioja et al., 2011, Nat. Methods 9(1):72-74 and Islam et al., 2014, Nat. Methods 11(2), pp. 163-66, the contents of which are incorporated herein by reference, in their entireties, for all purposes. Similarly, in some embodiments, the probes also include primer nucleic acid sequences useful for amplifying the nucleic acid molecule of interest, e.g., using PCR. In some embodiments, the probes also include a capture sequence designed to hybridize to an anti-capture sequence for recovering the nucleic acid molecule of interest from the sample.

Likewise, in some embodiments, the probe includes a non-nucleic acid affinity moiety covalently attached to nucleic acid molecule that is complementary to the gene of interest, for recovering the nucleic acid molecule of interest. Non-limited examples of non-nucleic acid affinity moieties include biotin, digoxigenin, and dinitrophenol. In some embodiments, the probe is attached to a solid-state surface or particle, e.g., a dip-stick or magnetic bead, for recovering the nucleic acid of interest.

Accordingly, in one embodiment, the disclosure provides a plurality of nucleic acid probes for discriminating between a first cancer condition and a second cancer condition in a human subject, where the first cancer condition is associated with infection by an Epstein-Barr virus (EBV) oncogenic virus and the second cancer condition is associated with an EBV-free status. The plurality of nucleic acid probes includes at least five nucleic acid probes, and each of the at least five nucleic acid probes includes a respective nucleic acid sequence that is identical or complementary to at least 10 consecutive bases of an RNA transcript of a different respective gene selected from the genes listed in Table 4.

In some embodiments, the plurality of nucleic acid probes includes at least ten probes with sequences that are complementary to or identical to sequences from different genes listed in Table 4. In some embodiments, the plurality of nucleic acid probes includes 2, 3, 4, 5, 6, 7, 8, or 9 probes with sequences that are complementary to or identical to sequences from different genes listed in Table 4.

In some embodiments, the plurality of nucleic acid probes includes one or more probes that bind to a sequence of a gene that is not listed in Table 4. In some embodiments, the plurality of nucleic acid probes includes at least 2, 3, 4, 5, 6, 7, 8, 9, 10, or more probes that bind to a sequence of a gene that is not listed in Table 4. In some embodiments, the plurality of nucleic acid probes includes probes with sequences that bind to no more than 20 genes. In some embodiments, the plurality of nucleic acid probes includes probes with sequences that bind to no more than 25 genes. In some embodiments, the plurality of nucleic acid probes includes probes with sequences that bind to no more than 50 genes. In some embodiments, the plurality of nucleic acid probes includes probes with sequences that bind to no more than 10, 15, 20, 25, 30, 35, 40, 50, 60, 70, 80, 90, 100, 125, 150, 175, 200, 250, or 300 genes.

In some embodiments, each probe in the plurality of probes includes a nucleic acid sequence that is identical or complementary to at least 15 consecutive bases of an RNA transcript of interest, e.g., a transcript from a gene listed in Table 4. In some embodiments, each probe in the plurality of probes includes a nucleic acid sequence that is identical or complementary to at least 30 consecutive bases of an RNA transcript of interest, e.g., a transcript from a gene listed in Table 4. In some embodiments, each probe in the plurality of probes includes a nucleic acid sequence that is identical or complementary to at least 50 consecutive bases of an RNA transcript of interest, e.g., a transcript from a gene listed in Table 4. In some embodiments, each probe in the plurality of probes includes a nucleic acid sequence that is identical or complementary to at least 10, 15, 20, 25, 30, 35, 40, 50, 60, 70, 80, 90, 100, 125, 150, 175, 200, or more consecutive bases of an RNA transcript of interest, e.g., a transcript from a gene listed in Table 4.

Digital and Laboratory Health Care Platform

In some embodiments, the methods and systems described above are utilized in combination with, or as part of, a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting diagnosis and treatment selection for cancers associated with oncogenic pathogen infections. Embodiments may include a single microservice for executing and delivering diagnosis and treatment selection for cancers associated with oncogenic pathogen infections or may include a plurality of microservices each having a particular role, which together implement one or more of the embodiments above. In one example, a first microservice may execute classification in order to deliver a diagnosis to a second microservice for recommending appropriate treatment modalities for a cancer associated with an oncogenic pathogen infection. Similarly, the second microservice may execute therapeutic analysis to deliver recommended therapeutic modalities, according to an embodiment, above.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A microservices-based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for classifying an oncogenic pathogen status of a cancer has been received and is ready for processing. The first microservice may execute and notify the order management system once the delivery of the classification is ready for the second microservice. Furthermore, the order management system may identify that execution parameters (prerequisites) for the second microservice are satisfied, including that the first microservice has completed, and notify the second microservice that it may continue processing the order to recommend appropriate treatment modalities for a cancer associated with an oncogenic pathogen infection, according to an embodiment, above.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. In one example, targeted panels may enable the delivery of next generation sequencing results for detecting an oncogenic pathogen infection according to an embodiment, above. An example of the design of next-generation sequencing probes is disclosed, for example, in U.S. Prov. Patent Application No. 62/924,073, titled "Systems and Methods for Next Generation Sequencing Uniform Probe Design", and filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce a classification for the oncogenic pathogen status of the subject as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT19/69161, both titled "Transcriptome Deconvolution of Metastatic Tissue Samples", and filed Dec. 31, 2019, U.S. Prov. Patent Application No. 62/924,054, titled "Calculating Cell-type RNA Profiles for Diagnosis and Treatment", and filed Oct. 21, 2019, and U.S. Prov. Patent Application No. 62/944,995, titled "Rapid Deconvolution of Bulk RNA Transcriptomes for Large Data Sets (Including Transcriptomes of Specimens Having Two or More Tissue Types)", and filed Dec. 6, 2019 which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. Prov. Patent Application No. 62/855,750, titled "Systems and Methods for Multi-Label Cancer Classification", and filed May 31, 2019, which is incorporated herein by reference and in its entirety for all purposes. An example of an HLA LOH engine is disclosed, for example, in U.S. Prov. Patent Application No. 62/889,510, titled "Detection of Human Leukocyte Antigen Loss of Heterozygosity", and filed Aug. 20, 2019, which is incorporated herein by reference and in its entirety for all purposes. An example of a tumor mutational burden (TMB) engine is disclosed, for example, in U.S. Prov. Patent Application No. 62/804,458, titled "Assessment of Tumor Burden Methodologies for Targeted Panel Sequencing", and filed Feb. 12, 2019, which is incorporated herein by reference and in its entirety for all purposes. An example of a PD-L1 status engine is disclosed, for example, in U.S. Prov. Patent Application No. 62/854,400, titled "A Pan-Cancer Model to Predict The PD-L1 Status of a Cancer Cell Sample Using RNA Expression Data and Other Patient Data", and filed May 30, 2019, which is incorporated herein by reference and in its entirety for all purposes. An additional example of a PD-L1 status engine is disclosed, for example, in U.S. Prov. Patent Application No. 62/824,039, titled "PD-L1 Prediction Using H&E Slide Images", and filed Mar. 26, 2019, which is incorporated herein by reference and in its entirety for all purposes. An example of a homologous recombination deficiency engine is disclosed, for example, in U.S. Prov. Patent Application No. 62/804,730, titled "An Integrative Machine-Learning Framework to Predict Homologous Recombination Deficiency", and filed Feb. 12, 2019, which is incorporated herein by reference and in its entirety for all purposes. An example of a cellular pathway activation report engine is disclosed, for example, in U.S. Prov. Patent Application No. 62/888,163, titled "Cellular Pathway Report", and filed Aug. 16, 2019, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. Prov. Patent Application No. 62/931,600, titled "Systems and Methods for Detecting Microsatellite Instability of a Cancer Using a Liquid Biopsy", and filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944,292, titled "Large Scale Phenotypic Organoid Analysis", filed Dec. 5, 2019, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

EXAMPLES

Example 1—the Cancer Genome Atlas (TCGA)

The data used to train the classifiers presented in Examples 2 and 3 below was obtained from The Cancer Genome Atlas (TCGA). Briefly, the TCGA dataset is a publicly available dataset comprising more than two petabytes of genomic data for over 11,000 cancer patients, including clinical information about the cancer patients, metadata about the samples (e.g. the weight of a sample portion, etc.) collected from such patients, histopathology slide images from sample portions, and molecular information derived from the samples (e.g. mRNA/miRNA expression, protein expression, copy number, etc.). The TCGA dataset includes data on 33 different cancers: breast (breast ductal carcinoma, bread lobular carcinoma) central nervous system (glioblastoma multiforme, lower grade glioma), endocrine (adrenocortical carcinoma, papillary thyroid carcinoma, paraganglioma & pheochromocytoma), gastrointestinal (cholangiocarcinoma, colorectal adenocarcinoma, esophageal cancer, liver hepatocellular carcinoma, pancreatic ductal adenocarcinoma, and stomach cancer), gynecologic (cervical cancer, ovarian serous cystadenocarcinoma, uterine carcinosarcoma, and uterine corpus endometrial carcinoma), head and neck (head and neck squamous cell carcinoma, uveal melanoma), hematologic (acute myeloid leukemia, Thymoma), skin (cutaneous melanoma), soft tissue (sarcoma), thoracic (lung adenocarcinoma, lung squamous cell carcinoma, and mesothelioma), and urologic (chromophobe renal cell carcinoma, clear cell kidney carcinoma, papillary kidney carcinoma, prostate adenocarcinoma, testicular germ cell cancer, and urothelial bladder carcinoma).

Example 2—RNA Expression Profiling

Referring to FIG. 3, the expression profile of genes useful for determining HPV viral status was determined from a tumor sample of a head and neck cancer.

In accordance with block 302 of FIG. 3, a tumor biopsy of a head and neck cancer was obtained from a cancer patient, using a biopsy technique as described herein. The biopsy was flash frozen in liquid nitrogen shortly after removal from the patient.

In accordance with block 304 of FIG. 3, mRNA was isolated from the tumor sample. Briefly, the sample tissue block was removed from the liquid nitrogen, and a 5 mm×5 mm×5 mm block of the sample was removed and dissected using a cold knife. The dissected sample was mixed with TRIzol reagent (Chomczynski and Sacchi, 1987, Anal Biochem. 162(1), pp. 156-59, the content of which is incorporated herein by reference in its entirety, for all purposes) and homogenized by three short cycles, e.g., 60 seconds, 30 seconds, and 30 seconds, using a tissue homogenizer. Chloroform was added to the homogenized tumor sample, and the reaction was mixed. After phase separation, the aqueous phase of the reaction was removed and mixed with equal parts isopropanol, to precipitate the RNA. The reaction was centrifuged to pellet the RNA, the supernatant was removed. The pellet was washed twice with cold ethanol and then air dried. The extracted RNA was then re-suspended in RNase-free water.

Referring to block 306 of FIG. 3, mRNA in the isolated RNA was then quantified by whole exome sequencing. In accordance with block 308 of FIG. 3, mRNA was isolated from the extracted RNA by annealing to magnetic oligo (dT)—conjugated beads by heating the extracted RNA to disrupt secondary structures, and then incubating the RNA with the oligo(dT)—conjugated beads with the denatured RNA at room temperature in hybridization buffer. The beads were recovered and washed twice with hybridization buffer. The hybridized mRNA was then eluted by heating and recovered from the reaction.

In accordance with block 310 of FIG. 3, a cDNA library was constructed from the isolated mRNA. Briefly, divalent cations were added to the isolated mRNA to fragment the molecules at high temperature. The fragmented mRNA was precipitated by incubating at −80° C. in ethanol at pH 5.2, using glycogen as a carrier molecule. The mRNA was pelleted by centrifugation, washed with 70% ethanol, air dried, then re-suspended in RNase-free water. First strand DNA synthesis was performed using random primers and a reverse transcriptase enzyme. Second strand DNA synthesis was then performed using a DNA polymerase in the presence of RNaseH, to form double stranded cDNA. 5'-overhangs created by the second strand synthesis were repaired using T4 and Klenow DNA polymerases, to form blunt ends. The 3'-ends of the blunt-end cDNA were adenylated using Klenow DNA polymerase. Adapters were ligated to the ends of the adenylated cDNA using T4 DNA ligase, and the cDNA templates were purified and sized by agarose electrophoresis. Optionally, the purified cDNA templates are enriched by PCR amplification, thereby forming the final cDNA library.

In accordance with block 312 of FIG. 3, whole exome sequencing of the cDNA library was performed using the integrated DNA technologies (IDT) XGEN® LOCKDOWN® technology with the xGen Exome Research Panel. Briefly, the xGen Exome Research Panel covers 51 Mb of end-to-end tiled probe space of the human genome, providing deep and uniform coverage for whole exome target capture. The cDNA library was hybridized to biotinylated-DNA capture probes covering a reference human exome. The hybridized probes were recovered by binding to streptavidin beads. Post-capture PCR was performed to enrich the captured sequences. The amplified products were then sequenced using sequencing by synthesis (SBS) technology (Bently et al., 2008, Nature 456(7218), pp. 53-59, the content of which is hereby incorporated herein by reference, in its entirety, for all purposes).

The RNA sequencing data was then normalized using gene length data, guanine-cytosine (GC) content data, and depth of sequencing data, by normalizing the gene length data for at least one gene to reduce systematic bias, normalizing the GC content data for the at least one gene to reduce systematic bias, and normalizing the depth of sequencing data for each sample, as described in U.S. Provisional Application Ser. No. 62/735,349 and U.S. patent application Ser. No. 16/581,706, the contents of which are hereby incorporated herein by reference, in their entireties, for all purposes. The RNA sequencing data was also corrected against a standard gene expression dataset by comparing the sequence data for at least one gene in the gene expression dataset to sequence data in the standard gene expression dataset, as described in U.S. Provisional Application Ser. No. 62/735,349 and U.S. patent application Ser. No. 16/581, 706. The normalized and corrected RNA expression data for the twenty-four genes identified in Table 3, as well as the patient's CDKN2A and TP53 allele statuses, were then input into the HPV detection classifier trained in Example 3, to determine the HPV viral status of the patient.

Example 3—Human Papilloma Virus Detection

Referring to FIGS. 4A through 4D, a classifier for determining HPV viral status was trained using gene expression from the tumor RNA-seq data of a training population, where each subject in the training population had been diagnosed with head and neck squamous cell carcinoma or with cervical cancer.

In accordance with block 204 of FIG. 2A, a training dataset was obtained. Here, the dataset comprised a corresponding plurality of abundance values for each subject in the TCGA, described in Example 1, that had cervical cancer or head and neck cancer with known HPV status. As illustrated in FIG. 4A, there were 427 subjects in the TCGA that satisfied these selection criteria and thus served as the plurality of subjects of the training dataset. Of the 427 subjects, 263 had head and neck cancer and 164 has cervical cancer. Of the 263 subjects that had head and neck cancer, 32 tested positive for HPV and 231 tested negative for HPV. Of the 164 subjects that had cervical cancer, 156 tested positive for HPV and 8 tested negative for HPV. Thus, of the 427 subjects, 188 subjects were deemed to have the first cancer condition (afflicted with HPV and having head and neck, or cervical cancer) and the remaining 239 subjects were deemed to have the second cancer condition (not afflicted with HPV, but having head and neck, or cervical cancer).

Next, in accordance with block 218 of FIG. 2C and block 228 of FIG. 2D, the gene expression values from whole exome RNA data in the TCGA dataset for the 427 subjects was used to identify a discriminating gene set by regression, in which the gene expression values obtained from whole exome mRNA expression data for the 427 subjects in the TCGA dataset served as independent variables and the indication of whether a respective subject had the first cancer condition (afflicted with HPV and having head and neck, or cervical cancer) or the second cancer condition (not afflicted with HPV, but having head and neck, or cervical cancer) served as the dependent variable. More specifically, in accordance with block 228 of FIG. 2D, the dataset consisting of 427 subjects was split into ten sets (ten splits). Each set included two or more subjects afflicted with the first cancer condition and two or more subjects afflicted with the second cancer condition. Each respective set of the ten sets (splits) was independently subjected to regression in which whole exome mRNA expression data for the subjects of the respective set served as independent variables and the indication of whether a respective subject in the respective set had the first or second cancer condition served as the dependent variable. Each regression (split) was performed with L1 (LASSO) regularization in accordance with block 238 of FIG. 2E. Since L1 regularization leads to sparse coefficients, only a small subset of genes had non-zero coefficients for each set. Only the genes with non-zero coefficients in more than 80% of the sets were included in the final model. In other words, only those genes that had non-zero regression coefficients for at least eight of the ten sets (splits) were accepted into the discriminating set of genes on the basis of their expression data. The list of genes that satisfied this requirement are the ones listed in FIG. 4B in which the feature type is "gene expression." Furthermore, FIG. 6A illustrates principal component analysis of the abundance values of the genes listed in FIG. 4B across the training set. FIG. 6A illustrates that a plot of the first and second PCA values for each of the subjects in the training set break out into two distinct groups, corresponding to the first cancer condition (group 602) and second cancer condition (604), indicating the power of the abundance values of the genes listed in FIG. 4B to discriminate between the first and second cancer state.

In some embodiments, additional genes were included in the discriminating set of genes based on the presence or absence of mutations (e.g., the number of mutations) in the additional genes. In this example, as detailed in FIG. 4B, the genes CDKN2A and TP53 were included in the discriminating set of genes and the feature for these genes was the number of times mutations were observed in these genes in each of the respective 427 subjects of the training set.

Next, in accordance with block 242 of FIG. 2E, the respective abundance values for the discriminating gene set and the respective indication of cancer condition across the 427 subjects was used to train a classifier to discriminate between the first and second cancer conditions as a function of respective abundance values for the discriminating gene set. In a first model, the classifier used was a logistic regression classifier with a L1 regularization, in which the training was the 427 subjects but only using TCGA gene abundance levels for the genes listed in FIG. 4B for which the feature is "gene expression." In a second model, the classifier used was a logistic regression classifier with a L1 regularization, in which the training was on the 427 subjects using the TCGA gene abundance levels for the genes listed in FIG. 4B for which the feature is "gene expression" as well as TCGA mutation counts for the two genes in FIG. 4B for which the feature is "number of mutations." In a third model, the classifier used was a support vector machine (SVM) classifier from Scikit-learn, as disclosed in Pedregosa et al. 2011, "Machine Learning in Python," JMLR 12, pp. 2825-2830, hereby incorporated by reference, in which the training was on the 427 subjects but only using the TCGA gene abundance levels for the genes listed in FIG. 4B for which the feature is "gene expression." When validated against data from a cohort of 133 subjects with cervical cancer or head and neck cancer and a known HPV status, the classifier performed with a specificity of 92.5% and a sensitivity of 89.7%.

Figure 4C:
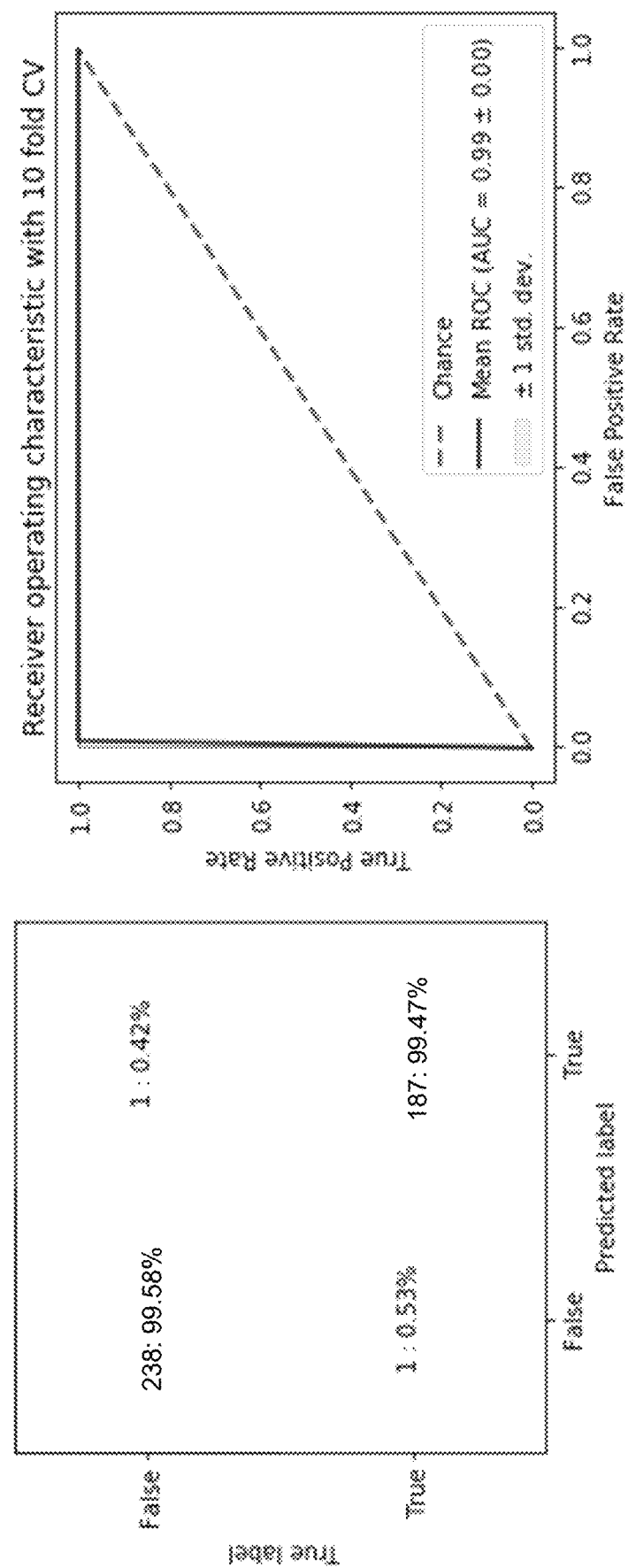
FIG. 4C illustrates performance metrics for a trained support vector machine, against the training dataset, for discriminating between a first cancer condition associated with an HPV oncogenic viral infection and a second cancer condition not associated with an HPV oncogenic viral infection, in accordance with some embodiments of the present disclosure.

In a fourth model, the classifier used was this same SVM classifier, in which the training was on the 427 subjects using the TCGA gene abundance levels for the genes listed in FIG. 4B for which the feature is "gene expression" as well as TCGA mutation counts for the two genes in FIG. 4B for which the feature is "number of mutations." The performance of this trained classifier is reported in FIG. 4C. The regression coefficients and correlation statistics for each of the features used in the model are shown below in Tables 5 and 6, respectively. The SVM parameters used were class_weight: none, decision function_shape: ovo, gamma: scale, kernel: linear, probability: True, shrinking: false, and tol: 1. As illustrated in FIG. 4C, the trained SVM predicts the cancer type of the 427 subjects, that is whether the subjects have the first cancer type (afflicted with HPV and having head and neck, or cervical cancer) or the second cancer type (not afflicted with HPV, but having head and neck, or cervical cancer) with a 99% specificity and 99% sensitivity for the training set of 427 subjects. The classifier was then validated against data from a cohort of 133 subjects with cervical cancer or head and neck cancer and a known HPV status. The classifier correctly identified the HPV infection status of 122 of the 133 validation subjects, with a specificity of 95% and a sensitivity of 87.5%.

TABLE 5

Regression coefficients for features used in the second SVM model for HPV detection.

| Ensembl Gene ID | Gene Name | Feature Type | Coefficient |
|---|---|---|---|
| ENSG00000170442 | KRT86 | gene_expression | 0.281204 |
| ENSG00000121005 | CRISPLD1 | gene_expression | 0.046559 |
| ENSG00000134760 | DSG1 | gene_expression | 0.044229 |

TABLE 5-continued

Regression coefficients for features used in the second SVM model for HPV detection.

| Ensembl Gene ID | Gene Name | Feature Type | Coefficient |
|---|---|---|---|
| ENSG00000149212 | SESN3 | gene_expression | −0.26422 |
| ENSG00000173157 | ADAMTS20 | gene_expression | −0.48575 |
| ENSG00000170549 | IRX1 | gene_expression | −0.09112 |
| ENSG00000077935 | SMC1B | gene_expression | 1.020826 |
| ENSG00000147889 | CDKN2A | gene_expression | 1.126704 |
| ENSG00000108947 | EFNB3 | gene_expression | −0.97171 |
| ENSG00000145824 | CXCL14 | gene_expression | −0.28714 |
| ENSG00000105278 | ZFR2 | gene_expression | −0.00985 |
| ENSG00000178222 | RNF212 | gene_expression | 0.517382 |
| ENSG00000179455 | MKRN3 | gene_expression | −0.19302 |
| ENSG00000196074 | SYCP2 | gene_expression | 0.315818 |
| ENSG00000168530 | MYL1 | gene_expression | −0.15219 |
| ENSG00000095777 | MYO3A | gene_expression | 0.465386 |
| ENSG00000182545 | RNASE10 | gene_expression | −0.36664 |
| ENSG00000144278 | GALNT13 | gene_expression | −0.26314 |
| ENSG00000099625 | C19orf26 | gene_expression | −0.43544 |
| ENSG00000145113 | MUC4 | gene_expression | −0.22115 |
| ENSG00000254221 | PCDHGB1 | gene_expression | −0.45707 |
| ENSG00000110092 | CCND1 | gene_expression | −0.65063 |
| ENSG00000240386 | LCE1F | gene_expression | 0.198233 |
| ENSG00000124134 | KCNS1 | gene_expression | 0.7377 |
| TP53 | TP53 | mutational_status | −0.4517 |
| CDKN2A | CDKN2A | mutational_status | −0.26302 |

TABLE 6

Correlation statistics for the features used in the second SVM model for HPV detection.

| Feature 1 | Feature 2 | Correlation | Highly Correlated Pair # |
|---|---|---|---|
| ENSG00000121005 | ENSG00000170442 | −0.04066 | |
| ENSG00000134760 | ENSG00000170442 | −0.1313 | |
| ENSG00000134760 | ENSG00000121005 | 0.134678 | |
| ENSG00000149212 | ENSG00000170442 | −0.25182 | |
| ENSG00000149212 | ENSG00000121005 | 0.488664 | |
| ENSG00000149212 | ENSG00000134760 | 0.355098 | |
| ENSG00000173157 | ENSG00000170442 | 0.061926 | |
| ENSG00000173157 | ENSG00000121005 | 0.506442 | |
| ENSG00000173157 | ENSG00000134760 | 0.090731 | |
| ENSG00000173157 | ENSG00000149212 | 0.275716 | |
| ENSG00000170549 | ENSG00000170442 | −0.05431 | |
| ENSG00000170549 | ENSG00000121005 | 0.297916 | |
| ENSG00000170549 | ENSG00000134760 | 0.390033 | |
| ENSG00000170549 | ENSG00000149212 | 0.16815 | |
| ENSG00000170549 | ENSG00000173157 | 0.190158 | |
| ENSG00000077935 | ENSG00000170442 | 0.508903 | |
| ENSG00000077935 | ENSG00000121005 | −0.21228 | |
| ENSG00000077935 | ENSG00000134760 | −0.28965 | |
| ENSG00000077935 | ENSG00000149212 | −0.32522 | |
| ENSG00000077935 | ENSG00000173157 | −0.09144 | |
| ENSG00000077935 | ENSG00000170549 | −0.33638 | |
| ENSG00000147889 | ENSG00000170442 | 0.249512 | |
| ENSG00000147889 | ENSG00000121005 | −0.1551 | |
| ENSG00000147889 | ENSG00000134760 | −0.05004 | |
| ENSG00000147889 | ENSG00000149212 | 0.011617 | |
| ENSG00000147889 | ENSG00000173157 | −0.05178 | |
| ENSG00000147889 | ENSG00000170549 | −0.23241 | |
| ENSG00000147889 | ENSG00000077935 | 0.562316 | |
| ENSG00000108947 | ENSG00000170442 | −0.03695 | |
| ENSG00000108947 | ENSG00000121005 | 0.324505 | |
| ENSG00000108947 | ENSG00000134760 | 0.040914 | |
| ENSG00000108947 | ENSG00000149212 | 0.141273 | |
| ENSG00000108947 | ENSG00000173157 | 0.240437 | |
| ENSG00000108947 | ENSG00000170549 | 0.365403 | |
| ENSG00000108947 | ENSG00000077935 | −0.22954 | |
| ENSG00000108947 | ENSG00000147889 | −0.29009 | |
| ENSG00000145824 | ENSG00000170442 | 0.069094 | |
| ENSG00000145824 | ENSG00000121005 | 0.248397 | |
| ENSG00000145824 | ENSG00000134760 | 0.601905 | 1 |

TABLE 6-continued

Correlation statistics for the features used in the second SVM model for HPV detection.

| Feature 1 | Feature 2 | Correlation | Highly Correlated Pair # |
|---|---|---|---|
| ENSG00000145824 | ENSG00000149212 | 0.181146 | |
| ENSG00000145824 | ENSG00000173157 | 0.192195 | |
| ENSG00000145824 | ENSG00000170549 | 0.461357 | |
| ENSG00000145824 | ENSG00000077935 | −0.2336 | |
| ENSG00000145824 | ENSG00000147889 | −0.11632 | |
| ENSG00000145824 | ENSG00000108947 | 0.261769 | |
| ENSG00000105278 | ENSG00000170442 | 0.250168 | |
| ENSG00000105278 | ENSG00000121005 | −0.12744 | |
| ENSG00000105278 | ENSG00000134760 | −0.2786 | |
| ENSG00000105278 | ENSG00000149212 | −0.08982 | |
| ENSG00000105278 | ENSG00000173157 | −0.06139 | |
| ENSG00000105278 | ENSG00000170549 | −0.22704 | |
| ENSG00000105278 | ENSG00000077935 | 0.718983 | 2 |
| ENSG00000105278 | ENSG00000147889 | 0.490566 | |
| ENSG00000105278 | ENSG00000108947 | −0.08563 | |
| ENSG00000105278 | ENSG00000145824 | −0.29907 | |
| ENSG00000178222 | ENSG00000170442 | 0.317245 | |
| ENSG00000178222 | ENSG00000121005 | −0.14501 | |
| ENSG00000178222 | ENSG00000134760 | −0.10005 | |
| ENSG00000178222 | ENSG00000149212 | −0.18412 | |
| ENSG00000178222 | ENSG00000173157 | −0.11824 | |
| ENSG00000178222 | ENSG00000170549 | −0.15257 | |
| ENSG00000178222 | ENSG00000077935 | 0.649568 | 3 |
| ENSG00000178222 | ENSG00000147889 | 0.460545 | |
| ENSG00000178222 | ENSG00000108947 | −0.12628 | |
| ENSG00000178222 | ENSG00000145824 | −0.01065 | |
| ENSG00000178222 | ENSG00000105278 | 0.495493 | |
| ENSG00000179455 | ENSG00000170442 | 0.140679 | |
| ENSG00000179455 | ENSG00000121005 | 0.420858 | |
| ENSG00000179455 | ENSG00000134760 | 0.160431 | |
| ENSG00000179455 | ENSG00000149212 | 0.267878 | |
| ENSG00000179455 | ENSG00000173157 | 0.353586 | |
| ENSG00000179455 | ENSG00000170549 | 0.222223 | |
| ENSG00000179455 | ENSG00000077935 | 0.018466 | |
| ENSG00000179455 | ENSG00000147889 | −0.04649 | |
| ENSG00000179455 | ENSG00000108947 | 0.223497 | |
| ENSG00000179455 | ENSG00000145824 | 0.236049 | |
| ENSG00000179455 | ENSG00000105278 | 0.078913 | |
| ENSG00000179455 | ENSG00000178222 | −0.00614 | |
| ENSG00000196074 | ENSG00000170442 | 0.416286 | |
| ENSG00000196074 | ENSG00000121005 | −0.17789 | |
| ENSG00000196074 | ENSG00000134760 | −0.28147 | |
| ENSG00000196074 | ENSG00000149212 | −0.14735 | |
| ENSG00000196074 | ENSG00000173157 | −0.10223 | |
| ENSG00000196074 | ENSG00000170549 | −0.35681 | |
| ENSG00000196074 | ENSG00000077935 | 0.800768 | 4 |
| ENSG00000196074 | ENSG00000147889 | 0.512305 | |
| ENSG00000196074 | ENSG00000108947 | −0.28738 | |
| ENSG00000196074 | ENSG00000145824 | −0.33066 | |
| ENSG00000196074 | ENSG00000105278 | 0.648232 | 5 |
| ENSG00000196074 | ENSG00000178222 | 0.593545 | |
| ENSG00000196074 | ENSG00000179455 | 0.016211 | |
| ENSG00000168530 | ENSG00000170442 | 0.099129 | |
| ENSG00000168530 | ENSG00000121005 | 0.284863 | |
| ENSG00000168530 | ENSG00000134760 | 0.284947 | |
| ENSG00000168530 | ENSG00000149212 | 0.07944 | |
| ENSG00000168530 | ENSG00000173157 | 0.190962 | |
| ENSG00000168530 | ENSG00000170549 | 0.32725 | |
| ENSG00000168530 | ENSG00000077935 | −0.06582 | |
| ENSG00000168530 | ENSG00000147889 | −0.02298 | |
| ENSG00000168530 | ENSG00000108947 | 0.085707 | |
| ENSG00000168530 | ENSG00000145824 | 0.389225 | |
| ENSG00000168530 | ENSG00000105278 | −0.07999 | |
| ENSG00000168530 | ENSG00000178222 | −0.02681 | |
| ENSG00000168530 | ENSG00000179455 | 0.277902 | |
| ENSG00000168530 | ENSG00000196074 | −0.12664 | |
| ENSG00000095777 | ENSG00000170442 | 0.338683 | |
| ENSG00000095777 | ENSG00000121005 | −0.05498 | |
| ENSG00000095777 | ENSG00000134760 | −0.21963 | |
| ENSG00000095777 | ENSG00000149212 | −0.14035 | |
| ENSG00000095777 | ENSG00000173157 | −0.00022 | |
| ENSG00000095777 | ENSG00000170549 | −0.28482 | |
| ENSG00000095777 | ENSG00000077935 | 0.613609 | 6 |
| ENSG00000095777 | ENSG00000147889 | 0.473209 | |
| ENSG00000095777 | ENSG00000108947 | −0.20146 | |
| ENSG00000095777 | ENSG00000145824 | −0.27264 | |
| ENSG00000095777 | ENSG00000105278 | 0.531262 | |
| ENSG00000095777 | ENSG00000178222 | 0.464102 | |
| ENSG00000095777 | ENSG00000179455 | 0.018963 | |
| ENSG00000095777 | ENSG00000196074 | 0.659032 | 7 |
| ENSG00000095777 | ENSG00000168530 | −0.05023 | |
| ENSG00000182545 | ENSG00000170442 | 0.192319 | |
| ENSG00000182545 | ENSG00000121005 | 0.196649 | |
| ENSG00000182545 | ENSG00000134760 | 0.179965 | |
| ENSG00000182545 | ENSG00000149212 | 0.053477 | |
| ENSG00000182545 | ENSG00000173157 | 0.296745 | |
| ENSG00000182545 | ENSG00000170549 | 0.136928 | |
| ENSG00000182545 | ENSG00000077935 | 0.084728 | |
| ENSG00000182545 | ENSG00000147889 | 0.050558 | |
| ENSG00000182545 | ENSG00000108947 | 0.095014 | |
| ENSG00000182545 | ENSG00000145824 | 0.221964 | |
| ENSG00000182545 | ENSG00000105278 | 0.008214 | |
| ENSG00000182545 | ENSG00000178222 | 0.048557 | |
| ENSG00000182545 | ENSG00000179455 | 0.246635 | |
| ENSG00000182545 | ENSG00000196074 | −0.01025 | |
| ENSG00000182545 | ENSG00000168530 | 0.140587 | |
| ENSG00000182545 | ENSG00000095777 | 0.017852 | |
| ENSG00000144278 | ENSG00000170442 | −0.00696 | |
| ENSG00000144278 | ENSG00000121005 | 0.437315 | |
| ENSG00000144278 | ENSG00000134760 | 0.075964 | |
| ENSG00000144278 | ENSG00000149212 | 0.34696 | |
| ENSG00000144278 | ENSG00000173157 | 0.354405 | |
| ENSG00000144278 | ENSG00000170549 | 0.299819 | |
| ENSG00000144278 | ENSG00000077935 | −0.20079 | |
| ENSG00000144278 | ENSG00000147889 | −0.04385 | |
| ENSG00000144278 | ENSG00000108947 | 0.247868 | |
| ENSG00000144278 | ENSG00000145824 | 0.219262 | |
| ENSG00000144278 | ENSG00000105278 | −0.07425 | |
| ENSG00000144278 | ENSG00000178222 | −0.06659 | |
| ENSG00000144278 | ENSG00000179455 | 0.329653 | |
| ENSG00000144278 | ENSG00000196074 | −0.15614 | |
| ENSG00000144278 | ENSG00000168530 | 0.187905 | |
| ENSG00000144278 | ENSG00000095777 | −0.14318 | |
| ENSG00000144278 | ENSG00000182545 | 0.037964 | |
| ENSG00000099625 | ENSG00000170442 | −0.08444 | |
| ENSG00000099625 | ENSG00000121005 | 0.290868 | |
| ENSG00000099625 | ENSG00000134760 | 0.195054 | |
| ENSG00000099625 | ENSG00000149212 | 0.277271 | |
| ENSG00000099625 | ENSG00000173157 | 0.277417 | |
| ENSG00000099625 | ENSG00000170549 | 0.354007 | |
| ENSG00000099625 | ENSG00000077935 | −0.14724 | |
| ENSG00000099625 | ENSG00000147889 | −0.07707 | |
| ENSG00000099625 | ENSG00000108947 | 0.562589 | |
| ENSG00000099625 | ENSG00000145824 | 0.190164 | |
| ENSG00000099625 | ENSG00000105278 | 0.027462 | |
| ENSG00000099625 | ENSG00000178222 | −0.14514 | |
| ENSG00000099625 | ENSG00000179455 | 0.241907 | |
| ENSG00000099625 | ENSG00000196074 | −0.21507 | |
| ENSG00000099625 | ENSG00000168530 | 0.211523 | |
| ENSG00000099625 | ENSG00000095777 | −0.19116 | |
| ENSG00000099625 | ENSG00000182545 | 0.209451 | |
| ENSG00000099625 | ENSG00000144278 | 0.343114 | |
| ENSG00000145113 | ENSG00000170442 | 0.458215 | |
| ENSG00000145113 | ENSG00000121005 | −0.18624 | |
| ENSG00000145113 | ENSG00000134760 | −0.18101 | |
| ENSG00000145113 | ENSG00000149212 | −0.483 | |
| ENSG00000145113 | ENSG00000173157 | −0.05284 | |
| ENSG00000145113 | ENSG00000170549 | −0.13827 | |
| ENSG00000145113 | ENSG00000077935 | 0.523288 | |
| ENSG00000145113 | ENSG00000147889 | 0.26829 | |
| ENSG00000145113 | ENSG00000108947 | −0.07115 | |
| ENSG00000145113 | ENSG00000145824 | 0.041071 | |
| ENSG00000145113 | ENSG00000105278 | 0.299568 | |
| ENSG00000145113 | ENSG00000178222 | 0.364255 | |
| ENSG00000145113 | ENSG00000179455 | 0.056978 | |
| ENSG00000145113 | ENSG00000196074 | 0.350754 | |

TABLE 6-continued

Correlation statistics for the features used in the second SVM model for HPV detection.

| Feature 1 | Feature 2 | Correlation | Highly Correlated Pair # |
|---|---|---|---|
| ENSG00000145113 | ENSG00000168530 | 0.075096 | |
| ENSG00000145113 | ENSG00000095777 | 0.323163 | |
| ENSG00000145113 | ENSG00000182545 | 0.241423 | |
| ENSG00000145113 | ENSG00000144278 | −0.1955 | |
| ENSG00000145113 | ENSG00000099625 | −0.11693 | |
| ENSG00000254221 | ENSG00000170442 | 0.003591 | |
| ENSG00000254221 | ENSG00000121005 | 0.435801 | |
| ENSG00000254221 | ENSG00000134760 | 0.007706 | |
| ENSG00000254221 | ENSG00000149212 | 0.324084 | |
| ENSG00000254221 | ENSG00000173157 | 0.334907 | |
| ENSG00000254221 | ENSG00000170549 | 0.256845 | |
| ENSG00000254221 | ENSG00000077935 | −0.18828 | |
| ENSG00000254221 | ENSG00000147889 | −0.1212 | |
| ENSG00000254221 | ENSG00000108947 | 0.437106 | |
| ENSG00000254221 | ENSG00000145824 | 0.125222 | |
| ENSG00000254221 | ENSG00000105278 | −0.12422 | |
| ENSG00000254221 | ENSG00000178222 | −0.09784 | |
| ENSG00000254221 | ENSG00000179455 | 0.311361 | |
| ENSG00000254221 | ENSG00000196074 | −0.14597 | |
| ENSG00000254221 | ENSG00000168530 | 0.090272 | |
| ENSG00000254221 | ENSG00000095777 | −0.19747 | |
| ENSG00000254221 | ENSG00000182545 | 0.116585 | |
| ENSG00000254221 | ENSG00000144278 | 0.45402 | |
| ENSG00000254221 | ENSG00000099625 | 0.325875 | |
| ENSG00000254221 | ENSG00000145113 | −0.19429 | |
| ENSG00000110092 | ENSG00000170442 | 0.215807 | |
| ENSG00000110092 | ENSG00000121005 | 0.186991 | |
| ENSG00000110092 | ENSG00000134760 | 0.078778 | |
| ENSG00000110092 | ENSG00000149212 | −0.18427 | |
| ENSG00000110092 | ENSG00000173157 | 0.182797 | |
| ENSG00000110092 | ENSG00000170549 | 0.36607 | |
| ENSG00000110092 | ENSG00000077935 | −0.05316 | |
| ENSG00000110092 | ENSG00000147889 | −0.19008 | |
| ENSG00000110092 | ENSG00000108947 | 0.453148 | |
| ENSG00000110092 | ENSG00000145824 | 0.34624 | |
| ENSG00000110092 | ENSG00000105278 | −0.08277 | |
| ENSG00000110092 | ENSG00000178222 | −0.16028 | |
| ENSG00000110092 | ENSG00000179455 | 0.212791 | |
| ENSG00000110092 | ENSG00000196074 | −0.22647 | |
| ENSG00000110092 | ENSG00000168530 | 0.234684 | |
| ENSG00000110092 | ENSG00000095777 | −0.07161 | |
| ENSG00000110092 | ENSG00000182545 | 0.262054 | |
| ENSG00000110092 | ENSG00000144278 | 0.098067 | |
| ENSG00000110092 | ENSG00000099625 | 0.409195 | |
| ENSG00000110092 | ENSG00000145113 | 0.357647 | |
| ENSG00000110092 | ENSG00000254221 | 0.157465 | |
| ENSG00000240386 | ENSG00000170442 | −0.12567 | |
| ENSG00000240386 | ENSG00000121005 | 0.11863 | |
| ENSG00000240386 | ENSG00000134760 | 0.672628 | 8 |
| ENSG00000240386 | ENSG00000149212 | 0.253078 | |
| ENSG00000240386 | ENSG00000173157 | 0.191005 | |
| ENSG00000240386 | ENSG00000170549 | 0.469055 | |
| ENSG00000240386 | ENSG00000077935 | −0.34989 | |
| ENSG00000240386 | ENSG00000147889 | −0.1204 | |
| ENSG00000240386 | ENSG00000108947 | 0.21399 | |
| ENSG00000240386 | ENSG00000145824 | 0.571567 | |
| ENSG00000240386 | ENSG00000105278 | −0.25585 | |
| ENSG00000240386 | ENSG00000178222 | −0.16551 | |
| ENSG00000240386 | ENSG00000179455 | 0.103887 | |
| ENSG00000240386 | ENSG00000196074 | −0.35606 | |
| ENSG00000240386 | ENSG00000168530 | 0.295515 | |
| ENSG00000240386 | ENSG00000095777 | −0.29516 | |
| ENSG00000240386 | ENSG00000182545 | 0.198916 | |
| ENSG00000240386 | ENSG00000144278 | 0.095936 | |
| ENSG00000240386 | ENSG00000099625 | 0.288385 | |
| ENSG00000240386 | ENSG00000145113 | −0.18358 | |
| ENSG00000240386 | ENSG00000254221 | 0.080361 | |
| ENSG00000240386 | ENSG00000110092 | 0.233552 | |
| ENSG00000124134 | ENSG00000170442 | 0.323343 | |
| ENSG00000124134 | ENSG00000121005 | −0.23394 | |
| ENSG00000124134 | ENSG00000134760 | −0.07179 | |
| ENSG00000124134 | ENSG00000149212 | −0.15515 | |
| ENSG00000124134 | ENSG00000173157 | −0.12997 | |
| ENSG00000124134 | ENSG00000170549 | −0.22963 | |
| ENSG00000124134 | ENSG00000077935 | 0.693565 | 9 |
| ENSG00000124134 | ENSG00000147889 | 0.545043 | |
| ENSG00000124134 | ENSG00000108947 | −0.2682 | |
| ENSG00000124134 | ENSG00000145824 | −0.09267 | |
| ENSG00000124134 | ENSG00000105278 | 0.616996 | 10 |
| ENSG00000124134 | ENSG00000178222 | 0.514734 | |
| ENSG00000124134 | ENSG00000179455 | 0.011375 | |
| ENSG00000124134 | ENSG00000196074 | 0.599981 | |
| ENSG00000124134 | ENSG00000168530 | 0.052773 | |
| ENSG00000124134 | ENSG00000095777 | 0.414669 | |
| ENSG00000124134 | ENSG00000182545 | 0.073025 | |
| ENSG00000124134 | ENSG00000144278 | −0.14665 | |
| ENSG00000124134 | ENSG00000099625 | −0.02252 | |
| ENSG00000124134 | ENSG00000145113 | 0.399469 | |
| ENSG00000124134 | ENSG00000254221 | −0.18319 | |
| ENSG00000124134 | ENSG00000110092 | −0.04119 | |
| ENSG00000124134 | ENSG00000240386 | −0.12953 | |
| TP53 | ENSG00000170442 | −0.203 | |
| TP53 | ENSG00000121005 | 0.171477 | |
| TP53 | ENSG00000134760 | 0.349983 | |
| TP53 | ENSG00000149212 | 0.220628 | |
| TP53 | ENSG00000173157 | 0.224804 | |
| TP53 | ENSG00000170549 | 0.322259 | |
| TP53 | ENSG00000077935 | −0.42909 | |
| TP53 | ENSG00000147889 | −0.15848 | |
| TP53 | ENSG00000108947 | 0.14238 | |
| TP53 | ENSG00000145824 | 0.289419 | |
| TP53 | ENSG00000105278 | −0.33551 | |
| TP53 | ENSG00000178222 | −0.26775 | |
| TP53 | ENSG00000179455 | 0.129312 | |
| TP53 | ENSG00000196074 | −0.40505 | |
| TP53 | ENSG00000168530 | 0.147047 | |
| TP53 | ENSG00000095777 | −0.29804 | |
| TP53 | ENSG00000182545 | 0.16223 | |
| TP53 | ENSG00000144278 | 0.296668 | |
| TP53 | ENSG00000099625 | 0.18133 | |
| TP53 | ENSG00000145113 | −0.18051 | |
| TP53 | ENSG00000254221 | 0.165337 | |
| TP53 | ENSG00000110092 | 0.109177 | |
| TP53 | ENSG00000240386 | 0.383618 | |
| TP53 | ENSG00000124134 | −0.32845 | |
| CDKN2A | ENSG00000170442 | −0.14855 | |
| CDKN2A | ENSG00000121005 | 0.088698 | |
| CDKN2A | ENSG00000134760 | 0.19446 | |
| CDKN2A | ENSG00000149212 | 0.191928 | |
| CDKN2A | ENSG00000173157 | 0.153285 | |
| CDKN2A | ENSG00000170549 | 0.231313 | |
| CDKN2A | ENSG00000077935 | −0.27452 | |
| CDKN2A | ENSG00000147889 | 0.056256 | |
| CDKN2A | ENSG00000108947 | 0.060295 | |
| CDKN2A | ENSG00000145824 | 0.121151 | |
| CDKN2A | ENSG00000105278 | −0.25297 | |
| CDKN2A | ENSG00000178222 | −0.20681 | |
| CDKN2A | ENSG00000179455 | 0.068506 | |
| CDKN2A | ENSG00000196074 | −0.2943 | |
| CDKN2A | ENSG00000168530 | 0.149041 | |
| CDKN2A | ENSG00000095777 | −0.21265 | |
| CDKN2A | ENSG00000182545 | 0.140598 | |
| CDKN2A | ENSG00000144278 | 0.120321 | |
| CDKN2A | ENSG00000099625 | 0.093298 | |
| CDKN2A | ENSG00000145113 | −0.17281 | |
| CDKN2A | ENSG00000254221 | 0.19745 | |
| CDKN2A | ENSG00000110092 | 0.00086 | |
| CDKN2A | ENSG00000240386 | 0.205975 | |
| CDKN2A | ENSG00000124134 | −0.25407 | |
| CDKN2A | TP53 | 0.436135 | |

To validate the model, the trained SVM classifier reported in FIG. 4C was tested against a validation population that had not been used to train the classifier. As detailed in FIG. 4A, the validation dataset comprised a corresponding plurality of abundance values for each subject in a dataset termed the "Testing" dataset, described in Example 2, that had cervical cancer or head and neck cancer with known HPV status. As illustrated in FIG. 4A, 133 subjects from the validation dataset were selected who satisfied these selection criteria and served as the plurality of subjects of the validation dataset. Of the 133 validation subjects, 93 had head and neck cancer and 40 had cervical cancer. Of the 93 subjects that had head and neck cancer, 28 tested positive for HPV and 65 tested negative for HPV. Of the 40 subjects that had cervical cancer, 28 tested positive for HPV and 12 tested negative for HPV. Thus, of the 133 validation subjects, 56 validation subjects were deemed to have the first cancer condition (afflicted with HPV and having head and neck, or cervical cancer) and the remaining 77 validation subjects (not afflicted with HPV, but having head and neck, or cervical cancer) were deemed to have the second cancer condition.

Each of the 133 validation subjects were run against the trained SVM whose performance is reported in FIG. 4C and thus was assigned by the SVM to either the first or second cancer class. That is, the gene abundance values for the genes listed in FIG. 4B in which the feature type was "gene expression" and the mutation count in the two genes listed in FIG. 4B in which the feature type was "number of mutations" was measured from a tumor sample for each of the 133 validation subjects and this data for each validation subject was separately input into the trained SVM model of FIG. 5C. As illustrated in FIG. 4D, the trained SVM had 95% specificity and 88% sensitivity for cancer class across the 133 validation subjects. It was found that the addition of the covariate of the number of mutations in the genes TP53 and CDKN2A to the SVM doesn't change the accuracy but improves the AUC from 0.97 to 0.98. This example shows that the trained SVM model accurately predicts viral infection in tumors using RNA expression data.

This example confirms viral infections are generally associated with an upregulation of immune responses. This example further shows that viral detection based on whole transcriptome data is a useful clinical tool in its own right, and further can be combined with existing diagnostic methods to provide insights about the viral status and tumor microenvironment in a single test.

Example 4—Epstein Barr Virus Detection

Referring to FIGS. 5A through 5D, a classifier for determining EBV viral status was trained using gene expression from the tumor RNA-seq data of a training population, where each subject in the training population had been diagnosed with gastric cancer.

In accordance with block 204 of FIG. 2A, the training dataset was obtained. Here, the dataset comprised a corresponding plurality of abundance values for each subject in the TCGA, described in Example 1, that had gastric cancer with known EBV status. As illustrated in FIG. 5A, there were 212 subjects in the TCGA that satisfied these selection criteria and thus served as the plurality of subjects of the training dataset. Of the 212 subjects, 21 tested positive for EBV and 191 tested negative for EBV. Thus, of the 212 subjects, 21 subjects were deemed to have the first cancer condition (afflicted with EBV and having gastric cancer) and the remaining 191 subjects were deemed to have the second cancer condition (not afflicted with EBV, but having gastric cancer).

Next, in accordance with block 218 of FIG. 2C and block 228 of FIG. 2D, the gene expression values from whole exome RNA data in the TCGA dataset for the 212 subjects was used to identify a discriminating gene set by regression, in which the gene expression values obtained from whole exome mRNA expression data for the 212 subjects in the TCGA dataset served as independent variables and the indication of whether a respective subject had the first cancer condition (afflicted with EBV and having gastric cancer) or the second cancer condition (not afflicted with EBV, but having gastric cancer) served as the dependent variable. More specifically, in accordance with block 228 of FIG. 2D, the dataset consisting of 212 subjects was split into ten sets (ten splits). Each set included two or more subjects afflicted with the first cancer condition and two or more subjects afflicted with the second cancer condition. Each respective set of the ten sets (splits) was independently subjected to regression in which whole exome mRNA expression data for the subjects of the respective set served as independent variables and the indication of whether a respective subject in the respective set had the first or second cancer condition served as the dependent variable. Each regression (split) was performed with L1 (LASSO) regularization in accordance with block 238 of FIG. 2E. Since L1 regularization leads to sparse coefficients, only a small subset of genes had non-zero coefficients for each set. Only the genes with non-zero coefficients in more than 80% of the sets were included in the final model. In other words, only those genes that had non-zero regression coefficients for at least eight of the ten sets (splits) were accepted into the discriminating set of genes on the basis of their expression data. The list of genes that satisfied this requirement are the ones listed in FIG. 5B in which the feature type is "gene expression." Furthermore, FIG. 6B illustrates principal component analysis of the abundance values of the genes listed in FIG. 5B across the training set. FIG. 6B illustrates that a plot of the first and second PCA values for each of the subjects in the training set break out into two distinct groups, corresponding to the first cancer condition (group 606) and second cancer condition (606), indicating the power of the abundance values of the genes listed in FIG. 5B to discriminate between the first and second cancer state.

In some embodiments, additional genes were included in the discriminating set of genes based on the presence or absence of mutations (e.g., the number of mutations) in the additional genes. In this example, as detailed in FIG. 5B, the genes PIK3CA and TP53 were included in the discriminating set of genes and the feature for these genes was the number of times mutations were observed in these genes in each of the respective 212 subjects of the training set.

Next, in accordance with block 242 of FIG. 2E, the respective abundance values for the discriminating gene set and the respective indication of cancer condition across the 212 subjects was used to train a classifier to discriminate between the first and second cancer conditions as a function of respective abundance values for the discriminating gene set. In a first model, the classifier used was a logistic regression classifier with a L1 regularization, in which the training was the 212 subjects but only using TCGA gene abundance levels for the genes listed in FIG. 5B for which the feature is "gene expression." In a second model, the classifier used was a logistic regression classifier with a L1 regularization, in which the training was on the 212 subjects using the TCGA gene abundance levels for the genes listed in FIG. 5B for which the feature is "gene expression" as well as TCGA mutation counts for the two genes in FIG. 5B for which the feature is "number of mutations." In a third model, the classifier used was a support vector machine (SVM) classifier from Scikit-learn, as disclosed in Pedregosa et al.

2011, "Machine Learning in Python," JMLR 12, pp. 2825-2830, hereby incorporated by reference, in which the training was on the 212 subjects but only using the TCGA gene abundance levels for the genes listed in FIG. 5B for which the feature is "gene expression." When validated against data from a cohort of 55 subjects with gastric cancer and a known EBV status, the classifier correctly identified the EBV infection status of 54 or the 55 validation subjects, with a specificity of 100% and a sensitivity of 75%.

Figure 5C:
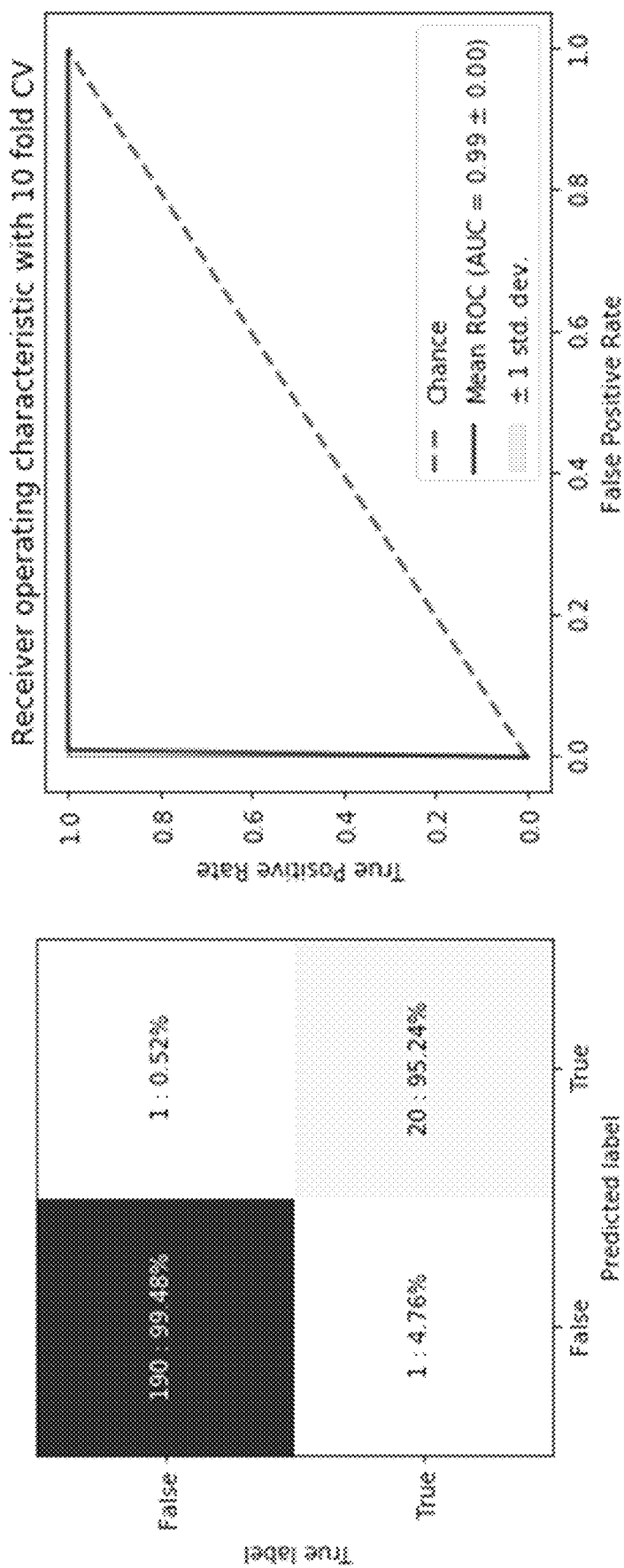
FIG. 5C illustrates performance metrics for a trained support vector machine, against the training dataset, for discriminating between a first cancer condition associated with an EBV oncogenic viral infection and a second cancer condition not associated with an EBV oncogenic viral infection, in accordance with some embodiments of the present disclosure.

In a fourth model, the classifier used was this same SVM classifier, in which the training was on the 212 subjects and using the TCGA gene abundance levels for the genes listed in FIG. 4B for which the feature is "gene expression" as well as TCGA mutation counts for the two genes in FIG. 4B for which the feature is "number of mutations." The performance of this trained classifier is reported in FIG. 5C. The regression coefficients and correlation statistics for each of the features used in the model are shown below in Tables 7 and 8, respectively. The SVM parameters used were class_weight: none, decision function_shape: ovo, gamma: scale, kernel: linear, probability: True, shrinking: false, and tol: 1. As illustrated in FIG. 5C, the trained SVM predicts the cancer type of the 212 subjects, that is whether the subjects have the first cancer type (afflicted with EBV and having gastric cancer) or the second cancer type (not afflicted with EBV, but having gastric cancer) with a 99% specificity and 95% sensitivity for the training set of 212 subjects. The classifier was then validated against data from a cohort of 55 subjects with gastric cancer and a known EBV status. The classifier correctly identified the EBV infection status of 54 of the 55 validation subjects, with a specificity of 100% and a sensitivity of 75%.

TABLE 7

Regression coefficients for features used in the second SVM model for EBV detection.

| Ensembl Gene ID | Gene Name | Feature Type | Coefficient |
| --- | --- | --- | --- |
| ENSG00000111319 | SCNN1A | gene_expression | −1.2572 |
| ENSG00000113722 | CDX1 | gene_expression | −0.66772 |
| ENSG00000124249 | KCNK15 | gene_expression | −1.04267 |
| ENSG00000126583 | PRKCG | gene_expression | 0.63421 |
| ENSG00000135480 | KRT7 | gene_expression | −0.94353 |
| ENSG00000145506 | NKD2 | gene_expression | −0.66031 |
| ENSG00000151025 | GPR158 | gene_expression | −0.62359 |
| ENSG00000165215 | CLDN3 | gene_expression | −1.67826 |
| ENSG00000176083 | ZNF683 | gene_expression | 0.592752 |
| TP53 | TP53 | mutational_status | −0.61494 |
| PIK3CA | PIK3CA | mutational_status | 0.520923 |

TABLE 8

Correlation statistics for the features used in the second SVM model for EBV detection.

| Feature 1 | Feature 2 | Correlation |
| --- | --- | --- |
| ENSG00000113722 | ENSG00000111319 | 0.104724 |
| ENSG00000124249 | ENSG00000111319 | 0.429128 |
| ENSG00000124249 | ENSG00000113722 | −0.20282 |
| ENSG00000126583 | ENSG00000111319 | −0.16662 |
| ENSG00000126583 | ENSG00000113722 | 0.11953 |
| ENSG00000126583 | ENSG00000124249 | −0.14871 |
| ENSG00000135480 | ENSG00000111319 | 0.452307 |
| ENSG00000135480 | ENSG00000113722 | −0.42786 |
| ENSG00000135480 | ENSG00000124249 | 0.650944 |
| ENSG00000135480 | ENSG00000126583 | −0.10185 |
| ENSG00000145506 | ENSG00000111319 | −0.12667 |
| ENSG00000145506 | ENSG00000113722 | 0.051531 |
| ENSG00000145506 | ENSG00000124249 | 0.109441 |
| ENSG00000145506 | ENSG00000126583 | −0.19096 |
| ENSG00000145506 | ENSG00000135480 | −0.01553 |
| ENSG00000151025 | ENSG00000111319 | 0.174624 |
| ENSG00000151025 | ENSG00000113722 | −0.03132 |
| ENSG00000151025 | ENSG00000124249 | 0.187233 |
| ENSG00000151025 | ENSG00000126583 | −0.20936 |
| ENSG00000151025 | ENSG00000135480 | 0.131621 |
| ENSG00000151025 | ENSG00000145506 | 0.001804 |
| ENSG00000165215 | ENSG00000111319 | 0.264786 |
| ENSG00000165215 | ENSG00000113722 | 0.578454 |
| ENSG00000165215 | ENSG00000124249 | 0.22998 |
| ENSG00000165215 | ENSG00000126583 | −0.02774 |
| ENSG00000165215 | ENSG00000135480 | 0.048908 |
| ENSG00000165215 | ENSG00000145506 | 0.005267 |
| ENSG00000165215 | ENSG00000151025 | 0.009025 |
| ENSG00000176083 | ENSG00000111319 | 0.028252 |
| ENSG00000176083 | ENSG00000113722 | −0.16096 |
| ENSG00000176083 | ENSG00000124249 | −0.24414 |
| ENSG00000176083 | ENSG00000126583 | 0.147816 |
| ENSG00000176083 | ENSG00000135480 | −0.10308 |
| ENSG00000176083 | ENSG00000145506 | 0.029865 |
| ENSG00000176083 | ENSG00000151025 | −0.12438 |
| ENSG00000176083 | ENSG00000165215 | −0.2766 |
| TP53 | ENSG00000111319 | 0.11033 |
| TP53 | ENSG00000113722 | −0.00053 |
| TP53 | ENSG00000124249 | 0.157624 |
| TP53 | ENSG00000126583 | −0.2485 |
| TP53 | ENSG00000135480 | 0.17002 |
| TP53 | ENSG00000145506 | 0.164913 |
| TP53 | ENSG00000151025 | 0.185344 |
| TP53 | ENSG00000165215 | 0.309497 |
| TP53 | ENSG00000176083 | −0.05715 |
| PIK3CA | ENSG00000111319 | −0.36062 |
| PIK3CA | ENSG00000113722 | −0.10222 |
| PIK3CA | ENSG00000124249 | −0.20278 |
| PIK3CA | ENSG00000126583 | 0.29328 |
| PIK3CA | ENSG00000135480 | −0.34703 |
| PIK3CA | ENSG00000145506 | −0.15388 |
| PIK3CA | ENSG00000151025 | −0.23884 |
| PIK3CA | ENSG00000165215 | −0.11482 |
| PIK3CA | ENSG00000176083 | 0.04957 |
| PIK3CA | TP53 | −0.10617 |

To validate the model, the trained SVM classifier reported in FIG. 5C was tested against a validation population that had not been used to train the classifier. As detailed in FIG. 5A, the validation dataset comprised a corresponding plurality of abundance values for each subject in a dataset termed the "Testing" dataset, described in Example 2, that had gastric cancer with known EBV status. As illustrated in FIG. 5A, 55 subjects were selected from the validation dataset that satisfied these selection criteria and served as the plurality of subjects of the validation dataset. Of the 55 validation subjects, 4 tested positive for EBV and 51 tested negative for EBV. Thus, of the 55 validation subjects, 4 validation subjects were deemed to have the first cancer condition (afflicted with EBV and having gastric cancer) and the remaining 51 subjects (not afflicted with EBV, but having gastric cancer) were deemed to have the second cancer condition.

Figure 5D:
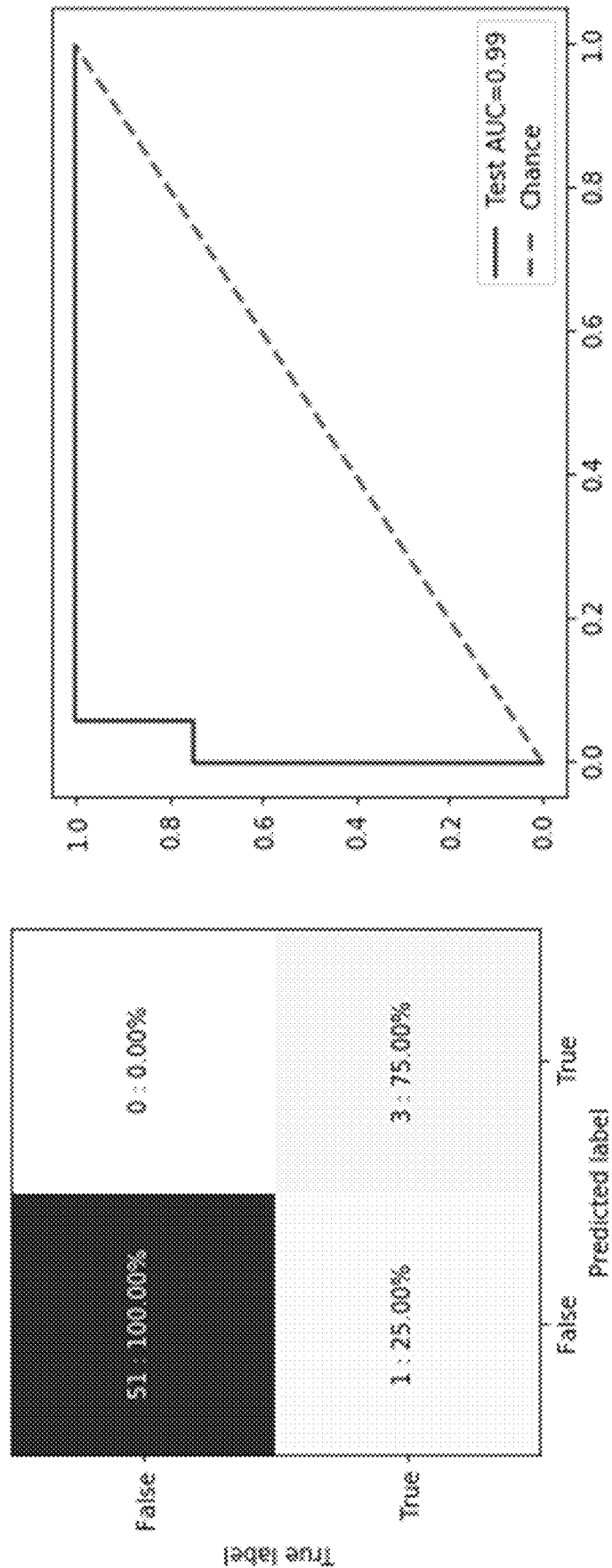
FIG. 5D illustrates performance metrics for a trained support vector machine, against a validation dataset, for discriminating between a first cancer condition associated with an EBV oncogenic viral infection and a second cancer condition not associated with an EBV oncogenic viral infection, in accordance with some embodiments of the present disclosure.

Each of the 55 validation subjects were run against the trained SVM whose performance is reported in FIG. 5C and thus was assigned by the SVM to either the first or second cancer class. That is, the gene abundance values for the genes listed in FIG. 5B in which the feature type was "gene expression" and the mutation count in the two genes listed in FIG. 5B in which the feature type was "number of mutations" was measured from a tumor sample for each of the 55 validation subjects and this data for validation subject was separately input into the trained SVM model of FIG. 5C. As illustrated in FIG. 5D, the trained SVM had 75% specificity and 100% sensitivity for cancer class using such data across the 55 validation subjects. This example shows that the trained SVM model accurately predicts viral infection in tumors using RNA expression data. This example confirms viral infections are generally associated with an upregulation of immune responses. This example further shows that viral detection based on whole transcriptome data is a useful clinical tool in its own right, and further can be combined with existing diagnostic methods to provide insights about the viral status and tumor microenvironment in a single test.

Example 5—Obtaining Normalized RNA Count Data

In this example, patient samples were processed through RNA whole exome short-read next generation sequencing (NGS) to generate RNA sequencing data, and the RNA sequencing data were processed by a bioinformatics pipeline to generate a RNA-seq expression profile for each patient sample. Specifically, solid tumor total nucleic acid (DNA and RNA) was extracted from macrodissected FFPE tissue sections and digested by proteinase K to eliminate proteins. RNA was purified from the total nucleic acid by TURBO DNase-I to eliminate DNA, followed by a reaction cleanup using RNA clean XP beads to remove enzymatic proteins. The isolated RNA was subjected to a quality control protocol using RiboGreen fluorescent dye to determine concentration of the RNA molecules.

Library preparation was performed using the KAPA Hyper Prep Kit in which 100 ng of RNA was heat fragmented in the presence of magnesium to an average size of 200 bp. The libraries were then reverse transcribed into cDNA and Roche SeqCap dual end adapters were ligated onto the cDNA. cDNA libraries were then purified and subjected to size selection using KAPA Hyper Beads. Libraries were then PCR amplified for 10 cycles and purified using Axygen MAG PCR clean up beads. Quality control was performed using a PicoGreen fluorescent kit to determine cDNA library concentration. cDNA libraries were then pooled into 6-plex hybridization reactions. Each pool was treated with Human COT-1 and IDT xGen Universal Blockers before being dried in a vacufuge. RNA pools were then resuspended in IDT xGen Lockdown hybridization mix, and IDT xGen Exome Research Panel v1.0 probes were added to each pool. Pools were incubated to allow probes to hybridize. Pools were then mixed with Streptavidin-coated beads to capture the hybridized molecules of cDNA. Pools were amplified and purified once more using the KAPA HiFi Library Amplification kit and Axygen MAG PCR clean up beads, respectively. A final quality control step involving PicoGreen pool quantification, and LabChip GX Touch was performed to assess pool fragment size. Pools were cluster amplified using Illumina Paired-end Cluster Kits with a PhiX-spike in on Illumina C-Bot2, and the resulting flow cell containing amplified target-captured cDNA libraries were sequenced on an Illumina HiSeq 4000 to an average unique on-target depth of 500× to generate a FASTQ file.

In this example, the cDNA library preparation was performed with an automated system, using a liquid handling robot (SciClone NGSx).

Each FASTQ file contained a list of paired-end reads generated by the Illumina sequencer, each of which was associated with a quality rating. The reads in each FASTQ file were processed by a bioinformatics pipeline. FASTQ files were analyzed using FASTQC for rapid assessment of quality control and reads. For each FASTQ file, each read in the file was aligned to a reference genome (GRch37) using kallisto alignment software. This alignment generated a SAM file, and each SAM file was converted to BAM, BAM files were sorted, and duplicates were marked for deletion.

For each gene, the raw RNA read count for a given gene was calculated by kallisto alignment software as a sum of the probability, for each read, that the read aligns to the gene. Raw counts are therefore not integers in this example. The raw read counts were saved in a tabular file for each patient, where columns represented genes and each entry represented the raw RNA read count for that gene.

Raw RNA read counts were then normalized to correct for GC content and gene length using full quantile normalization and adjusted for sequencing depth via the size factor method. Normalized RNA read counts were saved in a tabular file for each patient, where columns represented genes and each entry represented the raw RNA read count for that gene.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIGS. 1A, 1B, and/or as described in FIGS. 2A, 2B, 2C, 2D, 2E, and 3. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for discriminating between a first cancer condition and a second cancer condition in a subject with cervical cancer, wherein the first cancer condition is associated with human papilloma virus (HPV) infection and the second cancer condition is associated with an HPV-free status, the method comprising:
   at a computer system comprising at least one processor and a memory storing at least one program for execution by the at least one processor
   (A) obtaining a dataset for the subject, the dataset comprising a plurality of abundance values, wherein each respective abundance value in the plurality of abundance values quantifies a level of expression of a corresponding gene, in a discriminating gene set, in a cancerous tissue from the subject;

(B) inputting the dataset to a classifier trained to discriminate between at least the first cancer condition and the second cancer condition based on abundance values for the discriminating gene set in a cancerous tissue of a subject, thereby determining a cancer condition of the subject; and (C) treating the subject for cancer by:
  when the classifier result indicates that the subject has cervical cancer associated with an HPV infection, administering a first therapy tailored for treatment of cervical cancer associated with an HPV infection, and
  when the classifier result indicates that the subject has cervical cancer not associated with an HPV infection, administering a second therapy tailored for treatment of cervical cancer not associated with an HPV infection.

2. The method of claim 1, wherein the dataset further comprises a variant allele count for one or more variant alleles at one or more locus in the genome of the cancerous tissue from the subject.

3. The method of claim 1, wherein the discriminating gene set comprises at least five genes selected from the group consisting of KRT86, CRISPLD1, DSG1, SESN3, ADAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1.

4. The method of claim 3, wherein the discriminating gene set comprises at least ten genes selected from the group consisting of KRT86, CRISPLD1, DSG1, SESN3, ADAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1.

5. The method of claim 3, wherein the discriminating gene set comprises at least twenty genes selected from the group consisting of KRT86, CRISPLD1, DSG1, SESN3, ADAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1.

6. The method of claim 3, wherein the discriminating gene set comprises KRT86, CRISPLD1, DSG1, SESN3, ADAMTS20, IRX1, SMC1B, CDKN2A, EFNB3, CXCL14, ZFR2, RNF212, MKRN3, SYCP2, MYL1, MYO3A, RNASE10, GALNT13, C19orf26, MUC4, PCDHGB1, CCND1, LCE1F, and KCNS1.

7. The method of claim 3, wherein the dataset further comprises a variant allele count for TP53 (ENSG00000141510) and CDKN2A (ENSG00000147889) in the genome of the cancerous tissue from the subject.

8. The method of claim 1, wherein the first therapy tailored for treatment of cervical cancer associated with an HPV infection comprises a therapeutic vaccine or an adoptive cell therapy.

9. The method of claim 8, wherein the second therapy tailored for treatment of cervical cancer not associated with an HPV infection is a chemotherapy regimen.

10. The method of claim 9, wherein the chemotherapy regimen comprises co-administration of cisplatin and a therapeutic agent selected from the group consisting of 5-fluorouracil, paclitaxel, and bevacizumab.

11. The method of claim 1, wherein the second therapy tailored for treatment of cervical cancer not associated with an HPV infection is a chemotherapy regimen.

12. The method of claim 11, wherein the chemotherapy regimen comprises co-administration of cisplatin and a second therapeutic agent selected from the group consisting of 5-fluorouracil, paclitaxel, and bevacizumab.

13. The method of claim 1, wherein the classifier was trained by a method comprising:

(1) obtaining a dataset comprising, for each respective subject in a plurality of subjects of a species: (i) a corresponding plurality of abundance values, wherein each respective abundance value in the corresponding plurality of abundance values quantifies a level of expression of a corresponding gene, in a plurality of genes, in a tumor sample of the respective subject, and (ii) an indication of cancer condition of the respective subject, wherein the indication of cancer condition identifies whether the respective subject has the first cancer condition or the second cancer condition, and wherein the plurality of subjects includes a first subset of subjects that are afflicted with the first cancer condition and a second subset of subjects that are afflicted with the second condition;

(2) identifying the discriminating gene set using the corresponding plurality of abundance values and respective indication of the cancer condition of respective subjects in the plurality of subjects, wherein the discriminating gene set comprises a subset of the plurality of genes; and (3) using the respective abundance values for the discriminating gene set and the respective indication of cancer condition across the plurality of subjects to train a classifier to discriminate between the first cancer condition and the second cancer condition as a function of respective abundance values for the discriminating gene set.

* * * * *